United States Patent
Berger et al.

(10) Patent No.: US 9,260,441 B2
(45) Date of Patent: Feb. 16, 2016

(54) HETEROARYL COMPOUNDS WITH CYCLIC BRIDGING UNIT

(71) Applicant: Intervet Inc., Summit, NJ (US)

(72) Inventors: Michael Berger, Wiesbaden (DE); Marko Eck, Wiesbaden (DE); Christopher Kern, Edenkoben (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/387,437

(22) PCT Filed: Mar. 27, 2013

(86) PCT No.: PCT/EP2013/056466
§ 371 (c)(1),
(2) Date: Sep. 23, 2014

(87) PCT Pub. No.: WO2013/144180
PCT Pub. Date: Oct. 3, 2013

(65) Prior Publication Data
US 2015/0080365 A1    Mar. 19, 2015

(30) Foreign Application Priority Data
Mar. 28, 2012 (EP) .................................... 12161723

(51) Int. Cl.
| | |
|---|---|
| *A61K 31/497* | (2006.01) |
| *C07D 401/00* | (2006.01) |
| *C07D 487/08* | (2006.01) |
| *C07D 213/74* | (2006.01) |
| *C07D 213/82* | (2006.01) |
| *C07D 213/85* | (2006.01) |
| *C07D 213/89* | (2006.01) |
| *C07D 215/38* | (2006.01) |
| *C07D 401/04* | (2006.01) |
| *C07D 401/12* | (2006.01) |
| *C07D 239/42* | (2006.01) |
| *C07D 271/113* | (2006.01) |
| *C07D 277/42* | (2006.01) |
| *C07D 277/56* | (2006.01) |
| *C07D 271/07* | (2006.01) |
| *C07D 277/46* | (2006.01) |

(52) U.S. Cl.
CPC ............ *C07D 487/08* (2013.01); *C07D 213/74* (2013.01); *C07D 213/82* (2013.01); *C07D 213/85* (2013.01); *C07D 213/89* (2013.01); *C07D 215/38* (2013.01); *C07D 239/42* (2013.01); *C07D 271/07* (2013.01); *C07D 271/113* (2013.01); *C07D 277/42* (2013.01); *C07D 277/46* (2013.01); *C07D 277/56* (2013.01); *C07D 401/04* (2013.01); *C07D 401/12* (2013.01)

(58) Field of Classification Search
CPC ........................... A61K 31/497; C07D 401/00
See application file for complete search history.

(56) References Cited

U.S. PATENT DOCUMENTS

| 4,189,484 A | 2/1980 | Mizogami et al. |
| 4,352,928 A | 10/1982 | Hiranuma et al. |
| 4,426,382 A * | 1/1984 | Sato et al. ................ 514/252.17 |
| 2007/0049578 A1 | 3/2007 | Edwards et al. |

FOREIGN PATENT DOCUMENTS

| WO | 2005011655 A2 | 2/2005 |
| WO | 2006061147 A1 | 6/2006 |
| WO | 2010115688 A1 | 10/2010 |
| WO | 2011031896 A2 | 3/2011 |
| WO | 2012041872 A1 | 4/2012 |
| WO | WO 2012/041872 * | 4/2012 ........... C07D 409/04 |

OTHER PUBLICATIONS

XP-002675685, entered into STN on Sep. 12, 2011.*
XP-002675682, entered into STN on Sep. 11, 2011.*
XP002675684, entered into STN on Mar. 11, 2005.*
XP-002675691, entered into STN on May 11, 2004.*
XP-002675687, entered into STN on Mar. 19, 2010.*
XP-002675689, entered into STN on Mar. 6, 2008.*
XP-002675686, entered into STN on Apr. 29, 2007.*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
West, Anthony R., Solid State Chemistry and Its Applications, Wiley, New York, 1988, 358.*
Gai et al., "Synthesis of triazolo- and tetrazolo-tetrahydroisoquinolines and isoquinolines via temperature controlled palladium catalysed allene/azide incorporation/intramolecular 1,3-dipolar cycloaddition cascades", Tetrahedron Letters, 2005, pp. 5899-5902, vol. 46(35).
Guillaumel et al., "Synthesis of bis-heteroaryl piperazine derivatives as potential reverse trancriptase inhibitors", Journal of Heterocyclic Chemistry, 2001, pp. 985-988, vol. 38.
International Search Report for corresponding PCT Application No. PCT/EP2013/056466, mailed on May 24, 2013.
Saadeh et al., "Synthesis of Novel Hybrid Molecules from Precursors With Known Antiparasitic Activity", Macromolecules, American Chemical Society, 2009, pp. 1483-1494, vol. 14(4).
Westman et al., "Cascade synthesis with (triphenylphosphoranylidene) ethenone as a versatile reagent for fast synthesis of heterocycles and unsaturated amides under microwave dielectric heating", Combinatorial chemistry and high throughput screening, 2002, pp. 571-574, vol. 5(7).

(Continued)

*Primary Examiner* — Erich A Leeser

(57) ABSTRACT

This invention relates to certain heteroaryl compounds for use as medicaments, more specifically as medicaments for treating animals. The medicament can be used for the treatment of helminth infections and the treatment of parasitosis caused by helminth infections. This invention also relates to uses of the compounds to make medicaments and treatments comprising the administration of the compounds to animals in need of the treatments. This invention also relates to pharmaceutical compositions and kits comprising the compounds.

21 Claims, No Drawings

(56) References Cited

OTHER PUBLICATIONS

XP-002675681—Database Registry [Online] Chemical Abstracts Service, Retrieved from STN Accession No. 922359-52-3, dated Feb. 22, 2007.
XP-002675682—Database Registry [Online] Chemical Abstracts Service, Retrieved from STN Accession No. 1331502-87-4, dated Sep. 12, 2011.
XP-002675683—Database Registry [Online] Chemical Abstracts Service, Retrieved from STN Accession No. 1155978-52-1, dated Jun. 11, 2009.
XP-002675684—Database Registry [Online] Chemical Abstracts Service, Retrieved from STN Accession No. 845304-26-9, dated Mar. 11, 2009.
XP-002675685—Database Registry [Online] Chemical Abstracts Service, Retrieved from STN Accession No. 1331502-63-6, dated Sep. 12, 2011.
XP-002675686—Database Registry [Online] Chemical Abstracts Service, Retrieved from STN Accession No. 933228-56-9, dated Apr. 29, 2007.
XP-002675687—Database Registry [Online] Chemical Abstracts Service, Retrieved from STN Accession No. 1211918-66-9, dated Mar. 19, 2010.
XP-002675688—Database Registry [Online] Chemical Abstracts Service, Retrieved from STN Accession No. 1302965-72-5, dated May 30, 2011.
XP-002675689—Database Registry [Online] Chemical Abstracts Service, Retrieved from STN Accession No. 1006831-63-5, dated Mar. 6, 2008.
XP-002675690—Database Registry [Online] Chemical Abstracts Service, Retrieved from STN Accession No. 904516-38-7, dated Aug. 25, 2006.
XP-002675691—Database Registry [Online] Chemical Abstracts Service, Retrieved from STN Accession No. 681163-43-9, dated May 11, 2004.
XP-002696180—Database Registry [Online] Chemical Abstracts Service, Retrieved from STN Accession No. 1385405-18-4, dated Aug. 2, 2012.
European Search Report for EP Application No. 12161723.7, mailed on May 23, 2012.

* cited by examiner

HETEROARYL COMPOUNDS WITH CYCLIC BRIDGING UNIT

CROSS-REFERENCE TO RELATED APPLICATIONS

This application is a national stage entry under 35 U.S.C. §371 of PCT/EP2013/056466, filed on Mar. 27, 2013, which claims priority to EP Application No. 12161723.7, filed on Mar. 28, 2012. The content of PCT/EP2013/0056466 is hereby incorporated by reference in its entirety.

FIELD OF THE INVENTION

This invention relates to novel heteroaryl compounds, in particular for use as medicaments, more specifically as medicaments for animals, in particular non-human animals. The medicament can preferably be used for the treatment of helminth infections. This invention also relates to uses of the compounds to make medicaments and treatments comprising the administration of the compounds to animals in need of the treatments. Moreover this invention relates to pharmaceutical compositions and kits comprising the compounds.

BACKGROUND OF THE INVENTION

Parasitic diseases in animals cause substantial suffering and economic losses throughout the world. Thus, treatment of parasitic infections remains an important global endeavor. The causative organisms include helminths, such as nematodes, cestodes, and trematodes. These organisms can infect, for example, the stomach, intestinal tract, lymphatic system, muscle tissues, kidney, liver, lungs, heart, and brain of animals.

There are many known drugs (or "anthelmintic agents") available to treat various helminith parasite infections, see, e.g., McKellar, Q. A., et al., "Veterinary anthelmintics: old and new," *Review: Trends in Parasitology*, 20(10), 456-61 (October 2004). These anthelmintic agents treat specifically either nematode, cestode or trematode infections or have a broader anthelmintic spectrum. An example of an anthelmintic agent with sole effect on cestodes (tapeworms) is praziquantel. Some primary nematicidal compounds like fenbendazole, mebendazole, oxfendazole, albendazole have a broader spectrum than nematodes and treat cestode infections as well. Closantel, rafoxanide and triclabendazole are examples of specific compounds for the treatment of trematode infections (flukes).

While many parasitic infections can be treated with known drugs, evolutionary development of resistance by the parasites can render such drugs obsolete over time, see, e.g., Jabbar, A., et al., "Anthelmintic resistance: the state of play revisited," *Life Sciences*, 79, 2413-31 (2006). In addition, known drugs may have other deficiencies, such as limited spectrum of activity and the need for repeated treatments.

In WO 2008/028689 A1 certain N-(1-phtalazin-1-ylpiperidin-4-yl)amides are described as EP2 receptor modulators. WO 2008/028691 A1 discloses as EP2 receptors certain N-(1-hetaryl-piperidin-4-yl)(het)arylamides.

WO 2006/061147 discloses certain 1-phenyl-3-piperazine-pyrazoles for the control of pests including helminths.

There still exists a need for new medicaments, such as antiparasitic agents to ensure safe, effective, and convenient treatment of a wide range of parasitic helminth infections over a long period of time.

SUMMARY OF THE INVENTION

Briefly, this invention relates to compounds that can generally be used as a medicament for animals. The compounds correspond in structure to formula (I) or its pharmaceutically acceptable salts, solvates, N-oxides or prodrugs

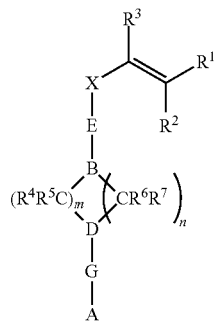

Formula I wherein
$R^1$ is hydrogen, halogen, alkyl, alkoxy, alkoxyalkyl, alkenyl, alkynyl, alkylthio, alkylthioalkyl, alkylcarbonyl, $SF_5$, alkoxycarbonyl, phenyl, thiophenyl, furanyl, imidazolyl wherein each of the carbon-containing radicals optionally is substituted by one or more halogen atoms, preferably fluorine atoms, $R^2$ is hydrogen, halogen, alkyl, alkoxy, alkenyl, alkynyl, alkylthio, alkoxyalkyl, alkylthioalkyl, alkylcarbonyl, alkylsulfonyl, $SF_5$, alkoxycarbonyl, phenyl, thiophenyl, furanyl, imidazolyl wherein each of the carbon-containing radicals optionally is substituted by one or more halogen atoms, preferably fluorine atoms, preferably $R^2$ is hydrogen, halogen, alkyl or alkoxy.

$R^3$ is hydrogen, halogen or alkyl, wherein each of the carbon atoms of the alkyl is optionally substituted by one or more halogen atoms, preferably fluorine atoms, preferably $R^3$ is hydrogen $R^4$ is hydrogen or alkyl, preferably hydrogen
$R^5$ is hydrogen, or alkyl, preferably hydrogen
$R^6$ is hydrogen, alkyl, phenyl or benzyl, preferably hydrogen
$R^7$ is hydrogen or alkyl, or $R^6$ or $R^7$ are joined together with $R^4$ or $R^5$ to form a C1-C3 alkylene group which is optionally substituted by one or more alkyl radicals,
m, n is 1-3,
X is CO, CS or $SO_2$, preferably CO
E is a bond or $NR^8$ wherein $R^8$ is hydrogen or alkyl, preferably hydrogen
G is a bond or $NR^9$ wherein $R^9$ is hydrogen or alkyl, preferably hydrogen
B is N or $CR^{10}$ wherein $R^{10}$ is hydrogen or alkyl, preferably hydrogen
D is N or $CR^{11}$ wherein $R^{11}$ is hydrogen or alkyl, preferably hydrogen
A is a heteroaryl, chosen from the group consisting of a 6 membered aromate according to formula II and a 5 membered heteroaromate according to formula III,

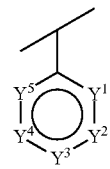

Formula II

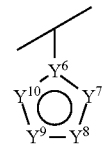

Formula III wherein in formula II:

$Y^1, Y^2, Y^4$ and $Y^5$ may be N or $CR^{12}$, wherein at least one and at most two of $Y^1, Y^2, Y^4$ and $Y^5$ is N, $Y^3$ is $CR^{13}$, $R^{12}$ is hydrogen, alkyl, alkoxy, alkylthio, halogen, nitrilo, nitro, alkylcarbonyl, alkoxycarbonyl, aminocarbonyl, alkylaminocarbonyl, dialkylaminocarbonyl, aminosulfonyl, alkylsulfonyl, amino, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms, $R^{13}$ is hydrogen, alkyl, alkoxy, alkylthio, halogen, nitrilo, nitro, alkoxycarbonyl, aminocarbonyl, alkylaminocarbonyl, dialkylaminocarbonyl, alkylsulfonyl, aminosulfonyl, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms, $Y^1$ and $Y^2$ may form a ring system or $Y^2$ and $Y^3$ may form a ring system or $Y^3$ and $Y^4$ may form a ring system or $Y^4$ and $Y^5$ may form a ring system, and in formula III:

$Y^6$ is N or C, $Y^7, Y^8, Y^9$ and $Y^{10}$ is $CR^{14}$, $NR^{15}$, O or S, wherein at least one and at maximum three of $Y^7, Y^8, Y^9$ and $Y^{10}$ is $NR^{15}$, O or S, $R^{14}$ is hydrogen, alkyl, alkoxy, alkylthio, halogen, nitrilo, nitro, alkoxycarbonyl, aminocarbonyl, alkylsulfonyl, aminosulfonyl, alkylamino, dialkylamino, N-pyrrolidinyl, N-piperidinyl, N-morpholinyl, phenyl, wherein each of the carbon-containing radicals optionally is substituted by one or more halogen atoms, preferably fluorine atoms, $R^{15}$ is hydrogen, alkyl or missing, $Y^7$ and $Y^8$ may form a ring system or $Y^8$ and $Y^9$ may form a ring system or $Y^9$ and $Y^{10}$ may form a ring system, for use in a method of treating a helminth infection of an animal.

The invention also relates to a compound having the structure of formula (V), and solvates, N-oxides, salts and prodrugs thereof,

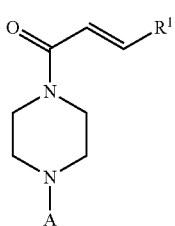

Formula (V)

wherein $R^1$ is hydrogen, halogen, alkyl, alkoxy, alkenyl, alkynyl, alkylthio, alkoxyalkyl, alkylthioalkyl, alkylcarbonyl, alkylsulfonyl, $SF_5$, alkoxycarbonyl, phenyl, thiophenyl, furanyl, imidazolyl wherein each of the carbon-containing radicals optionally is substituted by one or more halogen atoms, preferably fluorine atoms, and A is a heteroaryl, chosen from the group consisting of a 6 membered aromate according to formula II and a 5 membered heteroaromate according to formula III,

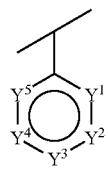

Formula II

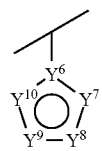

Formula III wherein in formula II:

$Y^1, Y^2, Y^4$ and $Y^5$ may be N or $CR^{12}$, wherein at least one and at most three of $Y^1, Y^2, Y^4$ and $Y^5$ is N, $Y^3$ is $CR^{13}$, $R^{12}$ is hydrogen, alkyl, alkoxy, alkylthio, halogen, nitrilo, nitro, alkylcarbonyl, alkoxycarbonyl, aminocarbonyl, alkylaminocarbonyl, dialkylaminocarbonyl, aminosulfonyl, alkylsulfoxyl, alkylsulfonyl, amino, alkylamino, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms, $R^{12}$ not being $CF_3$, $R^{13}$ is hydrogen, alkyl, alkylthio, halogen, nitrilo, nitro, alkylcarbonyl, alkoxycarbonyl, aminocarbonyl, alkylaminocarbonyl, dialkylaminocarbonyl, aminosulfonyl, alkylsulfoxyl, alkylsulfonyl, amino, alkylamino, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms, $Y^1$ and $Y^2$ may form a ring system or $Y^2$ and $Y^3$ may form a ring system or $Y^3$ and $Y^4$ may form a ring system or $Y^4$ and $Y^5$ may form a ring system, and in formula III:

$Y^6$ is N or C, $Y^7, Y^8, Y^9$ and $Y^{10}$ is $CR^{14}$, $NR^{15}$, O, S $R^{14}$ is hydrogen, alkyl, alkoxy, alkylthio, halogen, nitrilo, nitro, alkylcarbonyl, alkoxycarbonyl, aminocarbonyl, alkylaminocarbonyl, alkylsulfoxyl, alkylsulfonyl, dialkylaminocarbonyl, aminosulfonyl, amino, alkylamino, dialkylamino, N-pyrrolidinyl, N-piperidinyl, N-morpholinyl, alkylcarbonylamino, phenyl, wherein each of the carbon-containing radicals optionally is substituted by one or more halogen atoms, preferably fluorine atoms, $R^{15}$ is hydrogen, alkyl or missing, at least one of $Y^7, Y^8, Y^9$ and $Y^{10}$ is N, O or S, and $Y^7$ and $Y^8$ may form a ring system or $Y^8$ and $Y^9$ may form a ring system or $Y^9$ and $Y^{10}$ may form a ring system.

The compounds of the formula (I) and (V) and pharmaceutically acceptable solvates, N-oxides, salts and prodrugs thereof are hereinafter together referred to as "compound(s) according to this invention".

This invention is directed, in part, to a compound according to the invention and pharmaceutically acceptable solvates, N-oxides, salts and prodrugs thereof, for use as a medicament, preferably a medicament for animals for treating helminth infections. This invention also is directed, in part, to using at least one compound according to the invention and pharmaceutically acceptable solvates, N-oxides, salts and prodrugs thereof to prepare a medicament for treating an infection including diseases caused by such infections, in particular parasitoses caused by a helminth infection in animals.

This invention also is directed, in part, to pharmaceutical compositions, in particular anthelmintic compositions. The pharmaceutical compositions comprise a) at least one N-heteroaryl compound according to this invention, and b) at least one excipient, and/or at least one active compound (preferably anthelmintic compound) which differs in structure from the component a).

This invention also is directed, in part, to methods for treating a parasitic infection in animals, particularly a treatment of parasitoses caused by a helminth infection. The methods comprise administering at least one compound according to this invention to the animal.

This invention also is directed, in part, to a kit. The kit comprises at least one N-heteroaryl compound according to this invention. In addition, the kit comprises at least one other component, such as another ingredient (e.g., an excipient or active ingredient), and/or an apparatus for combining the compound with another ingredient, and/or an apparatus for administering the compound, and/or a diagnostic tool.

Further benefits of Applicants' invention will be apparent to one skilled in the art from reading this specification.

In preferred embodiments the substructure D-$(CR^4R^5)_m$-B-$(CR^6R^7)_n$ represents a ring of 4 to 8 ring atoms, preferably of 4 to 7 ring atoms, more preferably of 4 to 6 ring atoms, e.g. an azetidine, pyrrolidine, piperidine, piperazine or homopiperazine ring, wherein the ring is unsubstituted or substituted as defined above. In another preferred embodiment D-$(CR^4R^5)_m$-B-$(CR^6R^7)_n$ represents a ring of 5 or 6 ring atoms, wherein the ring is unsubstituted or substituted as defined above. In another preferred embodiment both groups $(CR^4R^5)_m$ and $(CR^6R^7)_n$ represent an ethylene group to form together with B and D a 6-ring, which is unsubstituted or substituted as defined above.

If $R^6$ or $R^7$ are joined together with $R^4$ or $R^5$ to form a $C_1$-$C_3$-alkylene group, they form for example a bridged ring, preferably of 5 to 8 ring atoms, more preferably of 5 to 7 ring atoms, even more preferably 5 to 6 ring atoms, e.g. a bridged pyrrolidine, piperidine, piperazine or homopiperazine ring, wherein the ring is unsubstituted or substituted as defined above.

The integer m is from 1 to 3, and is preferably 2. If m is larger than 1 the $CR^4R^5$-groups can be identical or different.

The integer n is from 1 to 3, and is preferably 2. If n is larger than 1 the $CR^6R^7$-groups can be identical or different.

The 6 or 5 membered aromatic group A of formula (I) represents a mono- or polycyclic ring system. A monocyclic ring system is obtained if for example the carbon/nitrogen atoms $Y^1$, $Y^2$, $Y^3$, $Y^4$ and $Y^5$ are unsubstituted or substituted but not joined together additionally to what is indicated in formula (I), in conjunction with formula (II) and (III). A polycyclic ring system is obtained if for example $Y^1$ and $Y^2$ are joined together, $Y^3$ and $Y^4$ are joined together or both $Y^1$ and $Y^2$ as well as $Y^3$ and $Y^4$ are joined together, etc.

A ring system formed by joining together neighbouring Y atoms is a saturated or non-saturated ring system (e.g. an aromatic ring system). The ring system itself is a monocyclic or polycyclic ring system, preferably a monocyclic, bicyclic or tricyclic, more preferably a monocyclic or bicyclic ring system. The ring system contains from 4 to 10 ring atoms, preferably from 5 to 8 ring atoms, more preferably from 5 to 6 ring atoms, wherein the number of ring atoms includes the Y atoms The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkoxy, $C_1$-$C_6$-alkoxycarbonyl and $C_1$-$C_6$-alkylthio.

The mentioning of the preferred embodiments of the ring system formed by joining together neighbouring Y atoms is intended to disclose all combinations of the preferred embodiments, including but not limited to a saturated, monocyclic, bicyclic or tricyclic ring system with 4 to 10 ring atoms, one, two or three ring heteroatoms from the group of nitrogen, sulphur and oxygen, which is unsubstituted or substituted by one or two radicals from the group of $C_1$-$C_6$-alkyl, $C_1$-$C_6$-alkoxy and $C_1$-$C_6$-alkylthio, or an unsaturated, monocyclic or bicyclic ring system with 5 to 6 ring atoms, one or two ring heteroatoms, which is unsubstituted, etc.

DETAILED DESCRIPTION OF PREFERRED EMBODIMENTS

In a preferred embodiment of a compound according to the invention, in particular for use in the treatment of a helminth infection, the substituents are as follows. $R^1$ is hydrogen, halogen, alkyl, haloalkyl, alkoxy, alkylthio, alkenyl, alkylcarbonyl, alkoxycarbonyl, alkinyl, alkylthioalkyl, alkoxyalkyl, $SF_5$, thiophenyl, imidazolyl, phenyl, furanyl wherein each of the carbon-containing radicals optionally is substituted by one or more halogen atoms; $R^2$ is hydrogen, halogen or alkyl, preferably hydrogen; $R^3$ is hydrogen, halogen or alkyl, preferably hydrogen; $R^4$, $R^5$, $R^6$ and $R^7$ is hydrogen; $R^{10}$ is hydrogen, $R^{11}$ is hydrogen, and in formula II: one or two of $Y^1$, $Y^2$, $Y^4$ and $Y^5$ are N; $R^{12}$ is hydrogen, alkyl, alkoxy, alkylthio, haloalkyl, haloalkoxy, haloalkylthio, halogen, nitrilo, amino, nitro, alkylsulfonyl, alkylsulfoxyl, alkylcarbonyl, alkoxycarbonyl, aminocarbonyl, alkylaminocarbonyl, dialkylaminocarbonyl; $R^{13}$ is hydrogen, alkyl, alkylthio, haloalkyl, haloalkoxy, haloalkylthio, halogen, nitrilo, amino, nitro, alkylsulfonyl, alkylsulfoxyl, alkylcarbonyl, alkoxycarbonyl, aminocarbonyl, alkylaminocarbonyl, dialkylaminocarbonyl, and in formula III: $Y^7$ and $Y^8$ is $CR^{14}$, $NR^{15}$, O or S, and $Y^9$ and $Y^{10}$ are $CR^{14}$ or $NR^{15}$; $R^{14}$ is hydrogen, alkyl, haloalkyl, halogen, nitrilo, amino, nitro, alkylsulfonyl, alkysulfoxyl, alkylcarbonyl, alkoxycarbonyl, aminocarbonyl, alkylaminocarbonyl or dialkylaminiocarbonyl.

In another embodiment $R^1$ is hydrogen, chloro, propenyl, methylcarbonyl, methoxycarbonyl, propynyl, $SF_5$, thiophenyl, imidazolyl, phenyl, furanyl, C1-C4 alkyl ("Cx-Cy" has the same meaning as "$C_x$-$C_y$"), C1-C2 alkoxy, C1-C2 alkylthio, C1-C2 alkoxy-C1-C2 alkyl, C1-C2 alkylthio-C1-C2 alkyl, each carbon containing radical optionally is substituted by one or more fluorine atoms; $R^2$ is hydrogen, chloro or C1-C2 alkyl; $R^3$ is hydrogen or C1-C2 alkyl; $R^8$ is hydrogen or C1-C2 alkyl, preferably $R^8$ is hydrogen; $R^9$ is hydrogen or C1-C2 alkyl, preferably $R^9$ is hydrogen, and in formula II: one of $Y^1$, $Y^2$, $Y^4$ and $Y^5$ is N; $R^{12}$ is hydrogen, C1-C2 alkyl, C1-C2 alkoxy or C1-C2 alkylthio; $R^{13}$ is hydrogen, C1-C2 alkyl, C1-C2 alkoxy or C1-C2 alkylthio and in formula III: $R^{14}$ is hydrogen, C1-C2 alkyl, C1-C2 alkoxy or C1-C2 alkylthio and $R^{15}$ is missing, methyl or ethyl.

In yet another embodiment $R^1$ is hydrogen or C1-C4 alkyl, preferably C1-C2 alkyl, optionally substituted by one or more fluorine atoms; $R^2$ is hydrogen; $R^3$ is hydrogen; X is CO; at least one of B and D is N; m, n are 1 or 2, and in formula II: $Y^1$ and/or $Y^2$ is N and $Y^4$ and $Y^5$ are $CR^{12}$; $R^{12}$ is hydrogen, methyl or methoxy; $R^{13}$ is hydrogen, methyl or methoxy and in formula III: $R^{14}$ is hydrogen or methyl and $R^{15}$ is missing.

In still another embodiment, if B is N and D is C then E is a bond and G is N, and if B is C and D is N then E is N and G is a bond.

In another embodiment $R^1$ is C1-C2 alkyl optionally substituted by one or more fluorine atoms; B is N; D is N; E, G are bonds; m, n are 2 and A is a monocyclic ring system.

In another embodiment A is a pyridine, thiazole, oxadiazole, thiophene, pyridazine, pyrazine, pyrimidine, imidazole, benzimidazole or a quinoline. Preferably A is a pyridine, thiazole, oxadiazole or a thiophene.

In a preferred embodiment the compound for treating a helminth infection of an animal has the structure of formula (IV), and pharmaceutically acceptable solvates, N-oxides, salts and prodrugs thereof,

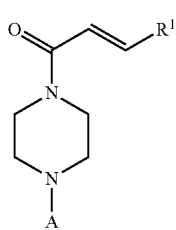

Formula (IV)

wherein
$R^1$ is hydrogen, halogen, alkyl, alkoxy, alkenyl, alkynyl, alkylthio, alkoxyalkyl, alkylthioalkyl, alkylcarbonyl, alkylsulfonyl, $SF_5$, alkoxycarbonyl, phenyl, thiophenyl, furanyl, imidazolyl wherein each of the carbon-containing radicals optionally is substituted by one or more halogen atoms, preferably fluorine atoms, and
in formula II:
$Y^1, Y^2, Y^4$ and $Y^5$ may be N or $CR^{12}$, wherein at least one and at most three of $Y^1, Y^2, Y^4$ and $Y^5$ is N,
$Y^3$ is $CR^{13}$,
$R^{12}$ is hydrogen, alkyl, alkoxy, alkylthio, halogen, nitrilo, nitro, alkylcarbonyl, alkoxycarbonyl, aminocarbonyl, alkylaminocarbonyl, dialkylaminocarbonyl, aminosulfonyl, alkylsulfonyl, alkylsulfoxyl, amino, alkylamino, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms,
$R^{13}$ is hydrogen, alkyl, alkoxy, alkylthio, halogen, nitrilo, nitro, alkylcarbonyl, alkoxycarbonyl, aminocarbonyl, alkylaminocarbonyl, dialkylaminocarbonyl, aminosulfonyl, alkylsulfonyl, alkylsulfoxyl, amino, alkylamino, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms,
$Y^1$ and $Y^2$ may form a ring system or $Y^2$ and $Y^3$ may form a ring system or $Y^3$ and $Y^4$ may form a ring system or $Y^4$ and $Y^5$ may form a ring system,
and in formula III:
$Y^6$ is N or C,
$Y^7, Y^8, Y^9$ and $Y^{10}$ is $CR^{14}$, $NR^{15}$, O, S
$R^{14}$ is hydrogen, alkyl, alkoxy, alkylthio, halogen, nitrilo, nitro, alkylcarbonyl, alkoxycarbonyl, aminocarbonyl, alkylaminocarbonyl, dialkylaminocarbonyl, aminosulfonyl, alkylsulfonyl, alkylsulfoxyl, amino, alkylamino, dialkylamino, N-pyrrolidinyl, N-piperidinyl, N-morpholinyl, alkylcarbonylamino, phenyl, wherein each of the carbon-containing radicals optionally is substituted by one or more halogen atoms, preferably fluorine atoms,
$R^{15}$ is hydrogen, alkyl or missing,
at least one of $Y^7, Y^8, Y^9$ and $Y^{10}$ is N, O or S,
$Y^7$ and $Y^8$ may form a ring system or $Y^8$ and $Y^9$ may form a ring system or $Y^9$ and $Y^{10}$ may form a ring system.

In a further embodiment of this compound $R^1$ is hydrogen, halogen, alkyl, haloalkyl, alkoxy, alkylthio, alkenyl, alkylcarbonyl, alkoxycarbonyl, alkinyl, alkylthioalkyl, alkoxyalkyl, $SF_5$, thiophenyl, imidazolyl, phenyl, furanyl wherein each of the carbon-containing radicals optionally is substituted by one or more halogen atoms, preferably fluorine atoms. Preferably $R^1$ is hydrogen, chloro, propenyl, methylcarbonyl, methoxycarbonyl, propynyl, $SF_5$, thiophenyl, imidazolyl, phenyl, furanyl, C1-C4 alkyl, C1-C2 alkoxy, C1-C2 alkylthio, C1-C2 alkoxy-C1-C2 alkyl, C1-C2 alkylthio-C1-C2 alkyl, each carbon containing radical optionally is substituted by one or more fluorine atoms. More preferably $R^1$ is C1-C4 alkyl optionally substituted by one or more fluorine atoms, further preferred is that $R^1$ is C1-C2 alkyl optionally substituted by one or more fluorine atoms.

With regard to the heteroaryl rest, preferably in formula II one or two of $Y^1, Y^2, Y^4$ and $Y^5$ are N; $R^{12}$ is hydrogen, alkyl, alkoxy, alkylthio, haloalkyl, haloalkoxy, haloalkylthio, halogen, nitrilo, amino, nitro, alkylsulfonyl, alkylsulfoxyl, alkylcarbonyl, alkoxycarbonyl, aminocarbonyl, alkylaminocarbonyl, dialkylaminocarbonyl, and $R^{13}$ is hydrogen, alkyl, alkylthio, haloalkyl, haloalkoxy, haloalkylthio, halogen, nitrilo, amino, nitro, alkylsulfonyl, alkylsulfoxyl, alkylcarbonyl, alkoxycarbonyl, aminocarbonyl, alkylaminocarbonyl, dialkylaminocarbonyl; whereas in formula III $Y^7$ and $Y^8$ is $CR^{14}$, $NR^{15}$, O or S, and $Y^9$ and $Y^{10}$ are $CR^{14}$ or $NR^{15}$; and $R^{14}$ is hydrogen, alkyl, haloalkyl, halogen, nitrilo, amino, nitro, methylsulfonyl, alkylcarbonyl, alkoxycarbonyl, aminocarbonyl, alkylaminocarbonyl or dialkylaminiocarbonyl.

Preferably in formula II one of $Y^1, Y^2, Y^4$ and $Y^5$ is N; $R^{12}$ is hydrogen, C1-C2 alkyl, C1-C2 alkoxy or C1-C2 alkylthio, and $R^{13}$ is hydrogen, C1-C2 alkyl, C1-C2 alkoxy or C1-C2 alkylthio and in formula III $R^{14}$ is hydrogen, C1-C2 alkyl, C1-C2 alkoxy or C1-C2 alkylthio and $R^{15}$ is missing, methyl or ethyl. More preferably in formula II $Y^1$ and/or $Y^2$ is N and $Y^4$ and $Y^5$ are $CR^{12}$; $R^{12}$ is hydrogen, methyl or methoxy, $R^{13}$ is hydrogen and in formula III $R^{14}$ is hydrogen or methyl and $R^{15}$ is missing.

In another embodiment of this particular compound A is a pyridine, thiazole, oxadiazole, thiophene, pyridazine, pyrazine, pyrimidine, benzimidazole or a quinoline. Preferably A is a pyridine, thiazole, oxadiazole or a thiophene.

In another embodiment of any of the compounds according to the invention A is a monocyclic or bicyclic ring system.

In yet another embodiment of any compound according to the invention, in formula II $Y^4$ and $Y^5$ are $CR^{12}$.

The invention is also embodied in the use of a compound according to the invention for the manufacture of a medicament for the treatment of a helminth infection of an animal. Also, the invention is embodied in an anthelmintic composition, wherein the composition comprises one or more compounds according to the invention and one or more pharmaceutically acceptable excipients and/or one or more pharmaceutically acceptable active ingredients which differ from the said one or more compounds according to the invention. The invention is also embodied in the use of such an anthelmintic composition for the treatment of a helminth infection of an animal, and in a kit which comprises as a component a) one or more compounds according to the invention, and as a component b) one or more other components selected from the group consisting of an excipient, an active ingredient, an apparatus for combining the compound of component a) with an excipient and/or active ingredient, an apparatus for administering the compound of component a) to an animal, and a diagnostic tool.

a) Salts, Solvates, N-Oxides and Prodrugs

A salt of the compounds according to the invention may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e. to an animal) for a therapeutic benefit, the salt is pharmaceutically acceptable.

Salts may also be of advantage in the synthesis of the compounds according to this invention. For instance certain intermediates may advantageously be used in form of their salts in the preparation process of the compounds according to this invention.

In general, an acid addition salt can be prepared by reacting a free base compound with an approximately stoichiometric amount of an inorganic or organic acid. Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

A solvate of a compound according to the invention may be formed by aggregation of said compound according to the invention with solvent molecules such as water, alcohols, for example ethanol, aromatic solvents such as toluene, ethers, halogenated organic solvents such as dichloromethane, preferably in a definite proportion by weight.

An N oxide of a compound according to the invention may be formed by oxidation of an N-atom in an amine or N-heterocycle such as pyridine by oxidation agents such as hydrogen peroxide, peracids or inorganic oxidation agents such as potassium peroxymonosulfate (oxone). In preferred N-oxides a nitrogen atom in the group of formula II or III is oxidized, more preferred are N-oxides wherein the nitrogen atom in the group of formula II oxidized giving, for example, a pyridine N-oxide, if one $Y^1$, $Y^2$, $Y^3$ or $Y^4$ is N.

This invention also encompasses prodrug derivatives of the compounds according to the invention. The term prodrug refers to compounds that are transformed in vivo to yield the parent compound of a compound according to the invention. In vivo means that in the case of, for example, treatment of a parasitic infection this transformation can occur in the host organism and/or the parasite. Various forms of prodrugs are well known in the art. For example, if the group of formula (A) represents a pyridine, it is possible to form pyridinium salts such as, for example, acyloxyalkylpyridinium salts, which can offer advantages in terms of higher solubility for parenteral dosage forms, which are described in S. K. Davidsen et al., *J. of Med. Chem.* 37 4423-4429 (1994). Other examples of possible prodrugs are compounds that form the double bond present in formula (I) and (V) by elimination from a saturated precursor compound:

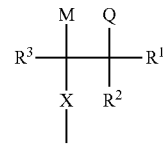

Elimination of MQ will generate compounds of formula (I) or (V). If M is hydrogen, this type of elimination is also known in the art as retro-Michael reaction or retro-Michael addition. Examples of such retro-Michael reactions that occur in vivo to generate unsaturated compounds are described in, for example, S. C. Alley, *Bioconjugate Chem.* 19, 759-765 (2008); D. Lopez, *Abstracts of Papers,* 231st National Meeting, Atlanta, Ga., United States, Mar. 26-30, 2006, MEDI-292.

b) Isomers

The compounds according to this invention and their intermediates may exist in various isomeric forms. A reference to a compound according to this invention or an intermediate thereof always includes all possible isomeric forms of such compound.

In some embodiments, a compound according to this invention may have two or more isomers, such as optical isomers or conformational isomers. For example, the compounds can have a (E) or (Z) configuration at the —$CXR^3$=$CR^1R^2$ double bond. In some preferred embodiments, such compound has the (E) configuration, in other embodiments, the compound has the (Z) configuration. In a preferred embodiment the compounds have (E) configuration. For instance the compounds of formula (V) and the compounds of Tables B, C, D, E and most of the compounds of table A below exhibit (E) configuration.

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Treatment Methods Using Compounds According to this Invention

The compounds according to the invention and pharmaceutically acceptable solvates, N-oxides, salts and prodrugs thereof are for use as a medicament for animals. In some embodiments of this invention, one or more, preferably one compound according to this invention is administered to treat infections, in particular a helminth infection of an animal. In one embodiment one or more, preferably one compound according to this invention is administered to treat parasitoses of an animal.

The term "(parasitic) infection" includes conditions associated with or caused by one or more (parasitic) pathogens; said conditions include clinical conditions (parasitoses) and sub-clinical conditions. The term "treatment of parasitic infection" thus includes both the treatment of parasitoses and the treatment of sub-clinical conditions. The treatment of a parasite infection generally implies the suppression of parasite (e.g. helminth) burdens in the animal below that level at which economic loss occurs.

Sub-clinical conditions are typically conditions not directly leading to clinical symptoms in the parasite infected animal but leading to economic losses. Such economic losses can be e.g. by depression of growth in young animals, lower feed efficiency, lower weight gain in meat producing animals, lower milk production in ruminants, lower egg production in laying hens, or lower wool-production in sheep.

The term "parasitoses" relates to clinically manifest pathologic conditions and diseases associated with or caused by an infection by one or more parasites, such as, for example parasitic gastroenteritis or anemia in ruminants e.g. sheep and goats or colic in horses.

In general, the prevention or treatment of parasitic infection including parasitoses is achieved by administering one or more, preferably one compound according to this invention to treat a parasitic infection such as a helminth infection.

Thus the invention provides a method of treating a (parasitic) infection such as a helminth infection, including parasitoses, which comprises administering to the animal an antiparasitically, preferably an anthelmintically, effective amount of one or more compounds according to this invention. Preferably nematode, cestode or trematode infections are treated, more preferably nematode infections.

"Treating (parasitic) infections" includes treating parasitoses and means to partially or completely inhibit the development of (parasitic) infections of an animal susceptible to (parasitic) infection, reduce or completely eliminate the symptoms of infections of an animal having infections, and/or partially or completely cure infections of an animal having infections. This can be achieved by alleviating or reducing pathogen numbers such as parasite numbers in an animal.

The effect of the compounds according to this invention can be e.g. ovicidal, larvicidal, and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate. Alternatively the parasite is not killed but paralyzed and is then dislodged and excreted by the host animal.

In another aspect the present invention thus provides a pharmaceutical composition comprising an anthelmintically effective amount of one or more, preferably one compound according to this invention and one or more pharmaceutically acceptable excipients.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound e.g. the parasite count is reduced, after a first administration, by an amount ranging from 5% to about 100%.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

A single administration of a compound according to this invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound according to this invention is orally administered, the total dose to treat a disease such as a helminth infection is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention is administered parenterally via an injection, the concentration of the compound according to this invention in the dosage form preferably is sufficient to provide the desired therapeutically effective amount of the compound according to this invention in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

In a preferred embodiment the compounds according to this invention are used to treat a helminth infection caused by one or more helminths selected from the group consisting of a) cestodes: e.g. *Anaplocephala* spp.; *Dipylidium* spp.; *Diphyllobothrium* spp.; *Echinococcus* spp.; *Moniezia* spp.; *Taenia* spp.; b) trematodes e.g. *Dicrocoelium* spp.; *Fasciola* spp.; *Paramphistomum* spp.; *Schistosoma* spp.; or c) nematodes, e.g.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., and/or *Wuchereria* spp.;

It is contemplated that the compounds according to this invention may be used to treat animals, including humans and non-human animals, especially non-human mammals. Such non-human mammals include, for example, livestock mammals (e.g., swine, livestock ruminats like bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). It is contemplated that the compounds according to this invention also are suitable to treat non-mammals, such as poultry (e.g., turkeys, chickens, ducks, etc.) and fish (e.g., salmon, trout, koi, etc.).

In some embodiments, one or more, preferably one compound according to this invention is used to treat an infection by a helminth, such as a nematode, cestode or trematode, preferably a nematode (such as *Haemonchus contortus*), that is resistant to one or more other anthelmintic agents. In some embodiments, the compound according to this invention is active against a helminth, such as a nematode, cestode or trematode, preferably a nematode such as *Haemonchus contortus*, that is resistant to one or more of the following anthelmintics: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzoenedisulphonamide (e.g., clorsulon); a pyrazinaisoquinoline (e.g., praziquantel and epsiprantel); a heterocyclic compound (e.g., piperazine, diethylcarbamazine, dichlorophen, and phenothiazine); an arsenical (e.g., thiacetarsamide, melorsamine, and arsenamide); cyclooctadepsipeptide (e.g., emodepside); and a paraherquamide.

In some such embodiments, for example, the compound according to this invention is active against a helminth (for example, *Haemonchus contortus*) resistant to an avermectin, such as ivermectin. In other embodiments, the compound according to this invention is alternatively or additionally active against a helminth (for example, *Haemonchus contortus*) resistant to a benzimidazole derivative, such as fenbendazole. In other embodiments, the compound according to this invention is alternatively or additionally active against a helminth (for example, *Haemonchus contortus*) resistant to levamisole. And, in other embodiments, the compound according to this invention is alternatively or additionally active against a helminth (for example, *Haemonchus contortus*) resistant to pyrantel.

The compounds according to this invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

The formulation type chosen for a dosage form in any instance will depend upon the particular purpose envisaged and the physical, chemical and biological properties of the compound according to this invention.

Dosage forms useful in the current invention can be liquid, semi-solid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is reconstituted as a solution or as a suspension immediately prior to injection. The principal advantage of this dosage form is that it overcomes the problem of instability in solution or suspension.

One possible dosage route is the oral dosage route, wherein the compound according to this invention is administered via the mouth. Oral dosage forms suitable for oral administration comprise liquids (e.g. drench or drinking water formulations), semi-solids (e.g. pastes, gels), and solids (e.g. tablets, capsules, powders, granules, chewable treats, premixes and medicated blocks).

A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a liquid or solid carrier. This "premix" is, in turn, dispersed in the animal's feed using, for example, a conventional mixer.

Several modified-release delivery systems have been developed, that take advantage of the unique anatomy of the ruminant forestomach, i.e. for intra-ruminal administration. An intraruminal bolus is a specific formulation for ruminants (cattle, sheep, goats, buffalos, camelids, deer etc). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to this invention may alternatively be administered via non-oral dosage routes, such as topically (e.g., via a spot-on, pour-on or transdermal patch), or parenterally (e.g., subcutaneous injection, intravenous injection, intramuscular injection, etc.).

For instance the compounds according to this invention may be administered topically using a transdermal formulation (i.e. a formulation that passes through the skin). Alternatively the compounds according to this invention may be administered topically via the mucosa.

Topical dosage forms suitable for topical administration comprise liquids (e.g. bath, spray, spot-on), semi-solids (e.g. creams, gels), and solids (e.g. patches, powders, collars). Typical topical formulations for animals are liquid or semi-liquid dosage forms. Typical formulations for transdermal and mucosal administration include, for example, pour-ons, spot-ons, dips, sprays, mousses, shampoos, powders, gels, hydrogels, lotions, solutions, creams, ointments, dusting powders, dressings, foams, films, skin patches, limb bands, collars, ear tags, wafers, sponges, fibers, bandages, and microemulsions. When a liquid formulation is used topically on skin, it can be administered by, for example, pouring on (pour-on or spot-on), spreading, rubbing, atomizing, spraying, dipping, bathing, or washing.

The pour-on or spot-on methods, for example, comprise applying the formulation to a specific location of the skin or coat, such as on the neck or backbone of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound according to this invention is dispersed from the application site to wide areas of the fur due to the spreading nature of the components in the formulation and the animal's movements while, in parallel, being absorbed through the skin and distributed via the animal recipient's fluids and/or tissues.

Parenteral formulations and delivery systems for non-oral routes comprise liquids (e.g. solutions, suspensions, emulsions, and dry powders for reconstitution), semi-solids and solids (e.g. implants). The majority of implants that are used in veterinary medicine are compressed tablets or dispersed matrix systems in which the drug is uniformly dispersed within a nondegradable polymer or alternatively extrusion products.

Pharmaceutical Compositions

This invention also is directed to pharmaceutical compositions (or medicaments) comprising one or more, preferably one compound according to this invention. The compositions also may (and preferably will) comprise one or more pharmaceutically acceptable excipients.

Pharmaceutical compositions of the present invention may be manufactured by, for example, processes known in the art. These processes include, for example, a variety of known mixing, dissolving, granulating, emulsifying, encapsulating, entrapping, and lyophilizing processes. Optimal formulation depends on, for example, the dosage route (e.g. oral, injection, topical).

Solid dosage forms, for example, may be prepared by, for example, intimately and uniformly mixing the compounds with fillers, binders, lubricants, glidants, disintegrants, flavoring agents (e.g., sweeteners), buffers, preservatives, pharmaceutical-grade dyes or pigments, and controlled release agents.

Oral dosage forms other than solids may be prepared by mixing the compounds with, for example, one or more solvents, viscosity-enhancing agents, surfactants, preservatives, stabilizers, resins, fillers, binders, lubricants, glidants, disintegrants, co-solvents, sweeteners, flavorings, perfuming agents, buffers, suspending agents, and pharmaceutical-grade dyes or pigments.

Contemplated binders include, for example, gelatin, acacia, and carboxymethyl cellulose.

Contemplated lubricants include, for example, magnesium stearate, stearic acid, and talc.

Contemplated disintegrants include, for example, corn starch, alginic acid, sodium carboxymethylcellulose, and sodium croscarmellose.

Contemplated buffers include, for example, sodium citrate, and magnesium and calcium carbonate and bicarbonate.

Contemplated solvents include, for example, water, petroleum, animal oils, vegetable oils, mineral oil, and synthetic oil. Physiological saline solution or glycols (e.g., ethylene glycol, propylene glycol, or polyethylene glycol) also may be included. The solvent preferably has sufficient chemical properties and quantity to keep the compounds solubilized at temperatures in which the composition is stored and used.

Contemplated viscosity-enhancing agents include, for example, polyethylene, methylcellulose, sodium carboxymethylcellulose, hydroxypropyl-methylcellulose, hydroxypropylcellulose, sodium alginate, carbomer, povidone, acacia, guar gum, xanthan gum, tragacanth, methylcellulose, carbomer, xanthan gum, guar gum, povidone, sodium carboxymethylcellulose, magnesium aluminum silicate, carboxyvinyl polymers, carrageenan, hydroxyethyl cellulose, laponite, water-soluble salts of cellulose ethers, natural gums, colloidal magnesium aluminum silicate or finely divided silica, homopolymers of acrylic acid crosslinked with an alkyl ether of pentaerythritol or an alkyl ether of sucrose, and carbomers.

Contemplated surfactants include, for example, polyoxyethylene sorbitan fatty acid esters; polyoxyethylene monoalkyl ethers; sucrose monoesters; lanolin esters and ethers; alkyl sulfate salts; and sodium, potassium, and ammonium salts of fatty acids.

Contemplated preservatives include, for example, phenol, alkyl esters of parahydroxybenzoic acid (e.g., methyl p-hydroxybenzoate (or "methylparaben") and propyl p-hydroxybenzoate (or "propylparaben")), sorbic acid, o-phenylphenol benzoic acid and the salts thereof, chlorobutanol, benzyl alcohol, thimerosal, phenylmercuric acetate and nitrate, nitromersol, benzalkonium chloride, and cetylpyridinium chloride.

Contemplated stabilizers include, for example, chelating agents and antioxidants.

Solid dosage forms also may comprise, for example, one or more excipients to control the release of the compounds. For example, it is contemplated that the compounds may be dispersed in, for example, hydroxypropylmethyl cellulose. Some oral dosage forms (e.g., tablets and pills) also may be prepared with enteric coatings.

Topical dosage route uses, for example, a concentrated liquid or semi-liquid solution, suspension (aqueous or non-aqueous), emulsion (water-in-oil or oil-in-water), or microemulsion comprising a compounds dissolved, suspended, or emulgated in a pharmaceutically-acceptable liquid vehicle. In such embodiments, a crystallization inhibitor optionally may generally be present.

Such a pour-on or spot-on formulation can be prepared by dissolving, suspending, or emulsifying the compounds in a suitable skin-fitted solvent or solvent mixture. Other excipients may be included as well, such as, for example, a surfactant, colorant, antioxidant, stabilizer, adhesive, etc. Contemplated solvents include, for example, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oil, DMF, liquid paraffin, silicone, dimethylacetamide, N-methylpyrrolidone, or 2,2-dimethyl-4-oxy-methylene-1,3-dioxolane.

In some embodiments, a topical formulation (particularly a pour-on or spot-on formulation) comprises a carrier that promotes the absorption or penetration of the compounds through the skin into the blood stream, other bodily fluids (lymph), and/or body tissue (fat tissue). Contemplated examples of dermal penetration enhancers include, for example, dimethylsulfoxide, isopropyl myristate, dipropylene glycol pelargonate, silicone oil, aliphatic esters, triglycerides, and fatty alcohols.

Topical formulations also (or alternatively) may comprise, for example, one or more spreading agents. These substances act as carriers that assist in distributing an active ingredient over the animal recipient's coat or skin. They may include, for example, isopropyl myristate, dipropylene glycol pelargonate, silicone oils, fatty acid esters, triglycerides, and/or fatty alcohols. Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the formulation comprises a spreading agent, it also may be advantageous to include a dispersant, such as, for example, pyrrolidin-2-one, N-alkylpyrrolidin-2-one, acetone, polyethylene glycol or ether or ester thereof, propylene glycol, or synthetic triglycerides.

When formulated in, for example, an ointment, it is contemplated that the compounds may be mixed with, for example, either a paraffinic or a water-miscible ointment base. When formulated in a cream, it is contemplated that the compounds may be formulated with, for example, an oil-in-water cream base. In some instances, the aqueous phase of the cream base includes, for example at least about 30% (w/w) of a polyhydric alcohol, such as propylene glycol, butane-1,3-diol, mannitol, sorbitol, glycerol, polyethylene glycol, or a mixture thereof.

Injectable formulations may be prepared according to, for example, the known art using suitable solvents, solubilizing agents, protecting agents, dispersing agents, wetting agents, and/or suspending agents. Contemplated carrier materials include, for example, water, ethanol, butanol, benzyl alcohol, glycerin, 1,3-butanediol, Ringer's solution, isotonic sodium chloride solution, bland fixed oils (e.g., synthetic mono- or diglycerides), vegetable oil (e.g., corn oil), dextrose, mannitol, fatty acids (e.g., oleic acid), dimethyl acetamide, surfactants (e.g., ionic and non-ionic detergents), N-methylpyrrolidone, propylene glycol, and/or polyethylene glycols (e.g., PEG 400). Contemplated solubilizing agents include, for example, polyvinyl pyrrolidone, polyoxyethylated castor oil, polyoxyethylated sorbitan ester, and the like. Contemplated protecting agents include, for example, benzyl alcohol, trichlorobutanol, p-hydroxybenzoic acid ester, n-butanol, and the like.

In some embodiments, a parenteral formulation is, for example, prepared from sterile powders or granules having one or more of the carriers materials discussed above for other formulations. The compounds is, for example, dissolved or suspended in a liquid comprising water, polyethylene glycol, propylene glycol, ethanol, corn oil, cottonseed oil, peanut oil, sesame oil, benzyl alcohol, sodium chloride, and/or various buffers. The pH generally may be adjusted, if necessary, with a suitable acid, base, or buffer.

Other inert ingredients may generally be added to the composition as desired. To illustrate, it is contemplated that these may include, for example, lactose, mannitol, sorbitol, calcium carbonate, sodium carbonate, tribasic calcium phosphate, dibasic calcium phosphate, sodium phosphate, kaolin, compressible sugar, starch, calcium sulfate, dextro or microcrystalline cellulose, colloidal silicon dioxide, starch, sodium starch glycolate, crospovidone, microcrystalline cellulose, tragacanth, hydroxypropylcellulose, pregelatinized starch, povidone, ethylcellulose, hydroxypropylcellulose, hydroxypropylmethylcellulose, and methylcellulose.

Further aspects regarding formulation of drugs and various excipients are found in, for example, Gennaro, A. R., et al., eds., *Remington: The Science and Practice of Pharmacy* (Lippincott Williams & Wilkins, 20th Ed., 2000). Another source regarding formulation of drugs and various excipients is found in, for example, Liberman, H. A., et al., eds., *Pharmaceutical Dosage Forms* (Marcel Decker, New York, N.Y., 1980).

The concentration of the compounds according to this invention in the applied dosage form may vary widely depending on, for example, the dosage route. In general, the concentration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

In another aspect the present invention thus provides a pharmaceutical composition comprising an anthelmintically effective amount of one or more, preferably one compound according to this invention and one or more pharmaceutically acceptable excipients.

The formulation type chosen for a dosage form in any instance will depend upon the particular purpose envisaged and the physical, chemical and biological properties of the compound according to this invention.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

A single administration of a compound according to this invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound according to this invention is orally administered, the total dose to treat a disease such as a helminth infection is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention is administered parenterally via an injection, the concentration of the compound according to this invention in the dosage form preferably is sufficient to provide the desired therapeutically effective amount of the compound according to this invention in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

Examples of Contemplated Combination Therapies

The methods and pharmaceutical compositions of this invention encompass methods wherein a compound according to this invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different parasites and conditions.

Contemplated active ingredient(s) that may be administered in combination with the compounds include, for example, pharmaceutically acceptable anthelmintics, insecticides and acaricides, insect growth regulators, anti-inflammatories, anti-infectives, hormones, dermatological preparations (e.g., antiseptics and disinfectants), and immunobiologicals (e.g., vaccines and antisera) for disease prevention.

Therefore this invention is also directed to the use as a medicament of combinations comprising a) one or more compounds according to this invention with b) one or more pharmaceutically acceptable active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); probenzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); and amino-acetonitrile compounds (e.g. monepantel, AAD 1566); tribendimidine (amidine compound); amidine compounds (e.g., amidantel and tribendimidin), including all pharmaceutically acceptable forms, such as salts, solvates or N-oxides.

Preferred combinations are comprising a) one compound selected from the group of compounds A-1 to A-369, B-1 to B-172, C-1 to C-18, D-1 to D-287 and E1 to E-4 of the Tables A, B, C, D and E below (or salts, solvates or N-oxides thereof if applicable) and b) one compound selected from the group consisting of anthelmintic avermectins (e.g., ivermectin, selamectin, doramectin, abamectin, emamectin and eprinomectin); milbemycins (moxidectin and milbemycin oxime); probenzimidazoles (e.g., febantel, netobimin, and thiophanate); benzimidazole derivatives, such as thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidines (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566); tribendimidine (amidine compound); and amidantel (amidine compound); including all pharmaceutically acceptable forms, such as salts.

Preferred combinations comprise at least one compound selected from the group of compounds A-1 to A-370, B-1 to B-172, C-1 to C-18, D-1 to D-287 and E1 to E-4 of the Tables A, B, C, D and E below (or salts, solvates or N-oxides thereof if applicable) and abamectin, ivermectin, emamectin, eprinomectin, doramectin, moxidectin, milbemycin oxime; or closantel, oxyclozanide, rafoxanide, niclosamide; or nitroxynil, nitroscanate, clorsulon; or praziquantel, epsiprantel; or emodepside, derquantel, monepantel.

Examples of such combinations are combinations of one of the compounds A-1 to A-370, B-1 to B-172, C-1 to C-18, D-1 to D-287 and E1 to E-4 of the Tables A, B, C, D and E below with abamectin.

Other examples are combinations of one of the compounds A-1 to A-370, B-1 to B-172, C-1 to C-18, D-1 to D-287 and E1 to E-4 of the Tables A, B, C, D and E below with ivermectin.

Other examples are combinations of one of the compounds A-1 to A-370, B-1 to B-172, C-1 to C-18, D-1 to D-287 and E1 to E-4 of the Tables A, B, C, D and E below with emamectin.

Other examples are combinations of one of the compounds A-1 to A-370, B-1 to B-172, C-1 to C-18, D-1 to D-287 and E1 to E-4 of the Tables A, B, C, D and E below with eprinomectin.

Other examples are combinations of one of the compounds A-1 to A-370, B-1 to B-172, C-1 to C-18, D-1 to D-287 and E1 to E-4 of the Tables A, B, C, D and E below with doramectin.

Other examples are combinations of one of the compounds A-1 to A-370, B-1 to B-172, C-1 to C-18, D-1 to D-287 and E1 to E-4 of the Tables A, B, C, D and E below with moxidectin.

Other examples are combinations of one of the compounds A-1 to A-370, B-1 to B-172, C-1 to C-18, D-1 to D-287 and E1 to E-4 of the Tables A, B, C, D and E below with milbemycin oxime.

Other examples are combinations of one of the compounds A-1 to A-370, B-1 to B-172, C-1 to C-18, D-1 to D-287 and E1 to E-4 of the Tables A, B, C, D and E below with closantel.

Other examples are combinations of one of the compounds A-1 to A-370, B-1 to B-172, C-1 to C-18, D-1 to D-287 and E1 to E-4 of the Tables A, B, C, D and E below with oxyclozanide.

Other examples are combinations of one of the compounds A-1 to A-370, B-1 to B-172, C-1 to C-18, D-1 to D-287 and E1 to E-4 of the Tables A, B, C, D and E below with rafoxanide.

Other examples are combinations of one of the compounds A-1 to A-370, B-1 to B-172, C-1 to C-18, D-1 to D-287 and E1 to E-4 of the Tables A, B, C, D and E below with niclosamide.

Other examples are combinations of one of the compounds A-1 to A-370, B-1 to B-172, C-1 to C-18, D-1 to D-287 and E1 to E-4 of the Tables A, B, C, D and E below with nitroxynil.

Other examples are combinations of one of the compounds A-1 to A-370, B-1 to B-172, C-1 to C-18, D-1 to D-287 and E1 to E-4 of the Tables A, B, C, D and E below with nitroscanate.

Other examples are combinations of one of the compounds A-1 to A-370, B-1 to B-172, C-1 to C-18, D-1 to D-287 and E1 to E-4 of the Tables A, B, C, D and E below with clorsulon.

Other examples are combinations of one of the compounds A-1 to A-370, B-1 to B-172, C-1 to C-18, D-1 to D-287 and E1 to E-4 of the Tables A, B, C, D and E below with praziquantel.

Other examples are combinations of one of the compounds A-1 to A-370, B-1 to B-172, C-1 to C-18, D-1 to D-287 and E1 to E-4 of the Tables A, B, C, D and E below with epsiprantel.

Other examples are combinations of one of the compounds A-1 to A-370, B-1 to B-172, C-1 to C-18, D-1 to D-287 and E1 to E-4 of the Tables A, B, C, D and E below with emodepside.

Other examples are combinations of one of the compounds A-1 to A-370, B-1 to B-172, C-1 to C-18, D-1 to D-287 and E1 to E-4 of the Tables A, B, C, D and E below with derquantel.

Other examples are combinations of one of the compounds A-1 to A-370, B-1 to B-172, C-1 to C-18, D-1 to D-287 and E1 to E-4 of the Tables A, B, C, D and E below with monepantel.

Examples of such combinations are combinations of a salt of one of the compounds A-1 to A-370, B-1 to B-172, C-1 to C-18, D-1 to D-287 and E1 to E-4 of the Tables A, B, C, D and E below with abamectin.

Other examples are combinations of a salt of one of the compounds A-1 to A-370, B-1 to B-172, C-1 to C-18, D-1 to D-287 and E1 to E-4 of the Tables A, B, C, D and E below with ivermectin.

Other examples are combinations of a salt of one of the compounds A-1 to A-370, B-1 to B-172, C-1 to C-18, D-1 to D-287 and E1 to E-4 of the Tables A, B, C, D and E below with emamectin.

Other examples are combinations of a salt of one of the compounds A-1 to A-370, B-1 to B-172, C-1 to C-18, D-1 to D-287 and E1 to E-4 of the Tables A, B, C, D and E below with eprinomectin.

Other examples are combinations of a salt of one of the compounds A-1 to A-370, B-1 to B-172, C-1 to C-18, D-1 to D-287 and E1 to E-4 of the Tables A, B, C, D and E below with doramectin.

Other examples are combinations of a salt of one of the compounds A-1 to A-370, B-1 to B-172, C-1 to C-18, D-1 to D-287 and E1 to E-4 of the Tables A, B, C, D and E below with moxidectin.

Other examples are combinations of a salt of one of the compounds A-1 to A-370, B-1 to B-172, C-1 to C-18, D-1 to D-287 and E1 to E-4 of the Tables A, B, C, D and E below with milbemycin oxime.

Other examples are combinations of a salt of one of the compounds A-1 to A-370, B-1 to B-172, C-1 to C-18, D-1 to D-287 and E1 to E-4 of the Tables A, B, C, D and E below with closantel.

Other examples are combinations of a salt of one of the compounds A-1 to A-370, B-1 to B-172, C-1 to C-18, D-1 to D-287 and E1 to E-4 of the Tables A, B, C, D and E below with oxyclozanide.

Other examples are combinations of a salt of one of the compounds A-1 to A-370, B-1 to B-172, C-1 to C-18, D-1 to D-287 and E1 to E-4 of the Tables A, B, C, D and E below with rafoxanide.

Other examples are combinations of a salt of one of the compounds A-1 to A-370, B-1 to B-172, C-1 to C-18, D-1 to D-287 and E1 to E-4 of the Tables A, B, C, D and E below with niclosamide.

Other examples are combinations of a salt of one of the compounds A-1 to A-370, B-1 to B-172, C-1 to C-18, D-1 to D-287 and E1 to E-4 of the Tables A, B, C, D and E below with nitroxynil.

Other examples are combinations of a salt of one of the compounds A-1 to A-370, B-1 to B-172, C-1 to C-18, D-1 to D-287 and E1 to E-4 of the Tables A, B, C, D and E below with nitroscanate.

Other examples are combinations of a salt of one of the compounds A-1 to A-370, B-1 to B-172, C-1 to C-18, D-1 to D-287 and E1 to E-4 of the Tables A, B, C, D and E below with clorsulon.

Other examples are combinations of a salt of one of the compounds A-1 to A-370, B-1 to B-172, C-1 to C-18, D-1 to D-287 and E1 to E-4 of the Tables A, B, C, D and E below with praziquantel.

Other examples are combinations of a salt of one of the compounds A-1 to A-370, B-1 to B-172, C-1 to C-18, D-1 to D-287 and E1 to E-4 of the Tables A, B, C, D and E below with epsiprantel.

Other examples are combinations of a salt of one of the compounds A-1 to A-370, B-1 to B-172, C-1 to C-18, D-1 to D-287 and E1 to E-4 of the Tables A, B, C, D and E below with emodepside.

Other examples are combinations of a salt of one of the compounds A-1 to A-370, B-1 to B-172, C-1 to C-18, D-1 to D-287 and E1 to E-4 of the Tables A, B, C, D and E below with derquantel.

Other examples are combinations of a salt of one of the compounds A-1 to A-370, B-1 to B-172, C-1 to C-18, D-1 to D-287 and E1 to E-4 of the Tables A, B, C, D and E below with monepantel.

Examples of such combinations are combinations of a solvate of one of the compounds A-1 to A-370, B-1 to B-172, C-1 to C-18, D-1 to D-287 and E1 to E-4 of the Tables A, B, C, D and E below with abamectin.

Other examples are combinations of a solvate of one of the compounds A-1 to A-370, B-1 to B-172, C-1 to C-18, D-1 to D-287 and E1 to E-4 of the Tables A, B, C, D and E below with ivermectin.

Other examples are combinations of a solvate of one of the compounds A-1 to A-370, B-1 to B-172, C-1 to C-18, D-1 to D-287 and E1 to E-4 of the Tables A, B, C, D and E below with emamectin.

Other examples are combinations of a solvate of one of the compounds A-1 to A-370, B-1 to B-172, C-1 to C-18, D-1 to D-287 and E1 to E-4 of the Tables A, B, C, D and E below with eprinomectin.

Other examples are combinations of a solvate of one of the compounds A-1 to A-370, B-1 to B-172, C-1 to C-18, D-1 to D-287 and E1 to E-4 of the Tables A, B, C, D and E below with doramectin.

Other examples are combinations of a solvate of one of the compounds A-1 to A-370, B-1 to B-172, C-1 to C-18, D-1 to D-287 and E1 to E-4 of the Tables A, B, C, D and E below with moxidectin.

Other examples are combinations of a solvate of one of the compounds A-1 to A-370, B-1 to B-172, C-1 to C-18, D-1 to D-287 and E1 to E-4 of the Tables A, B, C, D and E below with milbemycin oxime.

Other examples are combinations of a solvate of one of the compounds A-1 to A-370, B-1 to B-172, C-1 to C-18, D-1 to D-287 and E1 to E-4 of the Tables A, B, C, D and E below with closantel.

Other examples are combinations of a solvate of one of the compounds A-1 to A-370, B-1 to B-172, C-1 to C-18, D-1 to D-287 and E1 to E-4 of the Tables A, B, C, D and E below with oxyclozanide.

Other examples are combinations of a solvate of one of the compounds A-1 to A-370, B-1 to B-172, C-1 to C-18, D-1 to D-287 and E1 to E-4 of the Tables A, B, C, D and E below with rafoxanide.

Other examples are combinations of a solvate of one of the compounds A-1 to A-370, B-1 to B-172, C-1 to C-18, D-1 to D-287 and E1 to E-4 of the Tables A, B, C, D and E below with niclosamide.

Other examples are combinations of a solvate of one of the compounds A-1 to A-370, B-1 to B-172, C-1 to C-18, D-1 to D-287 and E1 to E-4 of the Tables A, B, C, D and E below with nitroxynil.

Other examples are combinations of a solvate of one of the compounds A-1 to A-370, B-1 to B-172, C-1 to C-18, D-1 to D-287 and E1 to E-4 of the Tables A, B, C, D and E below with nitroscanate.

Other examples are combinations of a solvate of one of the compounds A-1 to A-370, B-1 to B-172, C-1 to C-18, D-1 to D-287 and E1 to E-4 of the Tables A, B, C, D and E below with clorsulon.

Other examples are combinations of a solvate of one of the compounds A-1 to A-370, B-1 to B-172, C-1 to C-18, D-1 to D-287 and E1 to E-4 of the Tables A, B, C, D and E below with praziquantel.

Other examples are combinations of a solvate of one of the compounds A-1 to A-370, B-1 to B-172, C-1 to C-18, D-1 to D-287 and E1 to E-4 of the Tables A, B, C, D and E below with epsiprantel.

Other examples are combinations of a solvate of one of the compounds A-1 to A-370, B-1 to B-172, C-1 to C-18, D-1 to D-287 and E1 to E-4 of the Tables A, B, C, D and E below with emodepside.

Other examples are combinations of a solvate of one of the compounds A-1 to A-370, B-1 to B-172, C-1 to C-18, D-1 to D-287 and E1 to E-4 of the Tables A, B, C, D and E below with derquantel.

Other examples are combinations of a solvate of one of the compounds A-1 to A-370, B-1 to B-172, C-1 to C-18, D-1 to D-287 and E1 to E-4 of the Tables A, B, C, D and E below with monepantel.

Examples of such combinations are combinations of an N-oxide of one of the compounds A-1 to A-370, B-1 to B-172, C-1 to C-18, D-1 to D-287 and E1 to E-4 of the Tables A, B, C, D and E below with abamectin.

Other examples are combinations of an N-oxide of one of the compounds A-1 to A-370, B-1 to B-172, C-1 to C-18, D-1 to D-287 of the Tables A, B, C and D below with ivermectin.

Other examples are combinations of an N-oxide of one of the compounds A-1 to A-370, B-1 to B-172, C-1 to C-18, D-1 to D-287 and E1 to E-4 of the Tables A, B, C and D below with emamectin.

Other examples are combinations of an N-oxide of one of the compounds A-1 to A-370, B-1 to B-172, C-1 to C-18, D-1 to D-287 and E1 to E-4 of the Tables A, B, C and D below with eprinomectin.

Other examples are combinations of an N-oxide of one of the compounds A-1 to A-370, B-1 to B-172, C-1 to C-18, D-1 to D-287 of the Tables A, B, C and D below with doramectin.

Other examples are combinations of an N-oxide of one of the compounds A-1 to A-370, B-1 to B-172, C-1 to C-18, D-1 to D-287 of the Tables A, B, C and D below with moxidectin.

Other examples are combinations of an N-oxide of one of the compounds A-1 to A-370, B-1 to B-172, C-1 to C-18, D-1 to D-287 of the Tables A, B, C and D below with milbemycin oxime.

Other examples are combinations of an N-oxide of one of the compounds A-1 to A-370, B-1 to B-172, C-1 to C-18, D-1 to D-287 of the Tables A, B, C and D below with closantel.

Other examples are combinations of an N-oxide of one of the compounds A-1 to A-370, B-1 to B-172, C-1 to C-18, D-1 to D-287 of the Tables A, B, C and D below with oxyclozanide.

Other examples are combinations of an N-oxide of one of the compounds A-1 to A-370, B-1 to B-172, C-1 to C-18, D-1 to D-287 of the Tables A, B, C and D below with rafoxanide.

Other examples are combinations of an N-oxide of one of the compounds A-1 to A-370, B-1 to B-172, C-1 to C-18, D-1 to D-287 of the Tables A, B, C and D below with niclosamide.

Other examples are combinations of an N-oxide of one of the compounds A-1 to A-370, B-1 to B-172, C-1 to C-18, D-1 to D-287 of the Tables A, B, C and D below with nitroxynil.

Other examples are combinations of an N-oxide of one of the compounds A-1 to A-370, B-1 to B-172, C-1 to C-18, D-1 to D-287 of the Tables A, B, C and D below with nitroscanate.

Other examples are combinations of an N-oxide of one of the compounds A-1 to A-370, B-1 to B-172, C-1 to C-18, D-1 to D-287 of the Tables A, B, C and D below with clorsulon.

Other examples are combinations of an N-oxide of one of the compounds A-1 to A-370, B-1 to B-172, C-1 to C-18, D-1 to D-287 of the Tables A, B, C and D below with praziquantel.

Other examples are combinations of an N-oxide of one of the compounds A-1 to A-370, B-1 to B-172, C-1 to C-18, D-1 to D-287 of the Tables A, B, C and D below with epsiprantel.

Other examples are combinations of an N-oxide of one of the compounds A-1 to A-370, B-1 to B-172, C-1 to C-18, D-1 to D-287 of the Tables A, B, C and D below with emodepside.

Other examples are combinations of an N-oxide of one of the compounds A-1 to A-370, B-1 to B-172, C-1 to C-18, D-1 to D-287 of the Tables A, B, C and D below with derquantel.

Other examples are combinations of an N-oxide of one of the compounds A-1 to A-370, B-1 to B-172, C-1 to C-18, D-1 to D-287 of the Tables A, B, C and D below with monepantel.

The compounds of the current invention can be combined with pharmaceutically acceptable insecticides or acaricides. Such pharmaceutically acceptable insecticides and acaricides include, for example, acetamiprid, acetoprole, amitraz, amidoflumet, avermectin, azadirachtin, bifenthrin, bifenazate, buprofezin, bistrifluoron, chlorfenapyr, chlorfluazuron, chlorantraniliprole, chlorpyrifos, chromafenozide, clothianidin, cyantraniliprole, cyflumetofen, β-cyfluthrin, cyhalothrin, λ-cyhalothrin, cymiazole cypermethrin, cyromazine, deltamethrin, demiditraz, diafenthiuron, diazinon, diflubenzuron, dimefluthrin, dinotefuran, emamectin, esfenvalerate, ethiprole, fenoxycarb, fenpropathrin, fenvalerate, fipronil, flonicamid, flubendiamide, flucythrinate, tau-fluvalinate, flufenoxuron, halofenozide, hexaflumuron, imidacloprid, indoxacarb, lufenuron, metaflumizone, methoprene, metofluthrin, methoxyfenozide, nitenpyram, novaluron, noviflumuron, permethrin, phosmet, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen, spirotetramat, sulfoxaflor, tebufenozide, tebufenpyrad, teflubenzuron, tefluthrin, tetrachlorvinphos, tetramethylfluthrin, thiacloprid, thiamethoxam, tolfenpyrad, tralomethrin, and triflumuron. General references discussing antiparasitic agents, such as insecticides and acaricides, include, for example, *The Pesticide Manual,* 13th Edition, C. D. S. Tomlin, Ed., British Crop Protection Council, Farnham, Surrey, U.K. (2003).

In some contemplated embodiments, the compounds are administered with pyridylmethylamine derivatives, such as, for example, pyridylmethylamine derivatives discussed in European Patent Appl. EP0539588 or Intl Patent Appl. Publ. WO2007/115643.

In some contemplated embodiments, the compounds is administered with nodulisporic acids and derivatives thereof, such as, for example, compounds discussed in U.S. Pat. No. 5,399,582; 5,945,317; 5,962,499; 5,834,260; 6,221,894; or 5,595,991; or Intl Patent Appl. Publ. 1996/29073.

Pharmaceutically acceptable insect growth regulators include, for example, methoprene, pyriproxyfen, tetrahydroazadirachtin, chlorfluazuron, cyromazine, diflubenzuron, fluazuron, flucycloxuron, flufenoxuron, hexaflumuron, lufenuron, ifenuron, tebufenozide, and triflumuron. These compounds tend to provide both initial and sustained treatment of parasite infections at all stages of insect development, including eggs, on the animal subject, as well as within the environment of the animal subject.

Other antiparasitic compounds contemplated to be useful in combination therapies with the compounds include, for example, imidazo[1,2-b]pyridazine compounds discussed in US Patent Appl. Publ. No. 2005-0182059; 1-(4-Mono and di-halomethylsulphonylphenyl)-2-acylamino-3-fluoropropanol compounds discussed U.S. Pat. No. 7,361,689; trifluoromethanesulfonanilide oxime ether compounds discussed in U.S. Pat. No. 7,312,248; n-[(phenyloxy)phenyl]-1,1,1-trifluoromethanesulfonamide and n-[(phenylsulfanyl)phenyl]-1,1,1-trifluoromethanesulfonamide compounds discussed in US Patent Appl. Publ. 2006-0281695; and 2-phenyl-3-(1H-pyrrol-2-yl)acrylonitrile compounds discussed in US Appl. Publ. 2006/0128779; isoxazoline compounds discussed in WO Patent Appl, Publ. 2005-085216, WO 2007-026965, WO 2007-070606, WO 2007-075459, WO 2007-079162, WO 2007-105814, WO 2007-125984, WO 2008-019760, WO 2008-122375, WO 2008-150393, WO 2009-002809, WO 2009-003075, WO 2009-022746, WO 2009-035004, WO 2009-045999, WO 2009-051956, WO 2009-035004.

In the contemplated combination therapies, the compounds according to this invention may be administered before, simultaneously, and/or after the other active ingredient(s). In addition, the compounds according to this invention may be administered in the same composition as the other active ingredient(s) and/or in separate compositions from the other active ingredient(s). Further, the compounds according to this invention and other active ingredient(s) may be administered via the same and/or different dosage route.

When the compounds according to this invention are administered in a combination therapy, the weight ratio of the active ingredients may vary widely. Factors influencing this ratio include, for example, the particular compounds; the identity of the other active ingredient(s) be administered in the combination therapy; the dosage route of the compounds and other active ingredient(s); the target condition and pathogen; the type (e.g., species and breed), age, size, sex, diet, activity, and condition of the animal; and pharmacological considerations, such as the activity, efficacy, pharmacokinetic, and toxicology profiles of the compounds and other active ingredient(s). In some contemplated embodiments, for example, the weight ratio of the compounds to the other active ingredient(s) is, for example, is from about 1:3000 to about 3000:1. In some such instances, the weight ratio is from about 1:300 to about 300:1. In other such instances, the weight ratio is from about 1:30 and about 30:1.

In addition to other active ingredients, it is contemplated that the compounds may be administered with one or more other compounds that beneficially affects (e.g. enhances or prolongs) the activity (or other characteristic, such as safety) of the compounds. For example, it is contemplated that the compounds may be administered with one or more synergists, such as, for example, piperonyl butoxide (PBO) and triphenyl phosphate (TPP). Other synergists include, for example, N-(2-ethylhexyl)-8,9,10-trinorborn-5-ene-2,3-dicarboxamide (also known as "ENT 8184" or "MGK 264") and Verbutin (also known as "MB-599").

This invention also is directed to kits that are, for example, suitable for use in performing the methods of treatment described above. The kit comprises a therapeutically effective amount of one or more compounds of this invention, and an additional component. The additional component(s) may be, for example, one or more of the following: another ingredient (e.g., an excipient or active ingredient), an apparatus for combining the compound of this invention with another ingredient and/or for administering the compound of this invention, or a diagnostic tool.

The compounds used according to this invention show an excellent activity in treating parasite infections and in addition are acceptable for the animals treated.

EXAMPLES

The following examples are merely illustrative, and not limiting to the remainder of the disclosure in any way.

A: General Description of Synthesis of Compounds as Described in this Specification The compounds as described in this specification can be obtained by various synthesis routes. A person skilled in the art will choose the synthetic route to obtain a compound as described in this specification depending on the nature of its radicals as defined in relation to Formula (I). This is illustrated in the following schemes, which are merely illustrative but not limiting the disclosure in any way.

Scheme 1:

route 1a

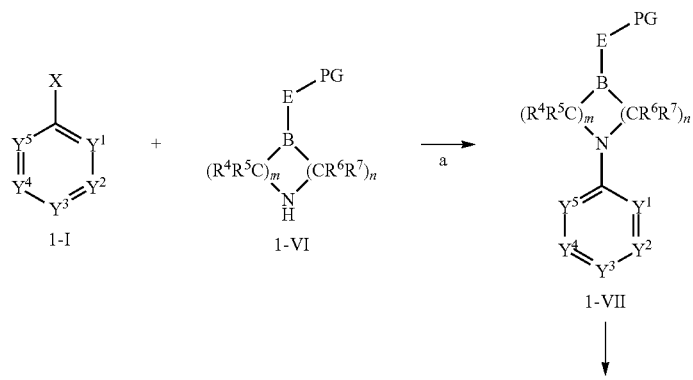

route 1

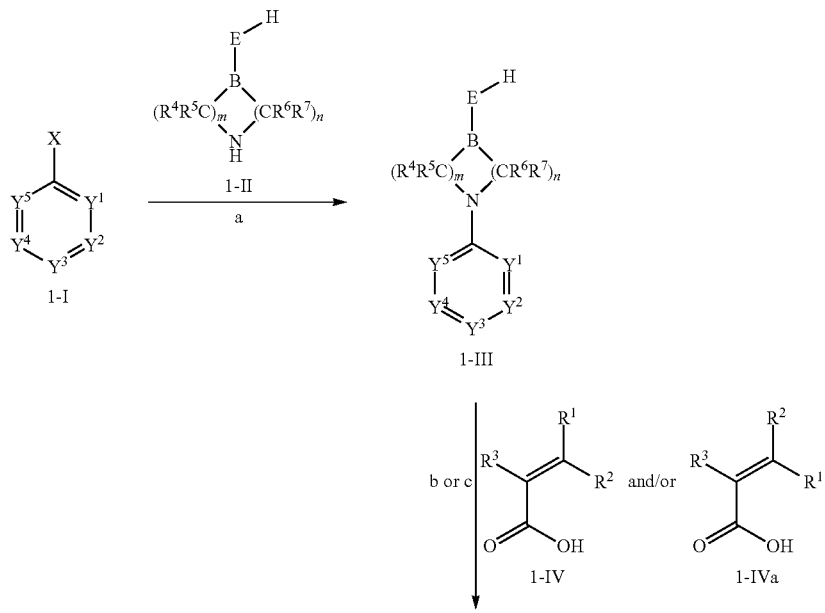

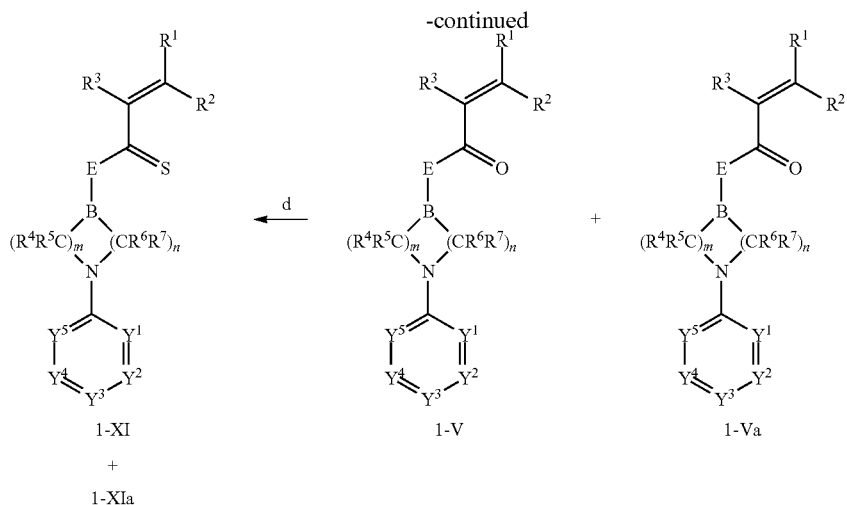

1-XI + 1-XIa route 2

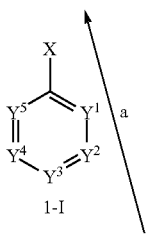

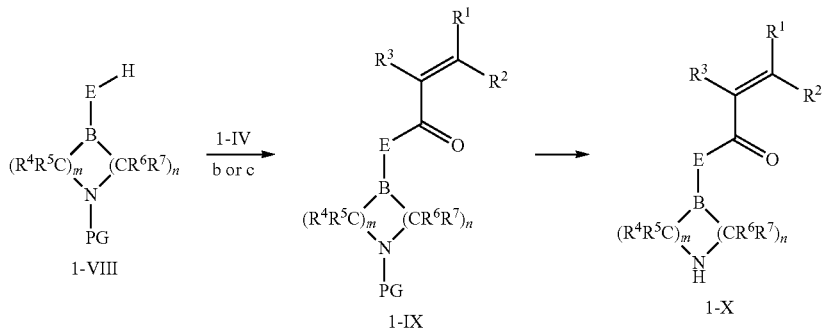

Exemplary conditions: a: palladium acetate, 2,2'-Bis(diphenylphosphino)-1,1'-binaphthyl (BINAP), caesium carbonate, dioxane; b: oxalyl chloride, dichloromethane (DCM), dimethylformamide (DMF) then DCM, triethylamine; c: 1-[bis(dimethylamino)methylene]-1H-1,2,3-triazolo[4,5-b]pyridinium-3-oxide hexafluorophosphate (HATU), diisopropylethylamine, DMF, room temperature; d: Lawesson's reagent, tetrahydrofuran (THF), 130° C.

A compound of general formula 1-V can be synthesized as shown in scheme 1: in route 1 a heteroaryl compound 1-I is reacted with a cyclic diamine 1-II to give 1-III. 1-I contains a suitable leaving group X, which is preferably a halogen like chloro or bromo. The reaction with 1-II is done preferably under Pd-catalysis employing a Pd-containing molecule like palladium acetate or tris(dibenzylideneacetone)dipalladium (0) ($Pd_2(DBA)_3$), a phosphorus-containing ligand like 2-2'-bis(diphenylphosphino)-1,1'-binaphthyl (BINAP) or 2-(dicyclohexylphosphino)-2',6'-di-isopropoxy-1,1'-biphenyl (RuPhos) or 2-(dicyclohexylphosphino)-3,6-dimethoxy-2',4',6'-tri-isopropyl-1,1'biphenyl (BrettPhos), a base like caesium carbonate or sodium tert-butoxide in a solvent like an ether-containing solvent like diethylether, dioxane or tetrahydrofuran, preferably dioxane or an inert solvent like toluene and preferably at elevated temperatures. 1-II is employed preferably in excess. Depending on the nature of 1-I the leaving group X might be displaced by 1-II or 1-VI under conditions for nucleophilic substitutions. For example, if X is a leaving group like halogen or a nitro group and $Y^1$-$Y^5$ are substituted by electron withdrawing substituents, the reaction can be carried out in a solvent like dioxane or, for example, a high boiling solvent like ethyleneglycolmonomethyl ether, optionally with addition of a base like, for example, ethyldiisopropylamine. Or the reaction can be carried out without solvent by using the diamine 1-II in excess with the optional addition of a base like, for example, potassium carbonate. Also if $Y^1$ and/or $Y^4$ in 1-I is a nitrogen, such a nucleophilic substitution reaction can be used.

The diamine can be protected with a suitable protecting group as in 1-VI of route 1a. Suitable protecting groups (PG) for the nitrogen in 1-VI include, but are not limited to, preferably tert-butyl carbamate (Boc), benzyl carbamate (Cbz) and the like. A protected diamine 1-VI can be reacted under the same conditions as 1-II. The protecting group in the intermediate 1-VII can be removed by suitable methods known to a person skilled in the art; if PG is a Boc-group, for example, the protecting group can be removed by an acid like trifluoroacetic acid or hydrochloric acid to give the amine 1-III. Other suitable methods for protection and deprotection are described in, for example, Green and Wuts, *Protective Groups in Organic Synthesis*, 3$^{rd}$ edition, John Wiley & Sons, New York, 1999. 1-III is acylated with an unsaturated acid derivative 1-IV to give the final product 1-V. 1-IV can be accompanied by the isomeric 1-IVa, so that a mixture of 1-IV and 1-IVa is used in the acylation step. In this case a mixture of 1-V and 1-Va is formed that can be separated by methods known to a person skilled in the art, e.g. by chromatography. Or 1-IVa can be used in a pure form in the acylation step to give 1-Va. Thus, if in the following descriptions and schemes the acid 1-IV is mentioned, the same applies for the isomeric acid 1-IVa, either in its pure form or in form of a mixture of 1-IV and 1-IVa. The same applies for reaction products derived from 1-IV: these can be obtained in pure form if the isomerically pure 1-IV or 1-IVa are used in the acylation step, or they can be obtained as a mixture if a mixture of 1-IV and 1-IVa is used and might be separated then by methods known to a person skilled in the art, e.g. by chromatography. There are many acylation methods known to a person skilled in the art: 1-IV can be converted to an acid chloride with oxalyl chloride, thionyl chloride or the like which can be isolated or used directly to react with 1-III in the presence of a base like triethylamine or diisopropylethylamine to give 1-V. The base might also be polymer-supported to ease work-up. The base might be used in excess, the excess might be removed using aqueous work-up or polymer-supported reagents like polymer-supported acid chloride. The acid 1-IV can also be reacted directly with the amine 1-III using coupling reagents like N,N,N'N'-tetramethyl-O-(7-azabenzotriazol-1-yl)-uronium hexafluorophosphate (HATU), N,N,N'N-tetramethyl-O-(1H-benzotriazol-1-yl)-uronium hexafluorophosphate (HBTU), 1-hydroxy-7-azabenzotriazole (HOAt), N,N'-dicyclohexylcarbodiimide (DCC) or the like. Other suitable amide coupling procedures are described in Goodman, M.; Felix, A.; Moroder, L.; Toniolo, C. in volume E22a of *Methods of Organic Chemistry (Houben-Weyl), Synthesis of Peptides and Peptidomimetics*, 4$^{th}$ edition, Georg Thieme Verlag, Stuttgart—New York, 2002. In an alternative synthetic route (route 2) the diamine can also be used as 1-VIII where the other nitrogen is protected. Coupling with 1-IV can be done as described for 1-III followed by deprotection as described for 1-VII yielding 1-X which is reacted with 1-1 as described for the reaction of 1-I with 1-VI. 1-V and 1-Va can be converted into their thiocarbonyl analogue 1-XI and 1-XIa by treatment with, for example, Lawesson's reagent under microwave heating. A compound of general formula 1-V can be substituted at $Y^1$-$Y^5$. This substituent can already be present in the heteroaryl compound 1-I. A person skilled in the art will appreciate that it can also be introduced in a compound 1-VII, 1-III or 1-V. For example, $Y^1$-$Y^5$ in 1-I might be substituted by a potential leaving group like, for example, halogen, which can be replaced by another group, for example a nucleophilic group in, for example, a nucleophilic substitution reaction. Or, for example, $Y^1$-$Y^5$ in 1-III might be substituted by a potential leaving group like, for example, halogen, which can be replaced by another group, for example a nucleophilic group in, for example, a nucleophilic substitution reaction. Or, for example, $Y^1$-$Y^5$ in 1-VII might be substituted by a potential leaving group like, for example, halogen, which can be replaced by another group, for example a nucleophilic group in, for example, a nucleophilic substitution reaction. 1-I might also be substituted at $Y^1$-$Y^5$ with a group that can react with a group present in the reaction partner 1-VI or 1-II like, for example, the amino group in 1-II or 1-VI. In this case the reacting group in 1-I can be protected by a protecting group by methods known to a person skilled in the art. For example, 1-I can be substituted by an acyl group. This acyl group can be protected as, for example, an oxolan prior to the reaction with 1-II or 1-VI and deprotected by, for example, aqueous acid after the reaction with 1-II or 1-VII as described in, for example, Green and Wuts, *Protective Groups in Organic Synthesis*, 3$^{rd}$ edition, John Wiley & Sons, New York, 1999. The same applies for the following schemes in an analogous way. The heteroaryl compound 1-I can be substituted at an N-Atom with oxygen, thus being a heteroaryl-N-oxide, for example a quinoline-N-oxide or a pyridine-N-oxide. Methods for the synthesis of such heteroaryl-N-oxides are described in, for example, R. Kreher (editor), volume E7a of *Methods of Organic Chemistry (Houben-Weyl), Hetarenes II, part 1*, 4$^{th}$ edition, Georg Thieme Verlag, Stuttgart—New York, 1991. A person skilled in the art will appreciate that the synthetic transformations described in scheme 1 result in this case in the corresponding heteroaryl-N-oxides of heteroaryl compounds of general formula 1-V and 1-Va, for example.

Scheme 2:

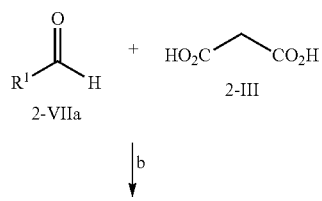

route 1

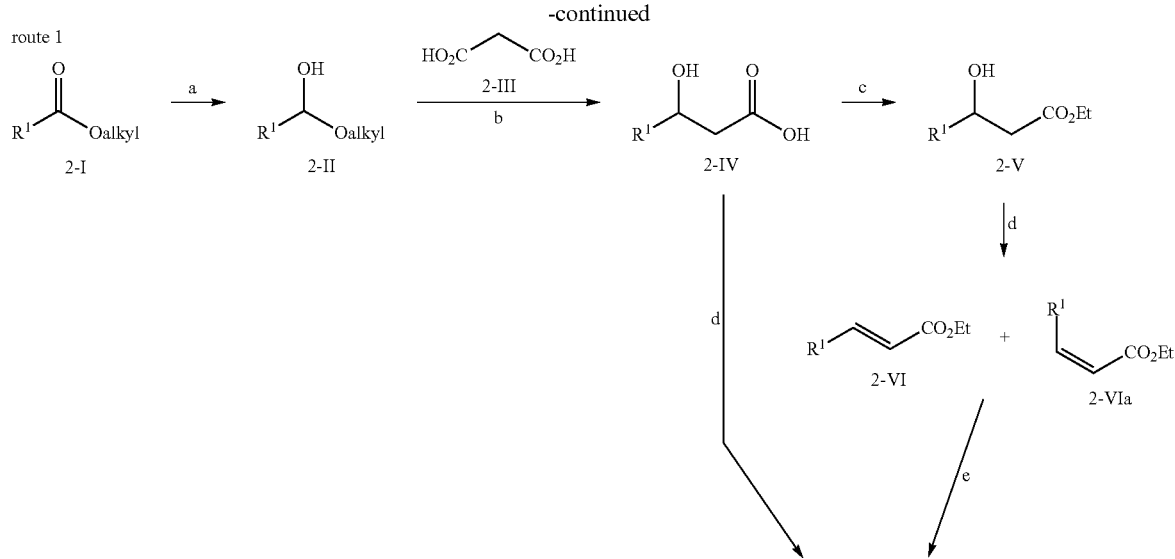

route 2 (R³ = H)

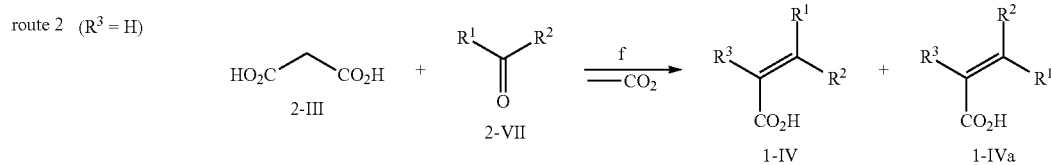

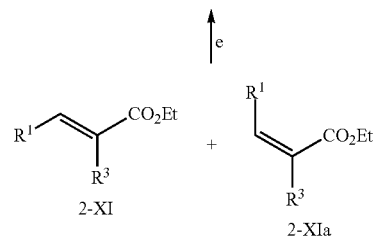

route 3

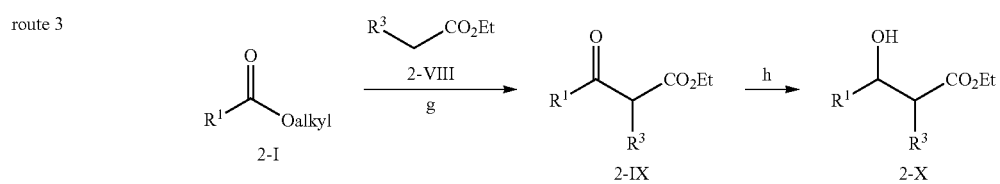

Exemplary conditions: a: sodium borohydride, methanol; b: pyridine, piperidine; c: ethanol, HCl; d: phosphorus pentoxide; e: NaOH; f: pyridine, piperidine, reflux; g: LiN(Si(CH$_3$)$_3$)$_2$, THF; h: sodium borohydride, toluene; i: phosphorus pentoxide The unsaturated acids used for acylation (1-IV in scheme 1) can be synthesized in several ways, many of which are described in: J. Falbe in volume E5 of *Methods of Organic Chemistry (Houben-Weyl), Carboxylic acids, part* 1, 4$^{th}$ edition, Georg Thieme Verlag, Stuttgart—New York, 1985. The preferred route will be chosen by a person skilled in the art according to the nature of the radicals $R^1$, $R^2$ and $R^3$. For example, in scheme 2, if $R^2$ is H and $R^1$ is alkyl preferably route 2 will be chosen. If $R^2$ is H and $R^1$ is alkyl substituted by halogen like F and/or Cl, route 1 or 3 will preferably be chosen. According to route 2 in scheme 2 malonic acid 2-III is condensed with an aldehyde or ketone 2-VII to yield directly the crotonic acid 1-IV, which can be accompanied by the isomeric 1-IVa. Suitable reaction conditions include heating the reactants in a solvent, preferably pyridine with the addition of piperidine. According to route 1, an ester is reduced to the hemiacetal 2-II, which is condensed with malonic acid in a manner analogous to route 1. Alternatively, the aldehyde 2-VIIa can be condensed with malonic acid to give the hydroxyacid 2-IV. The hydroxyacid 2-IV might be isolated or used directly in a dehydration step to yield 1-IV. Preferably, the hydroxyacid will be esterified to 2-V which is dehydrated to 2-VI and hydrolysed to the acid 1-IV. Methods for the dehydration of 2-IV and 2-V are described in, for example, M. Jagodzinska et al., *Tetrahedron* 63 (2007), 2042-2046; P. F. Bevilaqua, *J. Org. Chem.* 94 (1984), 1430-1434 and include treatment of a hydroxyacid or hydroxyester like 2-IV or 2-V with $P_2O_5$ at preferably elevated temperatures or treatment with diethylazodicarboxylate and triphenylphosphine. According to route 3 an ester 2-I is condensed with a CH-acidic ester 2-VIII to give a beta-keto ester 2-IX which is reduced to the hydroxyester 2-X. Methods for the condensation of an ester with another CH-acidic ester are known to a person skilled in the art, as well as methods for the reduction of a keto group to a hydroxy group and are described in, for example, M. Jagodzinska et al., *Tetrahedron* 63 (2007), 2042-2046; T. Kitazume, *J. Fluorine Chemistry* 42 (1989), 17-29. 2-X is then converted to the crotonic acid 1-IV in a manner analogous to the one described above for 2-V. In all of the described routes, 1-IV might be accompanied by the isomeric 1-IVa. Depending on the nature of the radicals $R^1$ and $R^2$ the isomers I-IV and I-IVa can be formed in varying proportions. For example if $R^2$ is H, the E-isomer I-IV is predominantly formed. The isomeric 1-IV and 1-IVa can be separated by methods known to a person skilled in the art, e.g. by chromatography and can be used as pure isomers in subsequent reactions. Or 1-IV and 1-IVa can be used as a mixture in subsequent reactions and the resulting isomeric products can be separated in a later step. Unsaturated acids with $R^1=SF_5$ and $R^2=H$ and $R^3=H$ can also be obtained as described in, for example, V. K. Brel, *Synthesis* 2006, 339-343. Unsaturated acids with $R^1$=alkylthio and alkylsulfonyl and $R^2=H$ and $R^3=H$ can also be obtained as described in, for example, J. T. Moon, *Bioorg. Med. Chem. Letters* 20 (2010) 52-55. Many unsaturated acids 1-IV used as starting materials are also commercially available by a large number of vendors as listed in, for example, the Symyx Available Chemicals Directory (ACD) or SciFinder (ACS).

Scheme 3:
route 1

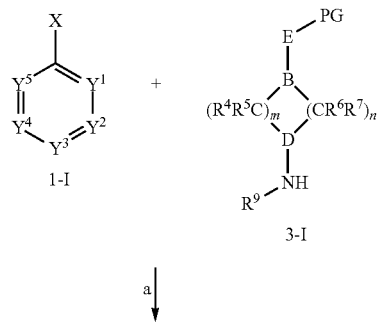

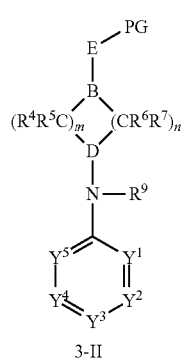

route 2

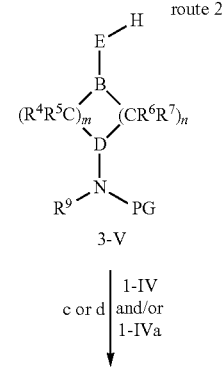

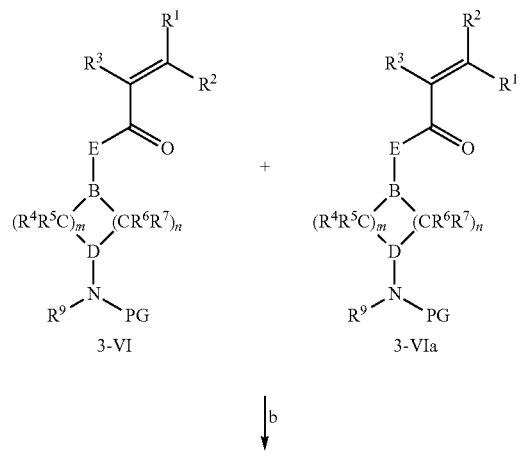

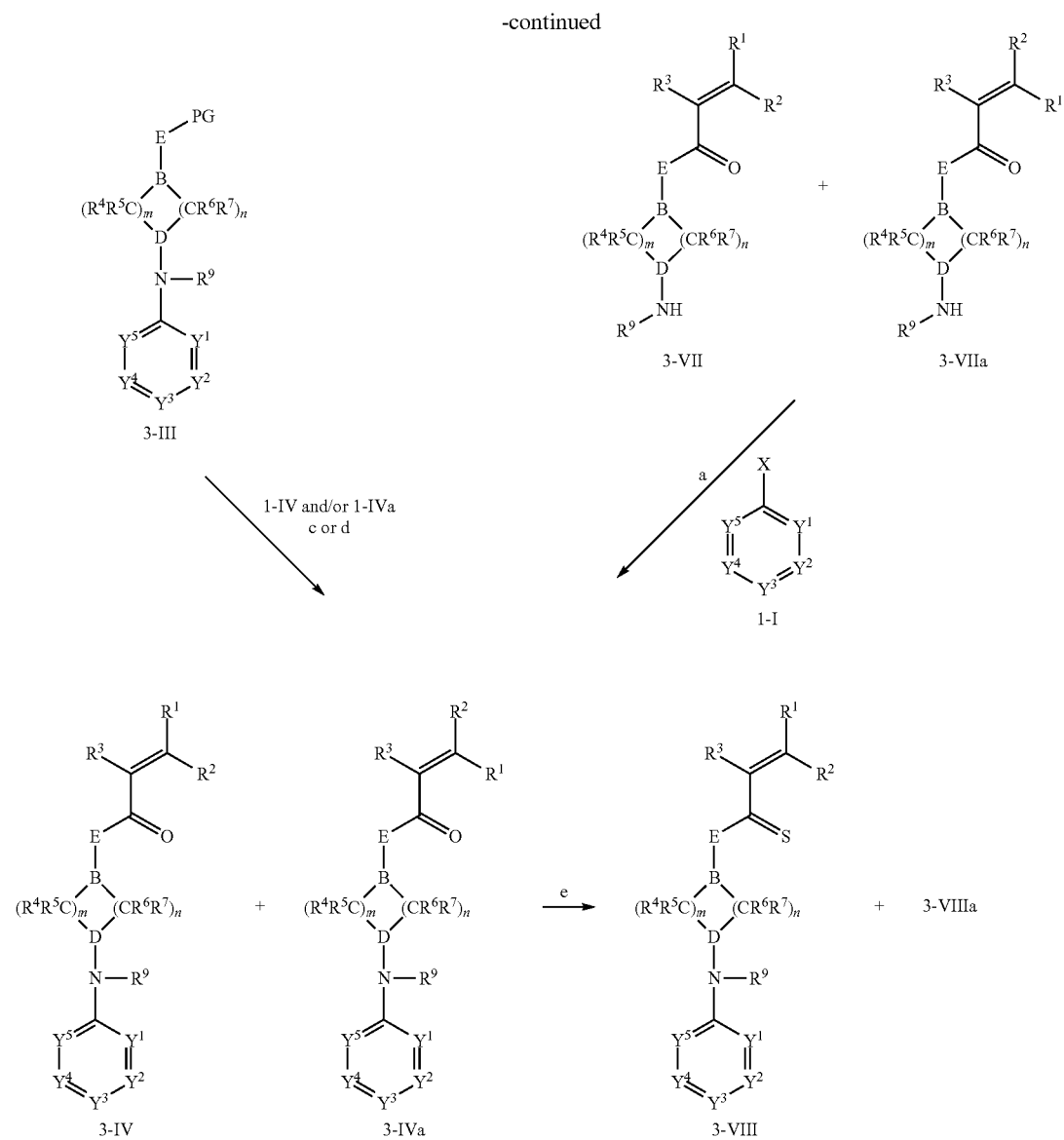

Exemplary conditions: a: Pd(OAc)$_2$, BINAP, Cs$_2$CO$_3$, dioxane; b: HCl, dioxane; c: (COCl)$_2$, DCM, DMF then DCM, triethylamine; d: HATU, N-ethyldiisopropylamine (EDIPA), DMF, room temperature; e: Lawesson's reagent, THF, 130° C.

Compounds of general formula 3-IV can be synthesized as shown in scheme 3: a monoprotected diamino compound 3-1 is reacted with a heteroaryl compound 1-I containing a suitable leaving group X as described in scheme 1. Suitable protecting groups are the ones which have already been described in scheme 1. Possible reaction conditions include Pd-catalysis using, for example, palladium acetate or Pd$_2$(DBA)$_3$, a phosphorus-containing ligand like BINAP or RuPhos or BrettPhos, a base like caesium carbonate or sodium tert-butoxide in a solvent like an ether-containing solvent like diethylether, dioxane or tetrahydrofuran, preferably dioxane. The protecting group is removed and 3-III is acylated with 1-IV as already described in scheme 1. 1-IV can be accompanied by the isomeric 1-IVa, so that a mixture of 1-IV and 1-IVa is used in the acylation step. In this case a mixture of 3-IV and 3-IVa is formed that can be separated by methods known to a person skilled in the art, e.g. by chromatography. Or 1-IVa can be used in a pure form in the acylation step to give 3-IVa. The sequence might be altered as shown in route 2: the monoprotected diamine 3-V is acylated first, deprotection as described above and coupling with 1-I follow to give 3-IV. Also here 1-IV can be accompanied by the isomeric 1-IVa, so that a mixture of 1-IV and 1-IVa is used in the acylation step. In this case a mixture of 3-VI and 3-VIa is formed after acylation that can be separated by methods known to a person skilled in the art, e.g. by chromatography, or separation can be done after deprotection to 3-VII and 3-VIIa or after reaction to the final product 3-IV and 3-IVa. Or 1-IVa can be used in a pure form in the acylation step to give 3-VIa. The heteroaryl compound 1-I can be substituted at Y$^1$-Y$^5$ with a group that might react with an amine like 3-I, 3-VII or 3-VIIa. In this case the reacting group can be protected by a protecting group by methods known to a person skilled in the art. For example, 1-I can be substituted by an acyl group. This acyl group can be protected as, for example, an oxolan prior to the reaction with 3-I, 3-VII or 3-VIIa and deprotected by, for example, aqueous acid after the reaction with 3-I, 3-VII or 3-VIIa as described in, for example, Green and Wuts, *Protective Groups in Organic Synthesis*, 3$^{rd}$ edition, John Wiley & Sons, New York, 1999. 3-IV and 3-IVa can be converted into their thiocarbonyl analogue 3-VIII and 3-VIIIa by treatment with, for example, Lawesson's reagent under microwave heating.

Scheme 4 (In 4-I the letter "B" has the meaning of the element boron unlike the other schemes were it has the meaning as describe for formula I):

Exemplary conditions: a: Pd(PPh$_3$)$_2$Cl$_2$, Na$_2$CO$_3$, ethylene glycol dimethylether, ethanol, water, heat; b: AsPh$_3$, tris(dibenzylidineacetone)dipalladium(0) (Pd$_2$(DBA)$_3$), 1-methylpyrrolidin-2-one, LiCl; c: hydrogen, Pd on charcoal, ethanol; d: (C001)$_2$, DCM, DMF then DCM, triethylamine; e: HATU, EDIPA, DMF, room temperature; f: Lawesson's reagent, THF, 130° C.; g: bis(pinacolato)diboron, 1,1'-bis(diphenylphosphino)ferrocene (dppf); (1,1'-bis(diphenylphosphino)ferrocene)palladium(II) dichloride (PdCl$_2$dppf); potassium acetate, 1,4-dioxane, 80° C.

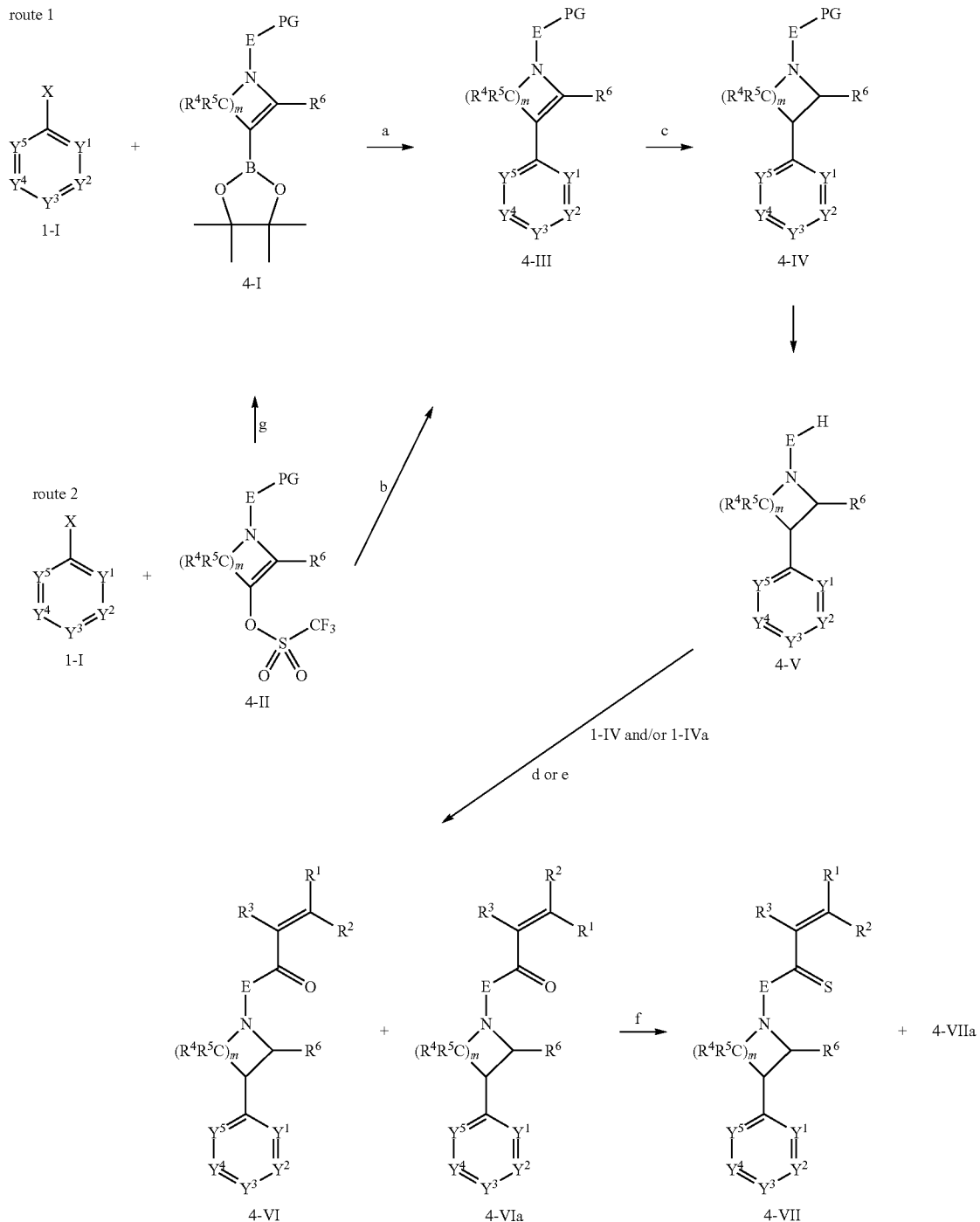

A compound of general formula 4-VI can be synthesized as shown in scheme 4: In route 1 a heteroaryl compound 1-I (wherein $Y^1$ is N and $Y^2$-$Y^5$ are C) containing a suitable leaving group X like bromine is reacted with an alkenylboronic acid derivative 4-I under Pd-catalysis to give 4-III which is hydrogenated to give 4-IV. 4-I can be obtained from the triflate 4-II as described in, for example, Paul R. Eastwood, *Tetrahedron Letters* 41 (2000), 3705-3708. Depending on the nature of the heteroaryl compound 1-I, 4-III can be obtained via route 2: a heteroaryl compound 1-I (wherein $Y^2$ is N and $Y^1$,$Y^3$-$Y^5$ are C) containing a suitable leaving group X like an organostannyl is reacted with the cyclic enol triflate 4-II under Pd-catalysis to give 4-III. The protecting group in 4-IV is removed as described in scheme 1 and 4-V is acylated with the unsaturated acid 1-IV as described in scheme 1 to give the final product 4-VI. 1-IV in the acylation step can be accompanied by the isomeric 1-IVa, so that a mixture of 1-IV and 1-IVa is used in the acylation step. In this case a mixture of 4-VI and 4-VIa is formed that can be separated by methods known to a person skilled in the art, e.g. by chromatography. Or 1-IVa can be used in a pure form in the acylation step to give 4-VIa. 4-VI and 4-VIa can be converted into their thiocarbonyl analogue 4-VII and 4-VIIa by treatment with, for example, Lawesson's reagent under microwave heating.

Exemplary conditions: a: propyleneglycolmonomethylether, 150° C.; b: n-butyllithium, THF, −78° C.; c: LiCl, acetonitrile, N-ethyl-diisopropylamine; d: Lawesson's reagent, THF, 130° C.

A compound of general formula 5-V can be synthesized as shown in scheme 5: a cyclic carboxylic ester 5-I containing an amino function is reacted with a heteroaryl compound 1-I containing a suitable leaving group as already described in scheme 1 to give 5-II. The reaction can be carried out, for example, in a solvent like propyleneglycolmonomethylether at elevated temperatures like at 150° C. 5-II is reacted with a dialkyl phosphonate in the presence of a base like lithium diisopropylamide in a solvent like THF at a temperature like −78° C. Similar reactions are described in, for example, U.S. Pat. No. 4,024,179. The ketophosphonate 5-IV can be reacted with the carbonyl compound 2-VII in a Wittig-Horner reaction under conditions such as, for example, described in S. V. Ley, *J. Chem. Soc., Perkin Trans.* 1., 1997, 3299-3313 using a base like diisopropylethylamine in the presence of lithium chloride in a solvent like acetonitrile. Depending on the nature of the radicals $R^1$ and $R^2$ the isomeric final products 5-V and 5-Va can be formed in differing proportions. For example, if $R^2$ is H and $R^3$ is H, then the E-isomer 5-VI is formed predominantly. If a mixture of 5-V and 5-Va is Scheme 5:

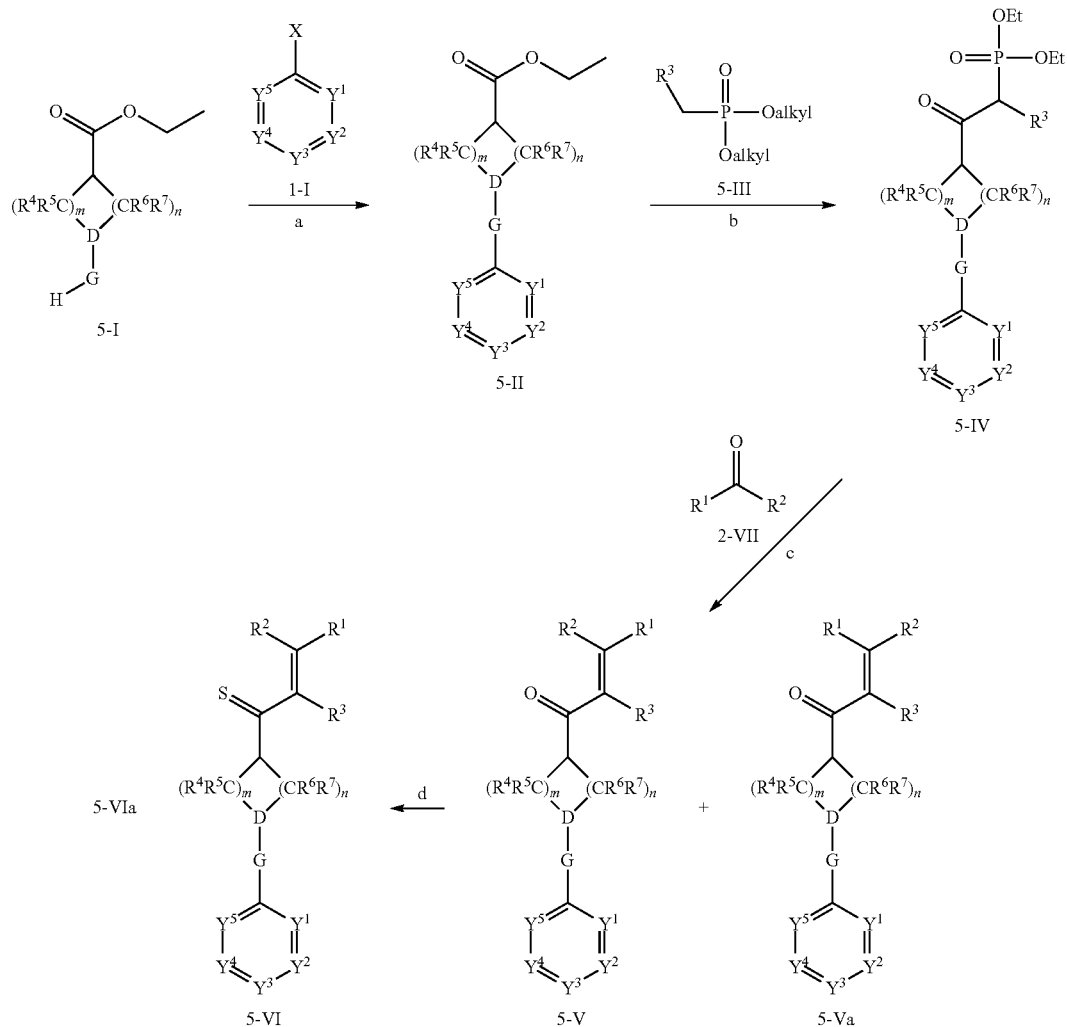

formed, this can be separated by methods known to a person skilled in the art, e.g. by chromatography. 5-V and 5-Va can be converted into their thiocarbonyl analogue 5-VI and 5-VIa by treatment with, for example, Lawesson's reagent under microwave heating.

be monoprotected as 1-VI (protection has been described in scheme 1) and used in route 1 to give 6-II. Deprotection under conditions already described in scheme 1 then gives the amino compound 6-III. Such a nucleophilic substitution of 6-I is suitable if 6-I is a pyrrol ($Y^7$ or $Y^{10}$ is N), thiophene ($Y^7$

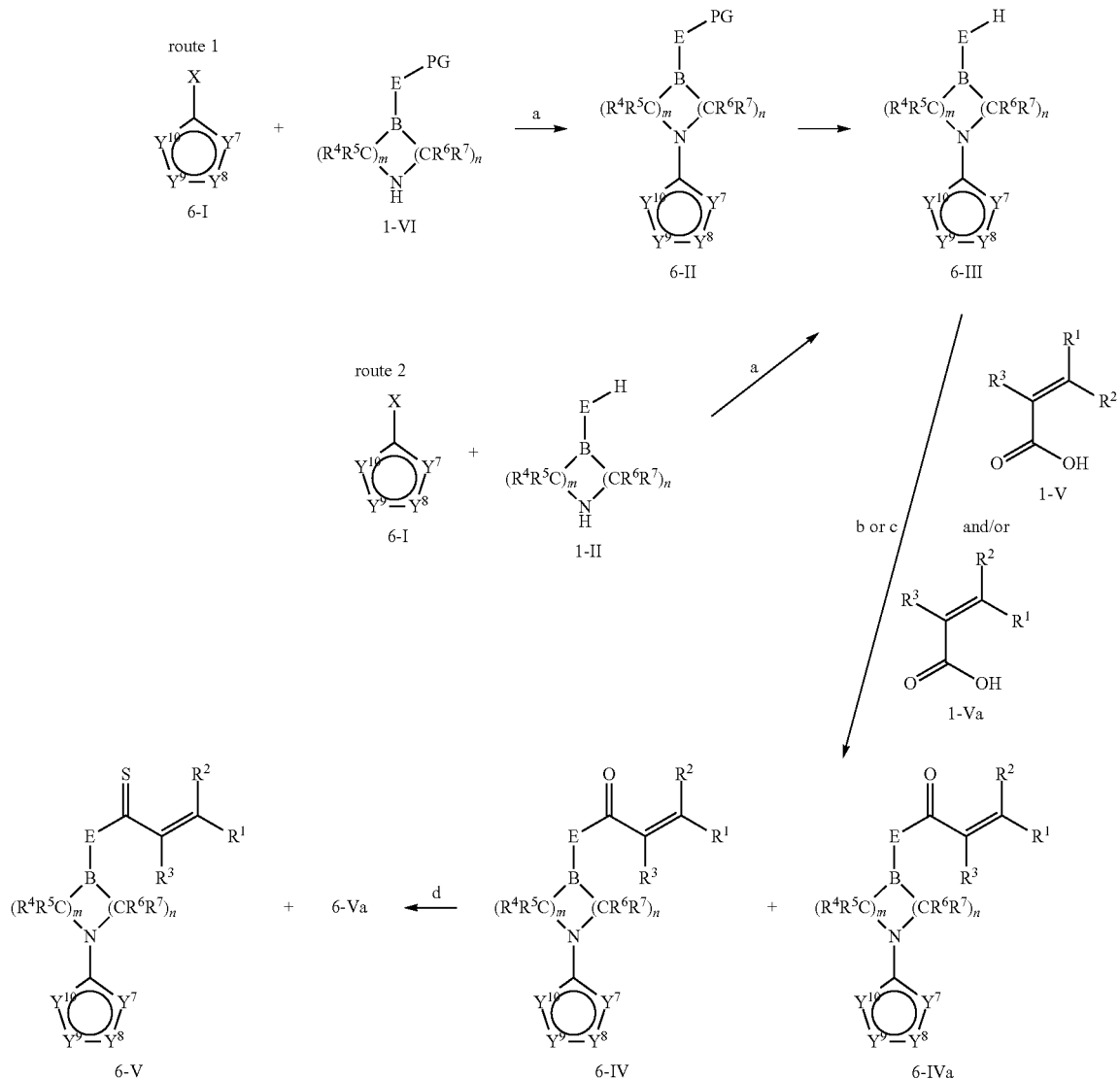

Scheme 6

Exemplary conditions: a: $Pd_2(DBA)_3$, NaO$^t$Bu, dicyclohexyl-[3,6-dimethoxy-2-(2,4,6-triisopropylphenyl)phenyl] phosphane, dioxane; b: oxalyl chloride, DCM, DMF, TEA, c: HBTU, DCM, DMF, EDIPA; d: Lawesson's reagent, THF, 130° C.

Compounds of general formula 6-IV can be synthesized as shown in scheme 6: In route 2 a heteroaryl compound 6-1 is reacted with a diamine 1-II to give 6-III. 6-I contains a suitable leaving group like chloro, bromo or a nitro group. The reaction can be carried out in a solvent like an alcohol, or a diol-derived solvent like ethyleneglycolmonomethyl ether or in a solvent like dioxane or can be carried without solvent. A base might be present like, for example, potassium carbonate. The reaction is done preferably at elevated temperatures and the diamine 1-II is used preferably in excess. The diamine can or $Y^{10}$ is S), furane ($Y^7$ or $Y^{10}$ is O) or a benz-annulated derivative of these such as benzothiophene, benzofurane or benzopyrrole, wherein these heteroaromates are preferably substituted by electron-withdrawing substituents. Particularly suitable is such a reaction if 6-I is an imidazol ($Y^7$ and $Y^{10}$ are both N and one N is preferably substituted by preferably an alkyl group), a thiazol ($Y^7$ and $Y^{10}$ are N and S, respectively) or an oxazol ($Y^7$ and $Y^{10}$ are N and O, respectively) or a benz-annulated derivative thereof. Alternatively, the reaction between 6-I and the amine 1-II or 1-VII can be carried out under Pd-catalysis using a Pd source like, for example, palladium acetate or $Pd_2(DBA)_3$, a phosphorus-containing ligand like BINAP or RuPhos or BrettPhos, a base like caesium carbonate or sodium tert-butoxide as described in, for example, Hooper, M. W., et al. *J. Org. Chem.* 68, (2003), 2861-2873 or Charles, M. D., et al., *Org. Lett.* 7(18), (2005), 3965-3968. Pd-catalysis is especially useful if the heteroaromate 6-I is not activated towards nucleophilic substitution by carrying an electron withdrawing substituent or if neither $Y^7$ nor $Y^{10}$ is a heteroatom, but also in cases where 6-I is suitable for nuceleopilic substitution by 1-II or 1-VI as described above, Pd-catalysis can be used alternatively. 6-III is then acylated by the unsaturated acid 1-V to give the amide 6-IV, as described in scheme 1. 1-V can be accompanied by the isomeric 1-Va so that a mixture of 6-IV and 6-IVa is obtained that can be separated by, for example, chromatography. 6-IV and 6-IV can be converted into their thiocarbonyl analogue 6-V and 6-Va by treatment with, for example, Lawesson's reagent under microwave heating Scheme 7:

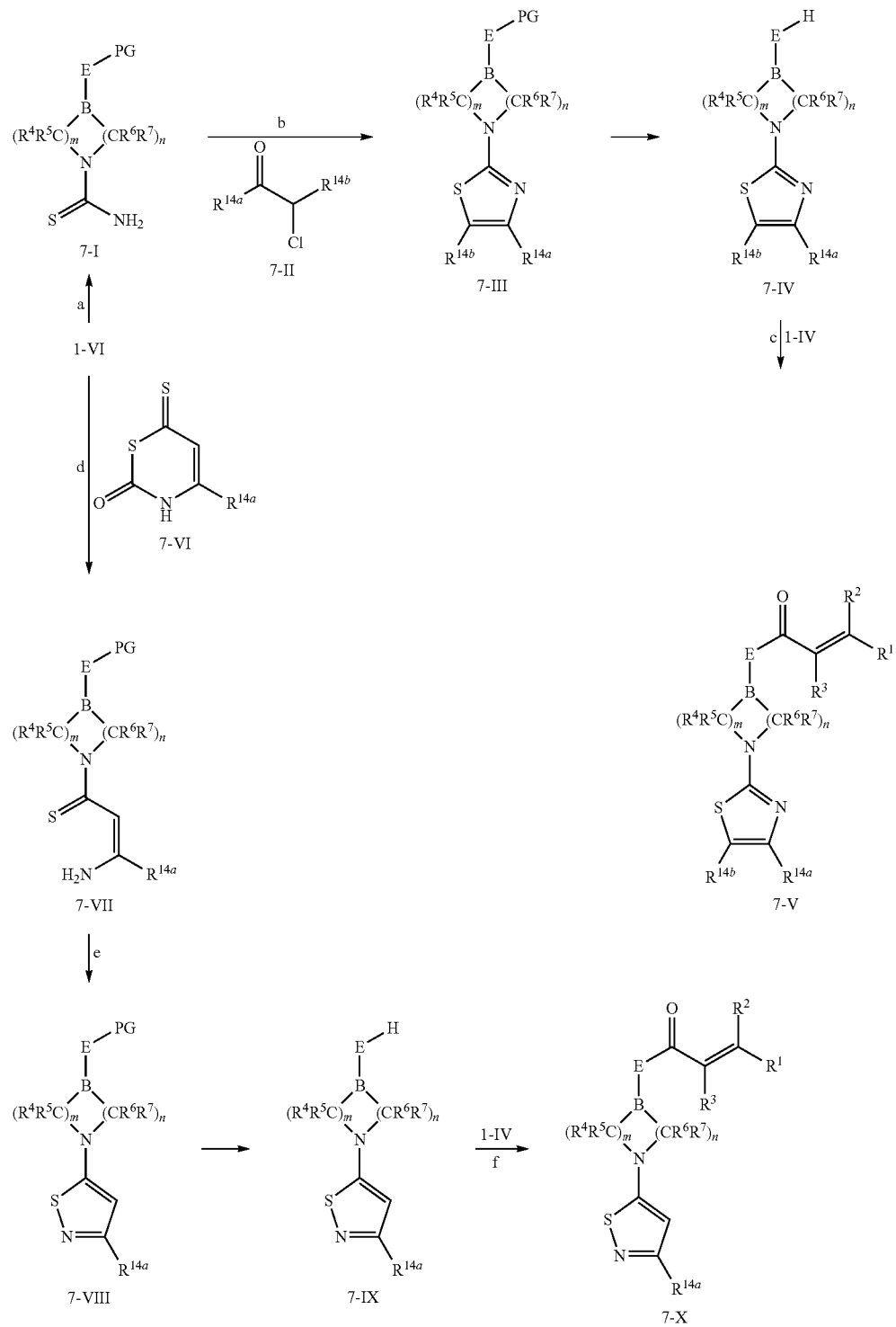

Exemplary conditions: a: 1,1-thiocarbonyldiimidazole, THF, then ammonia, ethanol; b: TEA, dioxane; c: oxalyl chloride, DCM, DMF, TEA; d: ethanol; e: iodine, pyridine, ethanol; f: oxalyl chloride, DCM, DMF, TEA Exemplary conditions: a: 3-(ethyliminomethyleneamino)-N,N-dimethyl-propan-1-amine hydrochloride (EDC), 1-hydroxybenzotriazole, N-methylmorpholine, DCM; b: hydrogen, Pd/C, methanol; d: Lawesson's reagent, pyridine; e:

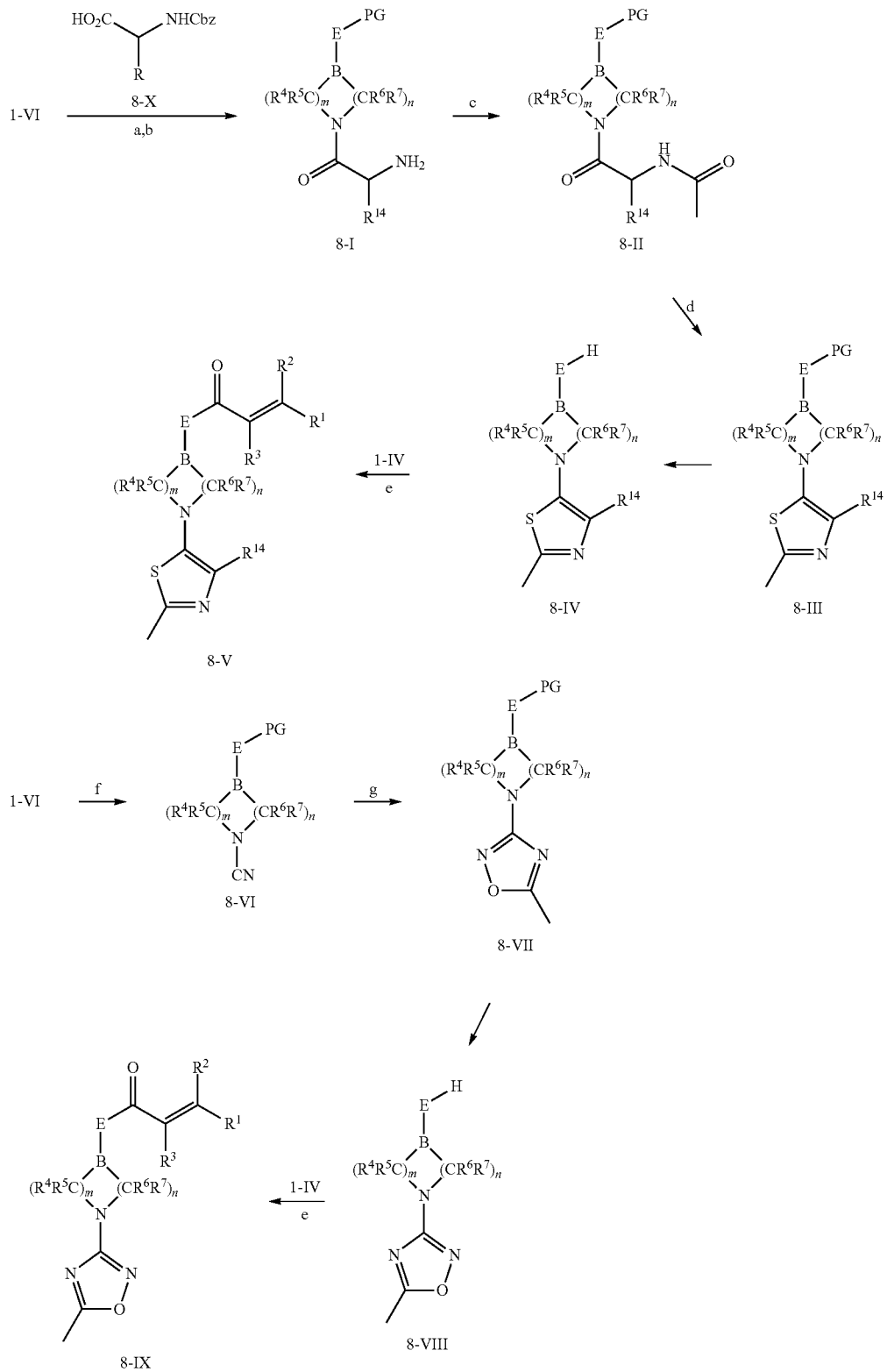

oxalyl chloride, DCM, DMF, TEA; f: BrCN, EDIPA, DCM; g: hydroxylamine hydrochloride, TEA, ethanol, then acetic acid anhydride, pyridine.

Alternative synthesis routes for compounds of general formula 6-VI are shown in schemes 7 and 8. The appropriate route can be selected based on the nature of the heteroaromatic radical in 6-VI and has been described in, for example, Kondo, T. et al., *Bioorg. Med. Chem.* 16 (2008), 1613-1631. For example, a 1,3-thiazol 7-V can be synthesized starting from the mono-protected diamine 1-VI which is converted to the thiocarbamate derivative 7-I which is cyclized with the α-chlorocarbonyl compound 7-II to the thiazol 7-III. Deprotection and acylation as already described in the preceding schemes gives the final compound 7-V. In analogy to what has been described in scheme 1, 7-V can be accompanied by its double bond isomer and 7-V can be converted to its thioamide analogue, which also applies to the other final compounds described in schemes 7 and 8 (7-X, 8-V, 8-IX). Starting from 1-VI the isothiazol 7-X can be obtained by a reaction sequence starting by treatment of 1-VI with 7-VI the synthesis of which is described in, for example, Schroth, W. et al., *Z. Chem.* 25(1) (1985), 20-21. Treatment with iodine then gives the isothiazole derivative 7-VIII. Deprotection and acylation as described above and in the preceding schemes then gives the final compound 7-X. 1,3-Thiazoles of general formula 8-V can be obtained by the following reaction sequence: 1-VI is acylated with a N-protected amino acid 8-X, wherein the protecting group in 8-X is orthogonal to the protecting group in 1-VI, for example the nitrogen in 8-X is protected by a Cbz-group and the nitrogen in 1-VI is protected by a Boc-group. The protecting group of the amino acid-derived nitrogen is removed, for example by hydrogenation, and the resulting free amine is acylated to give 8-II. Cyclization then gives the thiazole derivatives 8-III, deprotection and acylation as described above gives the final compound 8-V. An oxadiazole of general formula 8-IX can be obtained by the following reaction sequence: 1-VI is converted to the carbonitrile derivative 8-VI which is cyclized to the oxadiazole 8-VII. Deprotection and acylation as described above gives the final compound 8-IX.

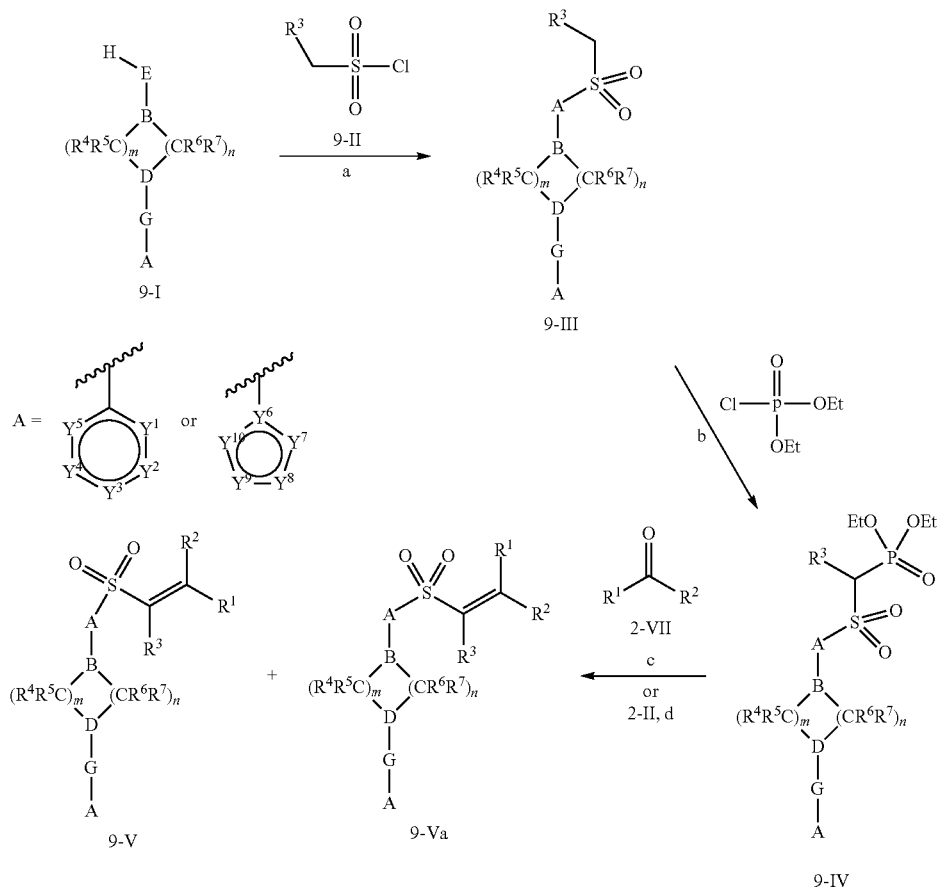

Scheme 9:

Exemplary conditions: a: dichloromethane, triethylamine, 0° C.; b: LiN(Si(CH$_3$)$_3$)$_2$, THF, −78° C.; c: NaH, THF, 0° C.; d: NaH, molsieve, 0° C.

A compound of the general formula 9-V can be synthesized as shown in scheme 9: A compound 9-I which contains an NH-group is reacted with an alkylsulfonic acid chloride 9-II in the presence of a suitable base like triethylamine in a solvent like dichloromethane. 9-I can be synthesized, for example, according to schemes 1, 3, 4, 6, 7 or 8. The sulfonamide 9-III is deprotonated with a strong base like lithium diisopropylamide, lithium hexamethyldisilazide or n-butyllithium at low temperature like −78° C. and reacted with diethylchlorophosphate to give 9-IV. 9-IV is then reacted with a carbonyl compound 2-VII to give the final product 9-V. The last step can be carried out in the presence of a strong base like sodium hydride or in the presence of lithium bromide and a strong base like 1,8-diaza-bicyclo[5.4.0]undec-7-en (DBU) as described in, for example, Z. Wróbel, *Tetrahedron* 57 (2001), 7899-7907. Alternatively, the hemiacetal 2-II might be used instead of the carbonyl compound 2-VIII. Depending on the nature of the radicals $R^1$, $R^2$ and $R^3$ the isomeric final products 9-V and 9-Va can be formed in differing proportions. For example, if $R^2$ is H and $R^3$ is H, then the E-isomer 9-V is formed predominantly. If a mixture of 9-V and 9-Va is formed, this can be separated by methods known to a person skilled in the art, e.g. by chromatography.

Heteroaryl compounds 1-I used as starting materials can be synthesized by several methods known to those skilled in the art. Quinoline derivatives are described in, for example, R. Kreher (editor), volume E7a of *Methods of Organic Chemistry (Houben-Weyl), Hetarenes II, part 1*, 4th edition, Georg Thieme Verlag, Stuttgart-New York, 1991; pyridine derivatives are described in, for example, R. Kreher (editor), volume E7b of *Methods of Organic Chemistry (Houben-Weyl), Hetarenes II, part 2*, 4th edition, Georg Thieme Verlag, Stuttgart—New York, 1992; pyrimidines, pyrazines, quinazolines and quinoxalines are described in, for example, E. Schaumann (editor), volume E9b of *Methods of Organic Chemistry (Houben-Weyl), Hetarenes IV, part 2a*, 4th edition, Georg Thieme Verlag, Stuttgart—New York, 1998; pyridazines and cinnolines in, for example, E. Schaumann (editor), volume E9a of *Methods of Organic Chemistry (Houben-Weyl), Hetarenes IV, part I*, 4th edition, Georg Thieme Verlag, Stuttgart—New York, 1997; 1,2-thiazoles, 1,2-benzothiazoles, 1,3-oxazoles and 1,3-benzoxaloes in, for example, E. Schaumann (editor), volume E8a of *Methods of Organic Chemistry (Houben-Weyl), Hetarenes III, part I*, 4th edition, Georg Thieme Verlag, Stuttgart—New York, 1993; 1,3-thiazoles, 1-3-benzothiazoles and pyrazoles in, for example, E. Schaumann (editor), volume E8b of *Methods of Organic Chemistry (Houben-Weyl), Hetarenes III, part 2*, 4th edition, Georg Thieme Verlag, Stuttgart—New York, 1994; imidazoles, benzimidazoles and oxadiazoles in, for example, E. Schaumann (editor), volume E8c of *Methods of Organic Chemistry (Houben-Weyl), Hetarenes III, part 3*, 4th edition, Georg Thieme Verlag, Stuttgart—New York, 1994; thiadiazoles in, for example, E. Schaumann (editor), volume E8d of *Methods of Organic Chemistry (Houben-Weyl), Hetarenes III, part 4*, 4th edition, Georg Thieme Verlag, Stuttgart—New York, 1994; thiophenes, pyrroles and furanes in, for example, R. Kreher (editor), volume E6a of *Methods of Organic Chemistry (Houben-Weyl), Hetarenes I, part 1*, 4th edition, Georg Thieme Verlag, Stuttgart-New York, 1994; indoles and benzothiophenes in, for example, R. Kreher (editor), volume E6b of *Methods of Organic Chemistry (Houben-Weyl), Hetarenes I, part 2*, 4th edition, Georg Thieme Verlag, Stuttgart—New York, 1994. Many heteroaryl compounds 1-I used as starting materials are also commercially available by a large number of vendors as listed in, for example, the Symyx Available Chemicals Directory (ACD).

Cyclic diamines 1-II, 1-VI, 1-VIII, 3-I, 3-V and amines 5-I used as starting materials are commercially available by a large number of vendors as well as carboxylic esters 2-I and 2-VIII, aldehydes 2-VIIa and carbonyl compounds 2-VII as listed in, for example, the Symyx Available Chemicals Directory (ACD). In addition, carboxylic esters can be obtained by methods known to a person skilled in the art and described in, for example, J. Falbe (editor), volume E5 of *Methods of Organic Chemistry (Houben-Weyl), Carboxylic acids and Derivatives, part I*, 4th edition, Georg Thieme Verlag, Stuttgart-New York, 1985. Likewise, aldehydes can be obtained by methods described in, for example, J. Falbe (editor), volume E3 of *Methods of Organic Chemistry (Houben-Weyl), Aldehydes*, 4th edition, Georg Thieme Verlag, Stuttgart—New York, 1983 and ketones as described in, for example, volume VII, part 2a-c of *Methods of Organic Chemistry (Houben-Weyl), Ketones I-III*, 4th edition, Georg Thieme Verlag, Stuttgart—New York, 1973-1977. The triflates 4-II can be obtained from the corresponding carbonyl derivatives as described in, for example James C. Barrow et al, *J. Med. Chem.* 43 (2000), 2703-2718. Alkyl phosphonates 5-III are commercially available or can be obtained by methods known to a person skilled in the art described in, for example, in M. Regitz (editor), in volume E2 of *Methods of Organic Chemistry (Houben-Weyl), Organic Phosphorus Compounds II*, 4th edition, Georg Thieme Verlag, Stuttgart—New York, 1982. Alkyl sulfonic acid chlorides 9-II are commercially available or can be obtained by methods known to a person skilled in the art described in, for example, in D. Klamann (editor), in volume E11, part 2 of *Methods of Organic Chemistry (Houben-Weyl), Organic Sulfur Compounds II*, 4th edition, Georg Thieme Verlag, Stuttgart—New York, 1987.

B. Synthesis Examples

The following examples are for illustrative purposes only and are not intended to limit the scope of the invention. The compounds were named using Symyx® draw version 3.1.Net software (Symyx Technologies, Inc.).

The methods described in the examples can be easily adapted by a person skilled in the art to make other compounds as described in this specification and intermediates thereof. For instance, a person skilled in the art could replace in the examples the exemplified starting compounds by other compounds of the formulae 1-I, 1-II, 1-VI, 2-I, 2-VII, 2-VIIa, 2-VIII, 3-I, 3-V, 4-I, 4-II, 5-I, 5-III, 6-I, 7-II, 7-VI, 8-X, 9-II (e.g. commercially available compounds), perform routine adaptions of the reaction conditions, if any, and use them for the synthesis of further compounds according to this invention.

Example 1

Synthesis of (E)-4,4-difluoro-1-[4-(5-methyl-1,2,4-oxadiazol-3-yl)piperazin-1-yl]pent-2-en-1-one (B-12)

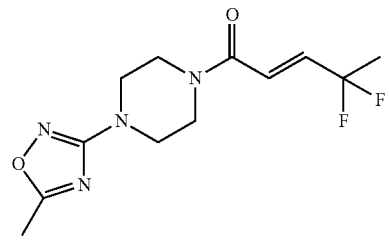 [SMILES: Cc1nc(N2CCN(C(=O)/C=C/C(C)(F)F)CC2)no1]

Step A: Ethyl 4,4-difluoro-3-oxo-pentanoate

Lithium hexamethyldisilazide (150 ml of a 1M solution in THF, 0.15 mol) was cooled in an argon atmosphere to −78° C. and ethyl acetate (15 ml, 0.14 mol) was added dropwise with stirring. Stirring was continued for one hour at −78° C., then ethyl 2,2-difluoropropionate (12 g, 0.089 mol) was added dropwise with stirring. Stirring was continued for four hours at −78° C., then a saturated solution of ammonium chloride (175 ml) was added dropwise. The mixture was allowed to reach room temperature, acidified with 1M HCl (50 ml) and left standing overnight. The phases were separated. The aqueous phase was extracted with ethyl acetate, the combined organic phases were washed with 1M HCl, brine and dried over sodium sulfate. The solvent was removed under reduced pressure and the residue was purified by vacuum distillation (54 mbar, 130° C.) to yield 12.4 g (0.068 mmol, 77%) of a colourless liquid that was used directly in the next step.

Step B: Ethyl 4,4-difluoro-3-hydroxy-pentanoate

Ethyl 4,4-difluoro-3-oxo-pentanoate (12.4 g, 0.068 mmol) was dissolved in toluene (100 ml) and cooled to 0° C. Sodium borohydride (3.12 g, 0.083 g) was added portionwise, and the mixture was allowed to reach room temperature overnight with stirring. The mixture was then cooled to 0° C. and acidified with 1M HCl. The phases were separated, the aqueous phase was extracted two times with ethyl acetate, the combined organic phases were dried over magnesium sulfate and the solvent was removed under reduced pressure. The residue was dissolved in a minimum amount of methanol, the resulting solution was evaporated to dryness under reduced pressure to yield 8.76 g of a residue (0.048 mol, 70%) that were used directly in the next step.

Step C: Ethyl (E)-4,4-difluoropent-2-enoate

Ethyl 4,4-difluoro-3-hydroxy-pentanoate (3.39 g, 0.0186 mol) was dissolved in THF (20 ml). Diphenyl-2-pyridylphosphin (7.37 g, 0.028 mol) was added followed after five minutes by di-$^{tert}$butylazodicarboxylate (2.83 g, 0.028 mol). The mixture was stirred for one hour at room temperature and left standing overnight. The mixture was acidified with trifluoroacetic acid (2 ml) and stirred for one hour at room temperature. The solvent was removed under reduced pressure and the residue partitioned between ethyl acetate and 4N HCl. The phases were separated, the organic phase was washed with 1M HCl (4×), dried over magnesium sulfate and evaporated to dryness. After distillation at 2 mbar 5.99 g were obtained which still contained some solvent but were used directly in the next step.

Step D: (E)-4,4-Difluoropent-2-enoic acid

The product of step C was dissolved in ethanol (24 ml), 4M NaOH was added (12 ml) and the mixture was stirred at room temperature for two hours. The mixture was acidified with 1M HCl and extracted with ethyl acetate. The organic extract was dried over magnesium sulfate, the solvent was removed under reduced pressure. 2.67 g of a colourless oil were obtained. MS (ESI) m/z=135.0 [M−1]$^-$.

Step E: tert-Butyl 4-cyanopiperazine-1-carboxylate

To a cooled (0° C.) solution of tert-butyl piperazine-1-carboxylate (1.517 g, 8.14 mmol) in dichloromethane (10 mL) were added N,N-diisopropylethylamine (1.54 mL, 9.00 mmol) and cyanogen bromide (911 mg, 8.60 mmol) and the reaction was stirred for 45 min at 0° C. The reaction mixture was warmed to room temperature, poured in water (100 mL) and extracted with EtOAc (100 mL). The organic layer was washed with water and brine, dried (Na$_2$SO$_4$) and concentrated under reduced pressure. The residue was washed twice with heptane and dried in vacuo, yielding 1.24 g (5.87 mmol, 72%) of a white solid that was used directly in the next step.

Step F: tert-Butyl 4-(N-hydroxycarbamimidoyl)piperazine-1-carboxylate

To a solution of tert-butyl 4-cyanopiperazine-1-carboxylate (1.22 g, 5.77 mmol) in anhydrous ethanol (10 mL) were added hydroxylamine hydrochloride (420 mg, 6.04 mmol) and triethyl amine (843 L, 6.06 mmol). The reaction was heated to reflux for 45 min, after which TLC showed complete consumption of the starting material. The mixture was allowed to cool to room temperature overnight, and the resulting precipitate was removed by filtration. The filtrate was concentrated, yielding 1.42 g of a yellow gel that was used directly in the next step.

Step G: tert-Butyl 4-(5-methyl-1,2,4-oxadiazol-3-yl)piperazine-1-carboxylate

To a solution of tert-butyl 4-(N-hydroxycarbamimidoyl)piperazine-1-carboxylate (771 mg, 3.16 mmol) in pyridine (8 mL) was added acetic anhydride (320 L, 3.42 mmol) and the reaction was heated to 80° C. for 3 h. The mixture was cooled to room temperature, poured into water and extracted with EtOAc. The organic layer was washed with water and brine, dried (Na2SO4) and concentrated under reduced pressure to yield 774 mg of a yellow solid. After purification by flash chromatography (silica, gradient of 0.5 to 3% methanol in dichloromethane) 509 mg of an off-white solid were obtained (1.897 mmol, 60%). MS (ESI) m/z=291.1 [M+Na]$^+$.

Step H: 5-Methyl-3-piperazin-1-yl-1,2,4-oxadiazole hydrochloride

To a solution of tert-butyl 4-(5-methyl-1,2,4-oxadiazol-3-yl)piperazine-1-carboxylate (507 mg, 1.890 mmol) in diethyl ether (12 mL) was added HCl, 4N in dioxane (7 mL, 28.0 mmol) and the reaction was stirred at room temperature over the weekend. The precipitate was isolated by filtration, washed with diethylether and dried under reduced pressure after which 330 mg of a white solid were obtained (1.612 mmol, 85%). MS (ESI) m/z=169.2 [M+1]$^+$.

Step I: (E)-4,4-Difluoro-1-[4-(5-methyl-1,2,4-oxadiazol-3-yl)piperazin-1-yl]pent-2-en-1-one (E)-4,4,5,5-Tetrafluoropent-2-enoic acid (31 mg, 0.23 mmol) was dissolved in dichloromethane (1 ml), oxalyl chloride (20 μl, 0.23 mol) and one drop of DMF were added and the resulting solution was stirred at room temperature for 15 minutes. This solution was added to a solution of 5-methyl-3-piperazin-1-yl-1,2,4-oxadiazole hydrochloride (25 mg, 0.122 mmol) in dichloromethane (2 ml) and the resulting mixture was stirred at room temperature for three hours. The solvent was removed under reduced pressure and the resulting residue was purified by preparative HPLC (Waters XBridge, gradient of water containing 0.1% NH$_3$ and acetonitrile) to yield 24.3 mg of a solid (0.083 mmol, 69%).

Example 2

Synthesis of (E)-4,4,4-trifluoro-1-[4-(4-methylpyrimidin-2-yl)piperazin-1-yl]but-2-en-1-one (A-16)

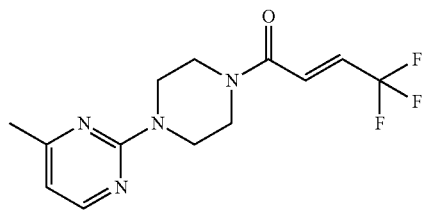 [SMILES: Cc1ccnc(N2CCN(C(=O)/C=C/C(F)(F)F)CC2)n1]

Step A: tert-Butyl 4-(4-methylpyrimidin-2-yl)piperazine-1-carboxylate

Palladium acetate (45 mg, 0.2 mmol), BINAP (62 mg, 0.1 mmol) and cesium carbonate (650 mg, 2 mmol) were suspended in anhydrous 1,4-dioxane (3 ml) under an argon atmosphere and sonicated for 45 minutes. 2-Bromo-4-methylpyrimidine (173 mg, 1 mmol) and tert-butyl piperazine-1-carboxylate (208 mg, 1.3 mmol) were dissolved in 3 ml anhydrous 1,4-dioxane and the resulting solution was added to the catalyst-containing mixture. The resulting mixture was stirred at 110° C. overnight, afterwards diluted with ethyl acetate and filtered. The filtrate was evaporated to dryness under reduced pressure and the residue was purified by column chromatography (silica, gradient from DCM to DCM/ethyl acetate 8/2) to yield 120 mg of a brown oil (0.43 mmol, 43%) MS (APCI) m/z=279.2 [M+1]$^+$.

Step B: 4-Methyl-2-piperazin-1-yl-pyrimidine dihydrochloride

The product from the previous step (tert-butyl 4-(4-methylpyrimidin-2-yl)piperazine-1-carboxylate) was dissolved in a one-to-one mixture of trifluoroacetic acid and DCM (8 ml) and stirred at room temperature for three hours. The volatiles were removed under reduced pressure, the residue was dissolved in DCM and evaporated. The residue was dissolved in THF (10 ml), HCl in dioxane (4N, 2 ml) was added and the resulting precipitate was collected by repeated centrifugation, dekantation and washing with THF to yield 107 mg of a solid (0.30 mmol, 71%). MS (APCI) m/z=179.1 [M+1]$^+$.

Step C: (E)-4,4,4-Trifluoro-1-[4-(4-methylpyrimidin-2-yl)piperazin-1-yl]but-2-en-1-one (E)-4,4,5,5-Trifluorobut-2-enoic acid (33 mg, 0.23 mmol) was dissolved in dichloromethane (1 ml), oxalyl chloride (20 µl, 0.23 mol) and one drop of DMF were added and the resulting solution was stirred at room temperature for 15 minutes. This solution was added to a solution of 4-methyl-2-piperazin-1-yl-pyrimidine dihydrochloride (43 mg, 0.17 mmol) in dichloromethane (2 ml) and the resulting mixture was stirred at room temperature for three hours. The solvent was removed under reduced pressure and the resulting residue was purified by preparative HPLC (Waters XBridge, gradient of water containing 0.1% NH$_3$ and acetonitrile) to yield 28 mg of a solid (0.093 mmol, 55%).

Example 3

Synthesis of (E)-4,4,4-trifluoro-1-[4-(4-methylthiazol-5-yl)piperazin-1-yl]but-2-en-1-one (B-11)

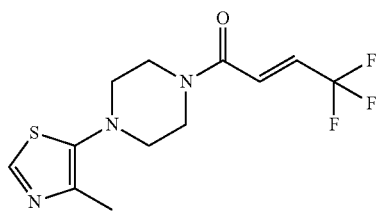 [SMILES: Cc1ncsc1N1CCN(C(=O)/C=C/C(F)(F)F)CC1]

Step A: tert-Butyl 4-(4-methylthiazol-5-yl)piperazine-1-carboxylate

A solution of 5-bromo-4-methylthiazole (454 mg, 2.55 mmol), N-Boc-piperazine (940 mg, 5.05 mmol), sodium tert-butoxide (492 mg, 5.12 mmol) and dicyclohexyl-[3,6-dimethoxy-2-(2,4,6-thisopropylphenyl)phenyl]phosphane (BrettPhos, 64.9 mg, 0.121 mmol) in anhydrous 1,4-dioxane (9 mL) was flushed with argon for 3 min. Tris(dibenzylideneacetone)dipalladium(0) (106 mg, 0.116 mmol) was added and the mixture was heated in a sealed flask to 70° C. for 2.5 hours. The reaction mixture was cooled to room temperature, diluted with EtOAc, filtered through kieselguhr and the filtrate was concentrated under reduced pressure to yield 1.5 g of a brown oil which was purified by flash chromatography (silica, gradient of 0.5 to 3% methanol in dichloromethane). 267 mg of a light-yellow oil were obtained (0.942 mmol, 37%). MS (ESI) m/z=284.2 [M+1]$^+$.

Step B: 4-Methyl-5-piperazin-1-yl-thiazole dihydrochloride

To a solution of tert-butyl 4-(4-methylthiazol-5-yl)piperazine-1-carboxylate (265 mg, 0.935 mmol) in diethyl ether (10 mL) was added HCl (4N in dioxane, 4.5 mL, 18 mmol) after which a precipitate formed immediately. 1,4-Dioxane (5 mL) was added to dissolve the precipitate. The mixture was stirred at room temperature for three days after which additional HCl (4N in dioxane, 5 mL, 20 mmol) and methanol (5 ml) was added. Stirring was continued for another day, the precipitate formed was collected by filtration, washed with diethylether and dried under reduced pressure to yield 208 mg of a yellow solid (0.812 mmol, 87%). MS (ESI) m/z=184.1 [M+1]$^+$.

Step C: (E)-4,4,4-Trifluoro-1-[4-(4-methylthiazol-5-yl)piperazin-1-yl]but-2-en-1-one (E)-4,4,4-Trifluorobut-2-enoic acid (33 mg, 0.23 mmol) was dissolved in dichloromethane (1 ml), oxalyl chloride (20 µl, 0.23 mol) and one drop of DMF were added and the resulting solution was stirred at room temperature for 15 minutes. This solution was added to a solution of 4-methyl-5-piperazin-1-yl-thiazole dihydrochloride (38 mg, 0.15 mmol) and N-ethyl-N,N-diisopropylamine (0.7 mmol, 120 µl) in dichloromethane (2 ml) and the resulting mixture was stirred at room temperature for three hours. The solvent was removed under reduced pressure and the resulting residue was purified by preparative HPLC (Waters XBridge, gradient of water containing 0.1% NH$_3$ and acetonitrile) to yield 32 mg of a solid (0.09 mmol, 70%).

Example 4

Synthesis of (E)-4,4,4-trifluoro-1-[4-(2-quinolyl)piperazin-1-yl]but-2-en-1-one (A-8)

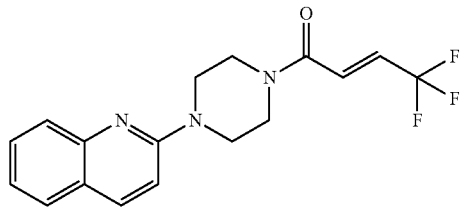 [SMILES: O=C(/C=C/C(F)(F)F)N1CCN(c2ccc3ccccc3n2)CC1]

Step A: tert-Butyl 4-(3-isoquinolyl)piperazine-1-carboxylate

Palladium acetate (63 mg, 0.8 mmol), BINAP (250 mg, 0.4 mmol) and caesium carbonate (1.3 g, 4 mmol) were suspended in anhydrous 1,4-dioxane (9 ml) under an argon atmosphere and sonicated for 40 minutes. 2-Chloroquinoline (343 mg, 2 mmol) and tert-butyl piperazine-1-carboxylate (373 mg, 2 mmol) were dissolved in anhydrous 1,4-dioxane (3 ml) and the resulting solution was added to the catalyst-containing mixture. The resulting mixture was stirred at 110° C. for three hours, cooled to room temperature and diluted with ethyl acetate. The solids were removed by centrifugation and decantation, the supernatant was evaporated to dryness under reduced pressure and the resulting residue was dissolved in DCM and filtered through a silica column. The product was eluted with a mixture of DCM and diethylether. After removal of the solvent under reduced pressure, 201 mg of a solid were obtained (0.64 mmol, 32%) MS (ESI) m/z=314.2 [M+1]$^+$.

Step B: 2-piperazin-1-ylquinoline hydrochloride

To tert-butyl 4-(3-isoquinolyl)piperazine-1-carboxylate (201 mg, 0.64 mmol) was added a 1:1 mixture of DCM and trifluoroacetic acid, the resulting mixture was stirred at room temperature for one hour. The volatiles were removed under reduced pressure, the residue was dissolved in THF and evaporated again. The residue was dissolved in THF and 4N HCl in 1,4-dioxane was added to precipitate the hydrochloride salt which was collected by filtration and dried under reduced pressure. 123 mg of a solid were obtained (0.49 mmol, 77%). MS (APCI) m/z=214.1 [M+1]$^+$.

Step C: (E)-4,4,4-Trifluoro-1-[4-(2-quinolyl)piperazin-1-yl]but-2-en-1-one (E)-4,4,4-Trifluorobut-2-enoic acid (28 mg, 0.2 mmol) was dissolved in dichloromethane (1 ml), oxalyl chloride (18 µl, 0.2 mol) and one drop of DMF were added and the resulting solution was stirred at room temperature for 10 minutes. This solution was added to a solution of 2-piperazin-1-ylquinoline hydrochloride (25 mg, 0.1 mmol) in DMF (0.5 ml). Triethylamine (42 µl, 0.3 mmol) was added and the resulting mixture was stirred at room temperature for two hours. The mixture was diluted with ethylacetate and the resulting mixture was washed with saturated sodium bicarbonate solution, brine and dried (MgSO$_4$). The solvent was removed under reduced pressure and the resulting residue was purified by preparative HPLC (Waters XBridge, gradient of water containing 0.1% NH$_3$ and acetonitrile) to yield 15 mg of a solid (0.046 mmol, 46%).

Example 5

Synthesis of (E)-4,4-difluoro-N-[(3S)-1-(5-methyl-3-pyridyl)pyrrolidin-3-yl]pent-2-enamide (D-15)

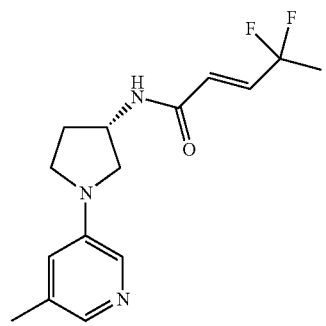 [SMILES: Cc1cncc(N2CC[C@H](NC(=O)/C=C/C(C)(F)F)C2)c1]

Step A: tert-Butyl N-[(3S)-1-(5-methyl-3-pyridyl) pyrrolidin-3-yl]carbamate

A solution of 3-bromo-5-methylpyridine (138 mg, 0.892 mmol), sodium tert-butoxide (154 mg, 1.604 mmol), tert-butyl N-[(3S)-pyrrolidin-3-yl]carbamate (224 mg, 1.203 mmol) and 2-(dicyclohexylphosphino)-2',6'-isopropoxybiphenyl (RuPhos, 37.4 mmol) in anhydrous 1,4-dioxane (7 ml) was purged with argon. Tris(dibenzylideneacetone)dipalladium (0) (Pd$_2$(DBA)$_3$, 73.5 mg, 0.08 mmol) was added and the mixture was stirred at 70° C. for two hours in a closed vial. After cooling to room temperature the mixture was filtered through kieselguhr and concentrated under reduced pressure. The residue was purified by column chromatography (silica, gradient from 0.5 to 7% methanol containing 7N NH3 in dichloromethane (DCM)) to afford 163 mg of a yellow solid (0.588 mmol, 73%) MS (ESI) 278.2 [M+1]$^+$.

Step B: (3S)-1-(4-Methyl-2-pyridyl)pyrrolidin-3-amine trihydrochloride tert-Butyl N-[(3S)-1-(5-methyl-3-pyridyl)pyrrolidin-3-yl] carbamate (230 mg, 0.829 mmol) was dissolved in methanol (1 ml). Hydrochloric acid (4M in dioxane, 4.15 ml, 16.58 mmol) was added slowly and the mixture was stirred at room temperature for two hours. The mixture was concentrated under reduced pressure, the residue was treated with diethylether and evaporated to dryness under reduced pressure. The last step was repeated twice after which 177 mg of a light-brown solid were obtained (0.618 mmol, 74%) MS (ESI) m/z=178.1 [M+1]$^+$.

Step C: (E)-4,4-Difluoro-N-[(3S)-1-(5-methyl-3-pyridyl)pyrrolidin-3-yl]pent-2-enamide (E)-4,4-Difluoropent-2-enoic acid (22 mg, 0.16 mmol) was dissolved in dichloromethane (1 ml), oxalyl chloride (14 µl, 0.16 mol) and one drop of DMF were added and the resulting solution was stirred at room temperature for 15 minutes. This solution was added to a solution of (3S)-1-(4-methyl-2-pyridyl)pyrrolidin-3-amine trihydrochloride (29 mg, 0.1 mmol) in DCM (2 ml). Ethyl-N,N-diisopropylamine (DIPEA, 70 µl, 0.4 mmol) was added and the resulting mixture was stirred at room temperature overnight. The mixture was concentrated under reduced pressure and the resulting residue was purified by preparative HPLC (Waters XBridge, gradient of water containing 0.1% NH$_3$ and acetonitrile) to yield 20 mg of a solid (0.067 mmol, 67%).

Example 6

Synthesis of (E)-4,4,4-trifluoro-1-[3-[(4-methyl-2-pyridyl)amino]azetidin-1-yl]but-2-en-1-one (D-43)

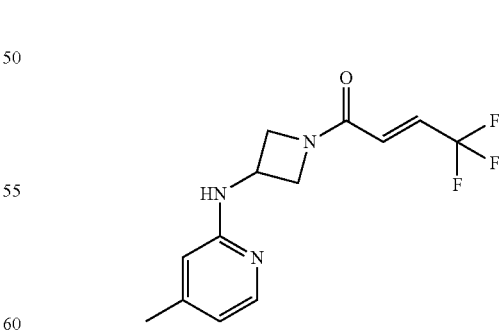

Step A: tert-Butyl 3-[(4-methyl-2-pyridyl)amino] azetidine-1-carboxylate

A solution of 2-bromo-4-methylpyridine (90 mg, 0.523 mmol), sodium tert-butoxide (101 mg, 1.046 mmol), tert-butyl 3-aminoazetidine-1-carboxylate (451 mg, 2.62 mmol) and BINAP (16.3 mg, 0.026 mmol) in anhydrous toluene (7 ml) was purged with argon. Palladium(II)acetate (5.9 mg, 0.026 mmol) was added and the mixture was stirred at 100° C. overnight in a closed vial. After cooling to room temperature the mixture was filtered through kieselguhr and concentrated under reduced pressure. The residue was purified by column chromatography (silica, gradient from 0.5 to 10% ethyl acetate in heptane) to afford 60 mg of a solid (0.228 mmol, 43%) MS (ESI) m/z=264.2 [M+1]$^+$.

Step B: N-(Azetidin-3-yl)-4-methyl-pyridin-2-amine tert-Butyl 3-[(4-methyl-2-pyridyl)amino]azetidine-1-carboxylate (120 mg, 0.456 mmol) was dissolved in DCM (10 ml) under nitrogen. Trifluoroacetic acid (0.843 ml, 11.4 mmol) was added and the mixture was stirred at room temperature overnight. The mixture was concentrated under reduced pressure, the residue was dissolved in methanol and passed through a SCX column. The product was eluted by 2M ammonia in methanol, the solution was evaporated to dryness and the residue was used directly in the next step. MS (ESI) m/z=164.1 [M+1]$^+$.

Step C: (E)-4,4,4-Trifluoro-1-[3-[(4-methyl-2-pyridyl)amino]azetidin-1-yl]but-2-en-1-one N-(Azetidin-3-yl)-4-methyl-pyridin-2-amine (the residue from step B) was dissolved in anhydrous DMF (5 ml) under nitrogen and cooled to 0° C. DIPEA (0.416 ml, 2.43 mmol) was added with stirring, followed after five minutes by 1-(3-dimethylaminopropyl)-3-ethylcarbodiimide hydrochloride (EDCI.HCl, 102 mg, 0.534 mmol) and 1-hydroxy-7-azabenzotriazole (6.6 mg, 0.049 mmol). Stirring was continued at room temperature overnight. The mixture was poured into water (20 ml) and extracted with ethyl acetate (4×). The combined organic layers were washed with brine and dried over sodium sulfate. The solvent was removed under reduced pressure and the residue was purified by column chromatography (silica, gradient from 0.5 to 5% methanol in DCM) to yield 27 mg (0.095 mmol, 19%).

Example 7

Synthesis of (E)-4-methyl-1-[4-(4-methyl-2-pyridyl)-1,4-diazepan-1-yl]pent-2-en-1-one (D-45)

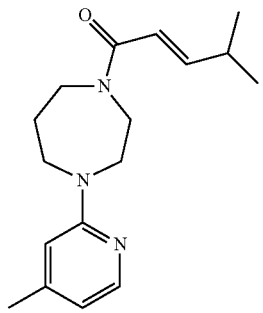 [SMILES: Cc1ccnc(N2CCCN(C(=O)/C=C/C(C)C)CC2)c1]

Step A: tert-Butyl 4-(4-methyl-2-pyridyl)-1,4-diazepane-1-carboxylate

2-Bromo-4-methylpyridine (400 mg, 2.326 mmol), tert-butyl 1,4-diazepane-1-carboxylate (2.1 g, 10.5 mmol) and potassium carbonate (2.8 g, 20 mmol) were combined in anhydrous DMF (20 ml) and heated under microwave heating at 140° C. for 5 hours. The mixture was poured into water and extracted with ethyl acetate (4×). The combined organic layers were washed with brine (2×) and dried over sodium sulfate. The solvent was removed under reduced pressure and the residue was purified two times by column chromatography (silica, gradient from 0 to 50% ethyl acetate in heptane) to yield 97 mg (0.33 mmol, 14%). MS (ESI) m/z=292.2 [M+1]$^+$.

Step B: 1-(4-Methyl-2-pyridyl)-1,4-diazepane dihydrochloride tert-Butyl 4-(4-methyl-2-pyridyl)-1,4-diazepane-1-carboxylate (91 mg, 0.312 mmol) was dissolved in DCM under nitrogen. Hydrochloric acid (4N in dioxane, 1.56 ml, 6.25 mmol) was added and the mixture was stirred at room temperature overnight. The mixture was evaporated under reduced pressure to give 84 mg of a solid (quantitative). MS (ESI) m/z=192.2 [M+1]$^+$.

Step C: (E)-4-Methyl-1-[4-(4-methyl-2-pyridyl)-1,4-diazepan-1-yl]pent-2-en-1-one (E)-4-Methylpent-2-enoic acid (26 mg, 0.23 mmol) was dissolved in dichloromethane (1 ml), oxalyl chloride (20 µl, 0.23 mol) and one drop of DMF were added and the resulting solution was stirred at room temperature for 15 minutes. This solution was added to a solution of 1-(4-methyl-2-pyridyl)-1,4-diazepane dihydrochloride (40 mg, 0.15 mmol) in DCM (2 ml). DIPEA (80 µl, 0.5 mmol) was added and the resulting mixture was stirred at room temperature overnight. The mixture was concentrated under reduced pressure and the resulting residue was purified by preparative HPLC (Waters XBridge, gradient of water containing 0.1% NH$_3$ and acetonitrile) to yield 13 mg of a solid (0.047 mmol, 20%).

Example 8

Synthesis of (E)-4,4-difluoro-1-[(3R)-3-[(4-methyl-2-pyridyl)amino]-1-piperidyl]pent-2-en-1-one (D-18)

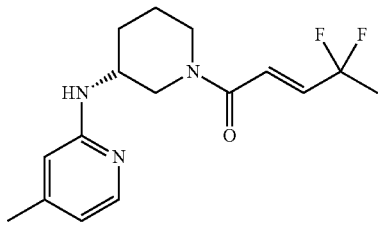

Step A: tert-Butyl (3R)-3-[(4-methyl-2-pyridyl)amino]piperidine-1-carboxylate

3-Bromo-5-methylpyridine (200 mg, 1.163 mmol), sodium tert-butoxide (223 mg, 2.325 mmol), tert-butyl (3R)-3-aminopiperidine-1-carboxylate (349 mg, 1.744 mmol) and BrettPhos (31.2 mg, 0.058 mmol) in anhydrous dioxane (10 ml) was purged with argon. Pd$_2$(DBA)$_3$ (53.2 mg, 0.058 mmol) was added and the mixture was stirred at 70° C. for two hours. After cooling to room temperature the mixture was filtered through kieselguhr, the filtrate was concentrated under reduced pressure and the residue was purified by column chromatography (silica, gradient from 0.5 to 10% methanol containing 7N $NH_3$ in DCM) to yield 271 mg of an orange solid (0.93 mmol, 64%) MS (ESI) m/z=292.2 [M+1]+.

Step B:
4-Methyl-N-[(3R)-3-piperidyl]pyridin-2-amine dihydrochloride tert-Butyl (3R)-3-[(4-methyl-2-pyridyl)amino]piperidine-1-carboxylate (271 mg, 0.93 mmol) was dissolved in methanol (1 ml). Hydrochloric acid (4N in dioxane, 4.65 ml, 18.6 mmol) was added and the mixture was stirred at room temperature for three hours. The mixture was concentrated under reduced pressure, the residue was treated twice with diethylether and separated by decantation, dissolved in methanol and evaporated to dryness to yield 246 mg (quantitative) MS (ESI) m/z=192.2 [M+1]+.

Step C: (E)-4,4-Difluoro-1-[(3R)-3-[(4-methyl-2-pyridyl)amino]-1-piperidyl]pent-2-en-1-one (E)-4,4-Difluoropent-2-enoic acid (22 mg, 0.16 mmol) was dissolved in dichloromethane (1 ml), oxalyl chloride (14 µl, 0.16 mol) and one drop of DMF were added and the resulting solution was stirred at room temperature for 15 minutes. This solution was added to a solution of 4-methyl-N-[(3R)-3-piperidyl]pyridin-2-amine dihydrochloride (23 mg, 0.087 mmol) in DCM (2 ml). Ethyl-N,N-diisopropylamine (DIPEA, 70 µl, 0.4 mmol) was added and the resulting mixture was stirred at room temperature overnight. The mixture was concentrated under reduced pressure and the resulting residue was purified by preparative HPLC (Waters X-bridge, gradient of water containing 0.1% $NH_3$ and acetonitrile) to yield 13 mg of a solid (0.042 mmol, 48%).

Example 9

Synthesis of (E)-4-methyl-1-[(1S,4S)-5-(2-methyl-3-pyridyl)-2,5-diazabicyclo[2.2.1]heptan-2-yl]pent-2-en-1-one (C-4)

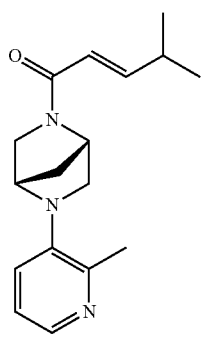 [SMILES: Cc1ncccc1N1C[C@@H]2C[C@H]1CN2C(=O)/C=C/C(C)C]

Step A: tert-Butyl (1S,4S)-5-(2-methyl-3-pyridyl)-2,5-diazabicyclo[2.2.1]heptane-2-carboxylate 3-Bromo-2-methylpyridine (258 mg, 1.5 mmol), tert-butyl (1S,4S)-3,6-diazabicyclo[2.2.1]heptane-3-carboxylate (397 mg, 2 mmol), $Pd_2(DBA)_3$ (30 mg, 0.033 mmol), sodium tert-butoxide (160 mg, 1.66 mmol), BINAP (60 mg, 0.096 mmol) were placed in anhydrous THF (5 ml), purged with argon and heated under microwave heating at 80° C. in a closed vial for 40 minutes. The mixture was filtered through kieselguhr, concentrated under reduced pressure and purified by column chromatography (silica, gradient from 0 to 50% ethyl acetate in DCM) to yield 230 mg of an orange solid (0.80 mmol, yield 53%). MS (ESI) m/z=290.1 [M+1]+.

Step B: (1S,4S)-5-(2-Methyl-3-pyridyl)-2,5-diazabicyclo[2.2.1]heptane hydrochloride tert-Butyl (1S,4S)-5-(2-methyl-3-pyridyl)-2,5-diazabicyclo[2.2.1]heptane-2-carboxylate (230 mg, 0.8 mmol) was dissolved in a mixture of DCM (5 ml) and trifluoroacetic acid (5 ml) and stirred at room temperature overnight. The mixture was concentrated under reduced pressure, the residue was dissolved in DCM and evaporated again. The last step was repeated, the residue was dissolved in THF (10 ml) and hydrochloric acid was added (4N in dioxane, 4 ml). The precipitate was isolated by centrifugation and decantation, washed with THF (2×) and dried under reduced pressure to yield 170 mg of a brown solid (0.75 mmol, yield 94%) MS (ESI) m/z=190.1 [M+1]+.

Step C: (E)-4-Methyl-1-[(1S,4S)-5-(2-methyl-3-pyridyl)-2,5-diazabicyclo[2.2.1]heptan-2-yl]pent-2-en-1-one (E)-4-Methylpent-2-enoic acid (57 mg, 0.5 mmol) was dissolved in dichloromethane (2 ml), oxalyl chloride (42 µl, 0.5 mmol) and one drop of DMF were added and the resulting solution was stirred at room temperature for 15 minutes. This solution was added to a solution of (1S,4S)-5-(2-methyl-3-pyridyl)-2,5-diazabicyclo[2.2.1]heptane hydrochloride (66 mg, 0.3 mmol) in DCM (2 ml). DIPEA (175 µl, 1 mmol) was added and the resulting mixture was stirred at room temperature overnight. The mixture was concentrated under reduced pressure and the resulting residue was purified by preparative HPLC (Waters XBridge, gradient of water containing 0.1% $NH_3$ and acetonitrile) to yield 59 mg of a solid (0.21 mmol, 69%).

Example 10

Synthesis of 1-(4-methyl-2-pyridyl)-4-[(E)-3,3,4,4,4-pentafluorobut-1-enyl]sulfonyl-piperazine (A-62)

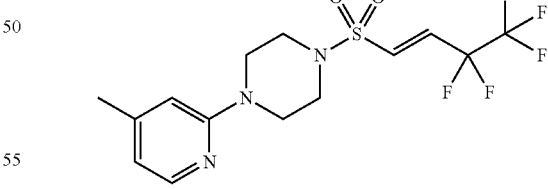

Step A:
1-(4-Methyl-2-pyridyl)-4-methylsulfonyl-piperazine

To a cooled (0° C.) solution of 1-(4-methyl-2-pyridyl)piperazine (228 mg, 1.286 mmol) in DCM (10 ml) were added triethylamine (360 µl, 2.59 mmol) and methanesulfonyl chloride (105 µl, 2.59 mmol). The mixture was stirred at 0° C. for one hour, then a saturated solution of sodium bicarbonate was added, the layers were separated, the aqueous layer was extracted with DCM (2×), the organic layers were combined, dried (sodium sulfate) and concentrated under reduced pressure to yield 316 mg of a white solid (1.238 mmol, yield 96%) MS (ESI) m/z=256.1 [M+1]⁺.

Step B: 1-(Diethoxyphosphorylmethylsulfonyl)-4-(4-methyl-2-pyridyl)piperazine 1-(4-Methyl-2-pyridyl)-4-methylsulfonyl-piperazine (1.16 g, 4.54 mmol) was dissolved in anhydrous THF (80 ml) and cooled under nitrogen to −78° C. Lithium bis(trimethylsilyl)amide (1M in THF, 14 ml, 14 mmol) was added dropwise and the mixture was stirred at −78° C. for one hour. Diethyl chlorophosphate (3.1 g, 18 mmol) was added dropwise and stirring was continued for one hour at −78° C., after which the mixture was allowed to reach room temperature over three hours. A saturated solution of ammonium chloride was added and the mixture was extracted with DCM (3×), the combined organic layers were dried (sodium sulfate), concentrated under reduced pressure and the residue was purified by column chromatography (silica, gradient from 0 to 6% methanol in DCM) to give 1.44 g of a light-brown oil (3.68 mmol, yield 81%) MS (ESI) m/z=392.1 [M+1]⁺.

Step C: 1-(4-Methyl-2-pyridyl)-4-[(E)-3,3,4,4,4-pentafluorobut-1-enyl]sulfonyl-piperazine To a solution of 1-(diethoxyphosphorylmethylsulfonyl)-4-(4-methyl-2-pyridyl)piperazine (242 mg, 0.618 mmol) in anhydrous THF (25 ml) were added molsieves 4A and sodium hydride (60%, 38 mg, 0.95 mmol) under nitrogen and the mixture was stirred at room temperature for 10 minutes. The mixture was cooled to 0° C. and 2,2,3,3,3-pentafluoro-1-methoxy-propan-1-ol (300 mg, 1.67 mmol) was added. The mixture was stirred at 0° C. for 30 minutes and then allowed to reach room temperature over one hour. The mixture was filtered through kieselguhr, concentrated under reduced pressure and the residue was purified by column chromatography (reveleris, gradient from 0 to 100% ethyl acetate in n-heptane) to yield 130 mg (0.337 mmol, yield 55%).

Example 11

Synthesis of (E)-4-methyl-1-[4-(2-methyl-3-pyridyl)-1-piperidyl]pent-2-en-1-one (A-100)

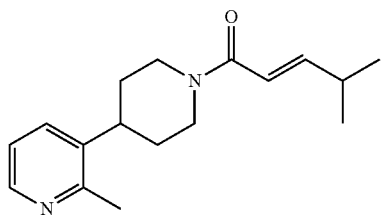 [SMILES: Cc1ncccc1C1CCN(C(=O)/C=C/C(C)C)CC1]

Step A: tert-Butyl 4-(2-methyl-3-pyridyl)-3,6-dihydro-2H-pyridine-1-carboxylate

3-Bromo-2-methylpyridine (172 mg, 1 mmol) and tert-butyl 4-(4,4,5,5-tetramethyl-1,3,2-dioxaborolan-2-yl)-3,6-dihydro-2H-pyridine-1-carboxylate (309 mg, 1 mmol) were dissolved in THF (10 ml) and combined with a solution of sodium carbonate (425 mg, 4 mmol) in water (1 ml). The mixture was purged with argon, PdCl₂(PPh₃)₂ (35 mg, 0.05 mmol) was added and the mixture was stirred under reflux for three days, diluted with ethyl acetate (30 ml), the phases were separated and the organic layer was washed with brine and dried (sodium sulfate). After concentration under reduced pressure the residue was purified with column chromatography (silica, gradient of 0 to 30% ethyl acetate in DCM) to yield 209 mg (0.76 mmol, yield 76%) MS (multi-mode) m/z=275.2 [M+1]⁺.

Step B: tert-Butyl 4-(2-methyl-3-pyridyl)piperidine-1-carboxylate tert-Butyl 4-(2-methyl-3-pyridyl)-3,6-dihydro-2H-pyridine-1-carboxylate (209 mg, 0.76 mmol) was dissolved in ethanol (42 ml) and hydrogenated in a H-cube hydrogen generator with a flow of 1 ml/min and at a temperature of 70° C. The mixture was evaporated under reduced pressure, the residue was purified by preparative HPLC (Waters X-Bridge, gradient of water containing 0.1% NH₃ and acetonitrile) to yield 100 mg of a colourless solid (0.36 mmol, yield 47%). MS (ESI) m/z=277.2 [M+1]⁺.

Step C: 2-Methyl-3-(4-piperidyl)pyridine hydrochloride tert-Butyl 4-(2-methyl-3-pyridyl)piperidine-1-carboxylate (100 mg, 0.36 mmol) was dissolved in methanol (4 ml) and combined with hydrochloric acid (4N in dioxane, 10 ml) and the mixture was stirred at room temperature for two hours. The volatiles were removed under reduced pressure to yield 54 mg of a beige solid (0.25 mmol, 69%) MS (ESI) m/z=177.1 [M+1]⁺.

Step D: (E)-4-Methyl-1-[4-(2-methyl-3-pyridyl)-1-piperidyl]pent-2-en-1-one (E)-4-Methylpent-2-enoic acid (26 mg, 0.23 mmol) was dissolved in dichloromethane (1 ml), oxalyl chloride (20 µl, 0.23 mmol) and one drop of DMF were added and the resulting solution was stirred at room temperature for 15 minutes. This solution was added to a solution of 2-methyl-3-(4-piperidyl)pyridine hydrochloride (27 mg, 0.125 mmol) in DCM (2 ml). DIPEA (120 µl, 0.7 mmol) was added and the resulting mixture was stirred at room temperature overnight. The mixture was concentrated under reduced pressure and the resulting residue was purified by preparative HPLC (Waters XBridge, gradient of water containing 0.1% NH₃ and acetonitrile) to yield 9.6 mg of a white solid (0.035 mmol, 15%).

Example 12

Synthesis of (E)-4-methyl-1-[1-(4-methyl-2-pyridyl)-4-piperidyl]pent-2-en-1-one (A-68)

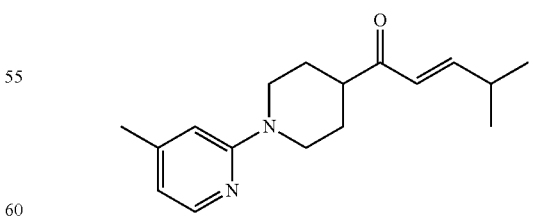

Step A: Ethyl 1-(4-methyl-2-pyridyl)piperidine-4-carboxylate

2-Bromo-4-methylpyridine (860 mg, 5 mmol), ethyl piperidine-4-carboxylate (865 mg, 5.5 mmol) and DIPEA (958

µl, 5.5 mmol) were mixed in dipropyleneglycolmonomethylether (10 ml) and stirred at 150° C. overnight. Additional ethyl piperidine-4-carboxylate (865 mg, 5.5 mmol) was added and stirring was continued at 150° C. for 24 hours. The mixture was concentrated under reduced pressure and the residue was purified by column chromatography (silica, gradient from 0 to 30% ethyl acetate in DCM) to give 700 mg of a brown solid (2.8 mmol, 56%) MS (multi-mode) m/z=249.1 [M+1]$^+$.

Step B: 2-Diethoxyphosphoryl-1-[1-(4-methyl-2-pyridyl)-4-piperidyl]ethanone

Diethyl methylphosphonate (1.27 g, 8.36 mmol) was dissolved in anhydrous THF (7 ml), the solution was purged with argon and cooled to −78° C. n-Butyllithium (2M in hexane, 2.67 ml, 5.34 mmol) was added at such a rate that the temperature remained below −65° C. After addition was complete, stirring was continued for 20 minutes, then a solution of ethyl 1-(4-methyl-2-pyridyl)piperidine-4-carboxylate (626 mg, 2.52 mmol) in anhydrous THF (1 ml) was added dropwise so that the temperature remained below −70° C. Stirring was continued overnight while the temperature was allowed to reach room temperature. The mixture was neutralized with glacial acetic acid, concentrated under reduced pressure, water was added and the mixture was extracted with DCM (3×). The combined organic phases were dried (sodium sulfate), and concentrated under reduced pressure to give a brown oil that was used directly in the next step MS (multi-mode) m/z=355.1 [M+1]$^+$.

Step C: (E)-4-Methyl-1-[1-(4-methyl-2-pyridyl)-4-piperidyl]pent-2-en-1-one

2-Diethoxyphosphoryl-1-[1-(4-methyl-2-pyridyl)-4-piperidyl]ethanone (product of step B, 350 mg, 1 mmol) was dissolved in anhydrous THF (40 ml) and cooled under argon to 0° C. Sodium hydride (60%, 60 mg, 1.5 mmol) was added and the mixture was stirred at room temperature for 20 minutes. Isobutyryl aldehyde (186 µl, 2 mmol) was added and stirring was continued for 90 minutes. The mixture was poured into saturated ammonium chloride solution (100 ml), the mixture was extracted with DCM, the aqueous layer was extracted again with DCM (2×), and the combined organic phases were dried (sodium sulfate) and concentrated under reduced pressure. The residue was purified by preparative HPLC (Waters XBridge, gradient of water containing 0.1% NH$_3$ and acetonitrile) to yield 30 mg of a brown solid (0.11 mmol, 11%).

Example 13

Synthesis of ethyl 5-methylamino-2-[4-[(E)-4,4,4-trifluorobut-2-enoyl]piperazin-1-yl]thiazole-4-carboxylate (B-32)

Step A: Ethyl 2-(4-tert-butoxycarbonylpiperazin-1-yl)-5-methylamino-thiazole-4-carboxylate To a solution of ethyl 2-bromo-5-methylamino-thiazole-4-carboxylate (401 mg, 1.512 mmol) and tert-butyl piperazine-1-carboxylate (1.06 g, 5.69 mmol) in anhydrous dioxane (15 ml) was added DIPEA (2 ml, 11.5 mmol) and the reaction was heated at 100° C. in a sealed flask for 23 hours. The mixture was cooled to room temperature, partitioned between DCM and sat. sodium bicarbonate solution and the phases were separated. The aqueous layer was extracted twice with DCM and the combined organic layers were dried (sodium sulfate) and concentrated under reduced pressure. The residue was purified by column chromatography (silica, gradient from 10 to 70% ethyl acetate in n-heptane) to yield 197 mg of a white solid (0.532 mmol, yield 35%) MS (multi-mode) m/z=371.2 [M+1]$^+$.

Step B: Ethyl 5-methylamino-2-piperazin-1-yl-thiazole-4-carboxylate hydrochloride Ethyl 2-(4-tert-butoxycarbonylpiperazin-1-yl)-5-methylamino-thiazole-4-carboxylate (196 mg, 0.529 mmol) was dissolved in a mixture of diethylether (10 ml) and ethanol (absolute, 15 ml), hydrochloric acid (4N in dioxane, 5 ml) was added and the mixture was stirred at room temperature for two days. The resulting precipitate was collected by filtration, washed with diethylether and dried under reduced pressure to give 130 mg of a white solid (0.424 mmol, yield 80) MS (multi-mode) m/z=271.1 [M+1]$^+$.

Step C: Ethyl 5-methylamino-2-[4-[(E)-4,4,4-trifluorobut-2-enoyl]piperazin-1-yl]thiazole-4-carboxylate (E)-4,4,4-Trifluorobut-2-enoic acid (25 mg, 0.18 mmol) was dissolved in dichloromethane (1 ml), oxalyl chloride (16 µl, 0.18 mol) and one drop of DMF were added and the resulting solution was stirred at room temperature for 10 minutes. This solution was added to a solution of ethyl 5-methylamino-2-piperazin-1-yl-thiazole-4-carboxylate hydrochloride (41 mg, 0.15 mmol) and DIPEA (79 µl, 0.45 mmol) in anhydrous DCM (2 ml) and the resulting mixture was stirred at room temperature overnight. The mixture was concentrated under reduced pressure and the resulting residue was purified by preparative HPLC (Waters Xbridge, gradient of water containing 0.1% NH$_3$ and acetonitrile) to yield 7 mg of a solid (0.017 mmol, 11%).

Example 14

5-Chloro-4,6-dimethyl-2-[4-[(E)-4,4,4-trifluorobut-2-enoyl]piperazin-1-yl]pyridine-3-carbonitrile (A-127)

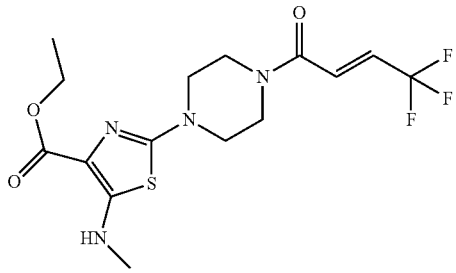 [SMILES: CCOC(=O)c1nc(N2CCN(C(=O)/C=C/C(F)(F)F)CC2)sc1NC]

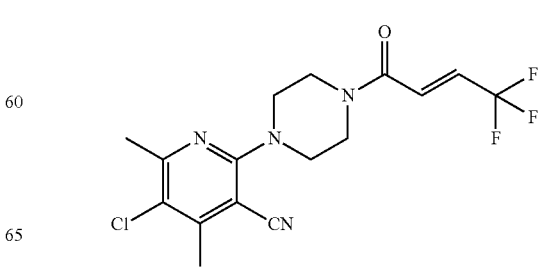

Step A: 5-Chloro-4,6-dimethyl-2-piperazin-1-yl-pyridine-3-carbonitrile

A mixture of 2,5-dichloro-4,6-dimethylnicotinonitrile (200 mg, 0.995 mmol), K$_2$CO$_3$ (275 mg, 1.990 mmol) and piperazine (5141 mg, 59.7 mmol) was heated under microwave heating at 120° C. for 15 minutes. After cooling to room temperature the mixture was partitioned between 1N HCl and DCM. The layers were separated and the aqueous layer was extracted once with DCM, basified with NaOH (4N) and extracted with DCM (4×). The combined organic layers were dried (sodium sulfate) and concentrated under reduced pressure to give 231 mg of a solid (0.922 mmol, yield 93%) MS (multi-mode) m/z=251.2 [M+1]$^+$.

Step B: 5-Chloro-4,6-dimethyl-2-[4-[(E)-4,4,4-trifluorobut-2-enoyl]piperazin-1-yl]pyridine-3-carbonitrile (E)-4,4,4-Trifluorobut-2-enoic acid (25 mg, 0.18 mmol) was dissolved in dichloromethane (1 ml), oxalyl chloride (16 µl, 0.18 mol) and one drop of DMF were added and the resulting solution was stirred at room temperature for 10 minutes. This solution was added to a solution of 5-chloro-4,6-dimethyl-2-piperazin-1-yl-pyridine-3-carbonitrile (38 mg, 0.15 mmol) and DIPEA (79 µl, 0.45 mmol) in anhydrous DCM (2 ml) and the resulting mixture was stirred at room temperature overnight. The mixture was concentrated under reduced pressure and the resulting residue was purified by preparative HPLC (Waters XBridge, gradient of water containing 0.1% NH$_3$ and acetonitrile) to yield 2.7 mg of a solid (0.007 mmol, 5%).

Example 15

Synthesis of N,N-dimethyl-6-[4-[(E)-4,4,4-trifluorobut-2-enoyl]piperazin-1-yl]pyridine-3-carboxamide (A-96)

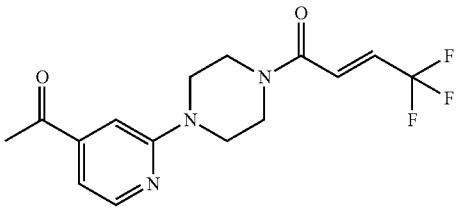

Step A: N,N-Dimethyl-6-piperazin-1-yl-pyridine-3-carboxamide

A solution of 6-chloro-N,N-dimethylnicotinamide (250 mg, 1.354 mmol), piperazine (584 mg, 6.77 mmol), sodium tert-butoxide (260 mg, 2.71 mmol) and BrettPhos (36 mg, 0.068 mmol) in anhydrous 1,4-dioxane (7 ml) was purged with argon. Next, Pd$_2$(DBA)$_3$ (62 mg, 0.068 mmol) was added and the mixture was heated in a closed vial to 70° C. for 2 hours, then heating was turned off and the mixture was stirred at room temperature for 3 days. The mixture was filtered through kieselguhr, the filter was washed with ethyl acetate, the combined filtrates were concentrated under reduced pressure and the residue was purified by repeated column chromatography (silica, gradient from 1 to 10% methanol containing 7N ammonia in DCM) to yield 158 mg of a solid (0.674 mmol, 50% yield) MS (multi-mode) m/z=235.2 [M+1]$^+$.

Step B: N,N-Dimethyl-6-[4-[(E)-4,4,4-trifluorobut-2-enoyl]piperazin-1-yl]pyridine-3-carboxamide (E)-4,4,4-Trifluorobut-2-enoic acid (32 mg, 0.23 mmol) was dissolved in dichloromethane (1 ml), oxalyl chloride (20 µl, 0.23 mol) and one drop of DMF were added and the resulting solution was stirred at room temperature for 10 minutes. This solution was added to a solution of N,N-dimethyl-6-piperazin-1-yl-pyridine-3-carboxamide (35 mg, 0.15 mmol) and DIPEA (80 µl, 0.5 mmol) in anhydrous DCM (2 ml) and the resulting mixture was stirred at room temperature overnight. The mixture was concentrated under reduced pressure and the resulting residue was purified by preparative HPLC (Waters XBridge, gradient of water containing 0.1% NH$_3$ and acetonitrile) to yield 39 mg of a solid (0.11 mmol, yield 48%).

Example 16

Synthesis of (E)-1-[4-(4-Acetyl-2-pyridyl)piperazin-1-yl]-4,4,4-trifluoro-but-2-en-1-one (A-137)

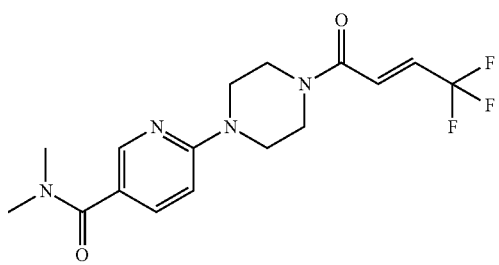 [SMILES: CN(C)C(=O)c1ccc(N2CCN(C(=O)/C=C/C(F)(F)F)CC2)nc1]

Step A: 1-(2-piperazin-1-yl-4-pyridyl)ethanone 1-(2-Chloro-4-pyridyl)ethanone (156 mg, 1 mmol), piperazine (861 mg, 10 mmol) and pyridine (5 ml) were placed in a Radley vial and heated at reflux overnight. The mixture was concentrated under reduced pressure to dryness, the residue was mixed with toluene and evaporated under reduced pressure to remove excess of piperazine. The last step was repeated several times. The residue was purified by preparative HPLC (Waters XBridge, gradient of water containing 0.1% NH$_3$ and acetonitrile) to yield 51 mg of a solid (0.21 mmol, yield 21%) MS (multi-mode) m/z=206.2 [M+1]$^+$.

Step B: (E)-1-[4-(4-Acetyl-2-pyridyl)piperazin-1-yl]-4,4,4-trifluoro-but-2-en-1-one (E)-4,4,4-Trifluorobut-2-enoic acid (34 mg, 0.24 mmol) was dissolved in dichloromethane (1 ml), oxalyl chloride (21 µl, 0.24 mmol) and one drop of DMF were added and the resulting solution was stirred at room temperature for 10 minutes. This solution was added to a solution of 1-(2-piperazin-1-yl-4-pyridyl)ethanone (41 mg, 0.2 mmol) and DIPEA (105 µl, 0.6 mmol) in anhydrous DCM (2 ml) and the resulting mixture was stirred at room temperature overnight. The mixture was concentrated under reduced pressure and the resulting residue was purified by preparative HPLC (Waters

Example 17

Synthesis of (E)-4,4,4-trifluoro-1-[4-(4-methyl-2-pyridyl)piperazin-1-yl]but-2-ene-1-thione (A-57)

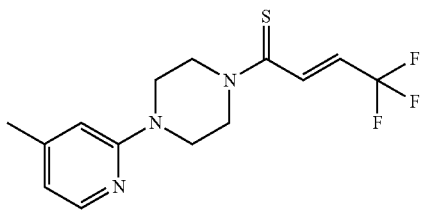 [SMILES: Cc1ccnc(N2CCN(C(=S)/C=C/C(F)(F)F)CC2)c1]

Step A: (E)-4,4,4-Trifluoro-1-[4-(4-methyl-2-pyridyl)piperazin-1-yl]but-2-en-1-one (E)-4,4,4-Trifluorobut-2-enoic acid (28 mg, 0.2 mmol) was dissolved in dichloromethane (1 ml), oxalyl chloride (20 μl, 0.2 mmol) was added and the resulting solution was stirred at room temperature for 5 minutes. This solution was added to a solution of 1-(4-methyl-2-pyridyl)piperazine (36 mg, 0.2 mmol) and TEA (42 μl, 0.3 mmol) in anhydrous DMF (0.5 ml) and the resulting mixture was stirred at room temperature for one hour. The mixture was diluted with ethyl acetate, washed with sat. sodium bicarbonate solution, brine, dried (magnesium sulfate) and concentrated under reduced pressure. The residue was used directly in the next step. MS (multi-mode) m/z=300.1 [M+1]$^+$.

Step B: (E)-4,4,4-Trifluoro-1-[4-(4-methyl-2-pyridyl)piperazin-1-yl]but-2-ene-1-thione The residue of step A was dissolved in anhydrous THF (2 ml), Lawesson's reagent (40 mg, 0.2 mmol) was added and the mixture was stirred at 110° C. in closed vial under microwave heating. The mixture was concentrated under reduced pressure and the residue was purified by preparative HPLC (Waters X-Bridge, gradient of water containing 0.1% NH$_3$ and acetonitrile) to yield 12 mg of a solid (0.039 mmol, yield 20% for two steps).

Example 18

Synthesis of (E)-1-[4-(6-ethoxy-4-methyl-2-pyridyl)piperazin-1-yl]-4,4,4-trifluoro-but-2-en-1-one (A-70)

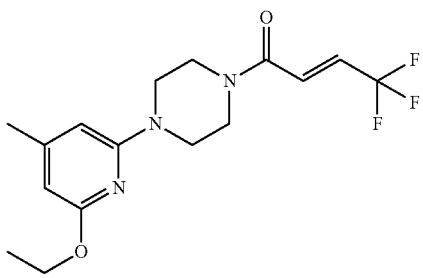 [SMILES: CCOc1cc(C)cc(N2CCN(C(=O)/C=C/C(F)(F)F)CC2)n1]

Step A: tert-Butyl 4-(6-fluoro-4-methyl-2-pyridyl)piperazine-1-carboxylate

2-Bromo-6-fluoro-4-methylpyridine (380 mg, 2 mmol), tert-butyl piperazine-1-carboxylate (466 mg, 2.5 mmol), Pd$_2$(DBA)$_3$ (40 mg, 0.044 mmol), sodium tert-butoxide (317 mg, 3.3 mmol) and BINAP (80 mg, 0.032 mmol) were dissolved in anhydrous THF (6 ml) under argon and heated at 80° C. under microwave heating. The mixture was diluted with ethyl acetate, filtered, the filtrate was evaporated under reduced pressure. The residue was dissolved in DCM and filtered through a pad of silica. The silica was washed with a mixture of DCM and diethylether, the combined filtrates were concentrated under reduced pressure to yield 360 mg (1.22 mmol, yield 61%) MS (multi-mode) m/z=296.2 [M+1]$^+$.

Step B: 1-(6-Fluoro-4-methyl-2-pyridyl)piperazine hydrochloride tert-Butyl 4-(6-fluoro-4-methyl-2-pyridyl)piperazine-1-carboxylate (360 mg, 1.22 mmol) was dissolved in a mixture of DCM (20 ml) and trifluoroacetic acid (5 ml) and stirred at room temperature for 2 hours. The mixture was concentrated under reduced pressure, dissolved in THF, evaporated again and again dissolved in THF. Hydrochloric acid (4N in dioxan) was added, the precipitate was collected by filtration, washed with THF and dried under reduced pressure to give 265 mg of a solid (1.14 mmol, yield 93%) MS (multi-mode) m/z=196.1 [M+1]$^+$.

Step C: 1-(6-Ethoxy-4-methyl-2-pyridyl)piperazine 1-(6-Fluoro-4-methyl-2-pyridyl)piperazine hydrochloride (80 mg, 0.34 mmol) was dissolved in anhydrous ethanol (1.5 ml), sodium (50 mg, 1.96 mmol) was added and the mixture was stirred for five minutes at room temperature and then at 140° C. for one hour under microwave heating in a closed vial. The mixture was filtered through kieselguhr, the filtrate was concentrated under reduced pressure and the residue was treated with acetonitrile and then ethylacetate. The liquids were separated from solids by centrifugation and decanting and the combined supernatants were concentrated under reduced pressure to give 85 mg of a solid (quantitative). MS (multi-mode) m/z=222.2 [M+1]$^+$.

Step D: (E)-1-[4-(6-Ethoxy-4-methyl-2-pyridyl)piperazin-1-yl]-4,4,4-trifluoro-but-2-en-1-one (E)-4,4,4-Trifluorobut-2-enoic acid (17 mg, 0.12 mmol) was dissolved in dichloromethane (1 ml), oxalyl chloride (11 μl, 0.12 mmol) was added and the resulting solution was stirred at room temperature for 10 minutes. This solution was added to a solution of 1-(6-ethoxy-4-methyl-2-pyridyl)piperazine (26 mg, 0.12 mmol) and TEA (42 μl, 0.3 mmol) in anhydrous DMF (0.5 ml) and the resulting mixture was stirred at room temperature for one hour. The mixture was diluted with ethyl acetate, washed with sat. sodium bicarbonate solution, brine, dried (magnesium sulfate) and concentrated under reduced pressure. The residue was purified by preparative HPLC (Waters XBridge, gradient of water containing 0.1% NH$_3$ and acetonitrile) to yield 12 mg of a solid (0.036 mmol, yield 30%).

---

XBridge, gradient of water containing 0.1% NH$_3$ and acetonitrile) to yield 37 mg of a solid (0.108 mmol, yield 47%).

Example 19

Synthesis of (E)-4,4,4-trifluoro-1-[4-(2-methyl-1-oxo-3-pyridyl)piperazin-1-yl]but-2-en-1-one (E-2)

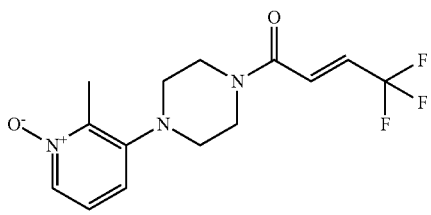 [SMILES: Cc1c(N2CCN(C(=O)/C=C/C(F)(F)F)CC2)ccc[n+]1[O-]]

Step A: 3-Bromo-2-methyl-pyridine 1-oxide

To a solution of 3-bromo-2-methylpyridine (5 g, 29.1 mmol) in DCM (50 ml) was added portionwise at 0° C. m-chloroperbenzoic acid (70%, 8.6 g, 34.9 mmol). The solution was stirred at 0° C. for three hours and then at room temperature overnight. The mixture was filtered, the residue was washed with DCM and the combined DCM phases were quenched with a 10% solution of sodium thiosulfate. The phases were separated, the organic phase was washed with a saturated solution of sodium bicarbonate and brine, dried (sodium sulfate) and concentrated under reduced pressure. The residue was purified by column chromatography (silica, diethyl ether, then DCM/methanol 95:5) to yield 4.44 g (23.6 mmol, yield 81%) MS (multi-mode) m/z=190.0 [M+1]$^+$.

Step B: 2-Methyl-3-piperazin-1-yl-pyridine 1-oxide

3-Bromo-2-methyl-pyridine 1-oxide (a total of 388 mg, 2.06 mmol), sodium tert-butoxide (a total of 392 mg, 4.08 mmol), piperazine (a total of 651 mg, 7.56 mmol) and RuPhos (a total of 58 mg, 0.12 mmol) were divided in three batches and dissolved in anhydrous dioxane (total volume of 15 ml), and purged with argon for 5 minutes. A total of Pd$_2$(DBA)$_3$ (60 mg, 0.064 mmol) was added and each batch was heated in a closed vial for 22 hours at 90° C. The combined reaction mixtures were filtered through kieselguhr and concentrated under reduced pressure to give a brown oil that was purified by column chromatography (silica, gradient from 0 to 10% of methanol containing 7N ammonia in DCM) to give 170 mg (0.88 mmol, yield 43%) MS (multi-mode) m/z=194.1 [M+1]$^+$.

Step C: (E)-4,4,4-Trifluoro-1-[4-(2-methyl-1-oxo-3-pyridyl)piperazin-1-yl]but-2-en-1-one To a solution of 2-methyl-3-piperazin-1-yl-pyridine 1-oxide (86 mg, 0.445 mmol) in anhydrous DCM (5 ml) were added (E)-4,4,4-trifluorobut-2-enoic acid (89 mg, 0.635 mmol), 3-(ethyliminomethyleneamino)-N,N-dimethyl-propan-1-amine hydrochloride (96 mg, 0.501 mmol), HOAt (3.9 mg, 0.029 mmol) and DIPEA (155 µl, 0.89 mmol) and the mixture was stirred at room temperature for 3.5 hours. The mixture was concentrated under reduced pressure and the residue was purified by column chromatography (Reveleris, gradient from 0 to 8% of methanol containing 7N ammonia in DCM) to give 103 mg of a solid (0.327 mmol, yield 73%).

Example 20

Synthesis of (E)-1-[4-(4-ethoxy-6-methyl-2-pyridyl)piperazin-1-yl]-4,4,4-trifluoro-but-2-en-1-one (A-107)

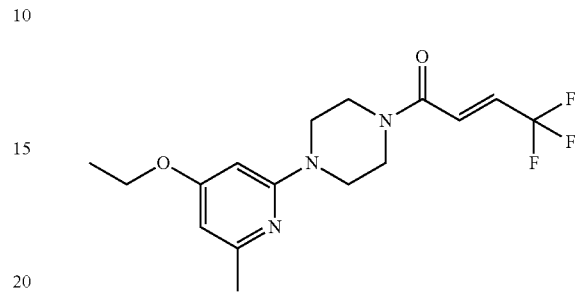

Step A: 2-Bromo-6-methyl-pyridine 1-oxide

2-Bromo-6-methylpyridine (36 g, 0.2 mol) was dissolved in acetic acid (700 ml), hydrogen peroxide (30%, 62 ml, 0.6 mol) was added and the mixture was stirred at 90° C. for 24 hours. After cooling to room temperature, the mixture was diluted with water (700 ml) and extracted with DCM (4×). The combined organic phases were washed with water, dried (sodium sulfate) and concentrated under reduced pressure to give 36 g of a red-brown liquid (0.19 mol, 94%) MS (APCI) m/z=188.0 [M+1]$^+$.

Step B: 2-Bromo-6-methyl-4-nitro-pyridine 1-oxide

To cooled nitric acid (concentrated, 168 ml) was added sulfuric acid (concentrated, 300 ml) under cooling followed by 2-bromo-6-methyl-pyridine 1-oxide (35 g, 0.186 mol). The mixture was stirred at 70° C. for 4 hours, cooled to room temperature and poured slowly on crushed ice. A stream of nitrogen was bubbled through the mixture overnight. The mixture was basified to pH 8 under cooling with NaOH (10N, ca. 1 L), diluted with water (3 L) and extracted with DCM (5×). The combined organic phases were dried (sodium sulfate) and evaporated to dryness to yield 27.6 g of a yellow crystalline solid (0.118 mol, 57%).

Step C: 2-Bromo-6-methyl-4-ethoxy-pyridine 1-oxide

2-Bromo-6-methyl-4-nitro-pyridine 1-oxide (1 g, 4.3 mmol) was dissolved in ethanol (anhydrous, 50 ml), and sodium ethoxide (21% in ethanol, 1.4 ml, 4.3 mmol) was added dropwise with stirring. The mixture was stirred at room temperature overnight, concentrated under reduced pressure, the residue was taken up in DCM (50 ml), the mixture was washed with water (50 ml), dried (sodium sulfate) and concentrated under reduced pressure to yield 0.84 g of brown yellow crystals (3.6 mmol, 84%).

Step D: 2-Bromo-6-methyl-4-ethoxy-pyridine

2-Bromo-6-methyl-4-ethoxy-pyridine 1-oxide (a total of 9.85 g, 42 mmol) was divided in two batches, suspended in ethyl acetate (anhydrous, total of 130 ml), phosphorus trichloride (total of 15 ml) was added dropwise and the mixtures were stirred at 50° C. for three hours. Then the mixture of each batch was poured onto crushed ice (250 ml each) with stirring, ethyl acetate (250 ml each) was added, the phases were separated and the organic phases were washed with water (2 times), dried (magnesium sulfate) and concentrated under reduced pressure. The residues were combined and purified by column chromatography (silica, petrolether/ethyl acetate 95:5) and then by preparative HPLC (Waters XBridge, gradient of water containing 0.1% $NH_3$ and acetonitrile) to give 2.2 g of a yellow oil (10 mmol, 24% yield).

Step E: tert-Butyl 4-(4-ethoxy-6-methyl-2-pyridyl)piperazine-1-carboxylate

2-Bromo-4-ethoxy-6-methylpyridine (108 mg, 0.5 mmol), tert-butyl piperazine-1-carboxylate (140 mg, 0.75 mmol), $Pd_2(DBA)_3$ (10 mg, 0.011 mmol), sodium tert-butoxide (80 mg, 0.825 mmol) and BINAP (20 mg, 0.032 mmol) were placed in anhydrous THF (3 ml) under argon and heated at 80° C. for 30 minutes under microwave heating. The mixture was diluted with ethyl acetate, filtered through kieselguhr and concentrated under reduced pressure. The residue was dissolve in DCM and filtered through a plug of silica. The filter was washed with a mixture of DCM and diethylether, the combined filtrates were concentrated to dryness under reduced pressure to give 141 mg (0.44 mmol, 88% yield) MS (multi-mode) m/z=322.2 $[M+H]^+$.

Step F: 1-(4-Ethoxy-6-methyl-2-pyridyl)piperazine hydrochloride tert-Butyl 4-(4-ethoxy-6-methyl-2-pyridyl)piperazine-1-carboxylate (141 mg, 0.44 mmol) was dissolved in a mixture of DCM (5 ml) and trifluorocrotonic acid (5 ml) and left standing at room temperature for two hours. The mixture was concentrated under reduced pressure, the residue was dissolved in THF, evaporated again, dissolved again in THF. Hydrochloric acid (4N in dioxane) was added to precipitate the product, which was collected by filtration, washed with diethylether and dried under reduced pressure to give 115 mg (quantitative) MS (multi-mode) m/z=222.2 $[M+H]^+$.

Step G: (E)-1-[4-(4-ethoxy-6-methyl-2-pyridyl)piperazin-1-yl]-4,4,4-trifluoro-but-2-en-1-one (E)-4,4,4-Trifluorobut-2-enoic acid (17 mg, 0.12 mmol) was dissolved in dichloromethane (1 ml), oxalyl chloride (11 µl, 0.12 mmol) was added and the resulting solution was stirred at room temperature for 10 minutes. This solution was added to a solution of 1-(4-ethoxy-6-methyl-2-pyridyl)piperazine hydrochloride (22 mg, 0.086 mmol) and TEA (42 µl, 0.3 mmol) in anhydrous DMF (0.5 ml) and the resulting mixture was stirred at room temperature for one hour. The mixture was diluted with ethyl acetate, washed with sat. sodium bicarbonate solution, brine, dried (magnesium sulfate) and concentrated under reduced pressure. The residue was purified by preparative HPLC (Waters X-Bridge, gradient of water containing 0.1% $NH_3$ and acetonitrile) to yield 12 mg of a solid (0.035 mmol, yield 41%).

C. Analytics

HPLC Methods

Method 1
HPLC-MS System:
Agilent LC/MSD Trap 1100 series composed of:
Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm. 2.5µ
Oven: 40° C.
Injection: 2.0 µl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 90 | 10 |
| 4 | 0 | 100 |
| 5 | 0 | 100 |

Run time: 7 min (equilibration included)
Detection Methods:
UV at 254 nm, 210 nm
APCI/MS (80-1000 m/z), positive ions
Comment: Samples diluted in a 1 to 1 mixture of solvents A and B prior to analysis
Method 2
HPLC-MS System:
Agilent LC 1290 Infinity series composed of:
Binary pump G4220A, well plate sampler G4226, thermostat G1330B, diode array detector G4212A, column thermostat G1316C, and single quadrupole mass detector 6130 with multimode ion source.
Chromatographic System:
Column: Waters Xbridge BEH C18, 2.1*50 mm. 2.5µ
Oven: 40° C.
Injection: 0.5 µl
Eluents:
Solvent A: water/ammonia: 99.9/0.1 vol./vol.
Solvent B: acetonitrile/ammonia: 99.9/0.1 vol./vol.
Flow: 0.8 ml/min
Gradient:

| Time [min] | Solvent A [%] | Solvent B [%] |
|---|---|---|
| 0.0 | 98 | 2 |
| 1.2 | 0 | 100 |
| 1.5 | 0 | 100 |

Run time: 2 min (equilibration included)
Detection Methods:
UV at 254 nm, 210 nm
APCI/ES/MS (100-1000 m/z), positive ions
Comment: Samples diluted in a 1 to 1 mixture of solvents A and B prior to analysis
Method 3
HPLC-MS System:
Agilent LC 1290 Infinity series composed of:
Binary pump G4220A, well plate sampler G4226, thermostat G1330B, diode array detector G4212A, column thermostat G1316C, and single quadrupole mass detector 6130 with multimode ion source.
Chromatographic System:
Column: Merck Chromolith fast gradient RP18e, 2.0*50 mm
Oven: 40° C.
Injection: 0.5 µl
Eluents:
Solvent A: water/formic acid: 99.9/0.1 vol./vol.
Solvent B: acetonitrile/formic acid: 99.9/0.1 vol./vol.
Flow: 0.8 ml/min Gradient:

| Time [min] | Solvent A [%] | Solvent B [%] |
| --- | --- | --- |
| 0.0 | 98 | 2 |
| 1.2 | 0 | 100 |
| 1.5 | 0 | 100 |

Run time: 2 min (equilibration included)
Detection Methods:
UV at 254 nm, 210 nm
APCI/ES/MS (100-1000 m/z), positive and negative ions
Comment: Samples diluted in a 1 to 1 mixture of solvents A and B prior to analysis Method 4
HPLC-MS System:
Agilent HPLC/MSD 1100 series composed of:
Binary pump G 1312A included degasser G1379A, well plate sampler G1367A, column oven G1316A, diode array detector G1315B, mass detector G1946D SL with ESI-source and evaporating light detector NQAD (Quant Technologies).
Chromatographic System:
Column: Chromolith FastGradient RP-18e from Merck, 2*50 mm
Oven: 30° C. ambient
Injection: 1.0 μl
Eluents:
Solvent A: water/formic acid: 99.9/0.1 vol./vol.
Solvent B: acetonitrile/formic acid: 99.9/0.1 vol./vol.
Flow: 1.2 ml/min
Gradient:

| Time [min] | Solvent A [%] | Solvent B [%] |
| --- | --- | --- |
| 0.0 | 98 | 2 |
| 0.2 | 98 | 2 |
| 2.2 | 2 | 98 |
| 2.7 | 2 | 98 |

Run time: 3.5 min (equilibration included)
Detection Methods:
   UV at 210 nm and 254 nm
   ESI/MS (100-1000 m/z), positive ions
   ELSD (NQAD)
Comment: Samples diluted in a 1 to 1 mixture of solvents A and B prior to analysis Method 5
HPLC-MS System:
Agilent LC/MSD Trap 1100 series composed of:
Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm. 2.5μ
Oven: 40° C.
Injection: 2.0 μl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
| --- | --- | --- |
| 0.0 | 95 | 5 |
| 5 | 0 | 100 |
| 7 | 0 | 100 |

Run time: 10 min (equilibration included)
Detection Methods:
UV at 254 nm, 210 nm
APCI/MS (100-1500 m/z), positive ions
Comment: Samples diluted in a 1 to 1 mixture of solvents A and B prior to analysis D. Specific Compounds Table A below provides for each of the exemplified compounds of the formula (A) the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis. From compound A-142 until to the end of the table the methods by which the compounds are synthesized are identified by referring to the synthesis steps described in the synthesis examples of paragraph B above ("Synthesis Examples").

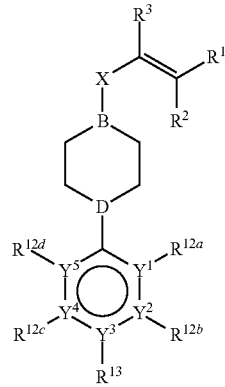

Formula (A)

TABLE A ($Y^3$ = C)

| No | $R^1$ | $R^2$ | $R^3$ | X | B | D | $Y^1$ | $Y^2$ | $Y^4$ | $Y^5$ | $R^{12a}$ | $R^{12b}$ | $R^{13}$ | $R^{12c}$ | $R^{12d}$ | HPLC | RT | m/z | MW |
|---|---|---|---|---|---|---|---|---|---|---|---|---|---|---|---|---|---|---|---|
| A-1 | $CF_3$ | H | H | CO | N | N | N | C | C | C | — | $CH_3$ | H | H | H | 1 | 3.70 | 300.2 | 299.3 |
| A-2 | $CF_3$ | H | H | CO | N | N | N | C | C | C | — | H | H | $CH_3$ | H | 1 | 3.91 | 300.2 | 299.3 |
| A-3 | $CF_3$ | H | H | CO | N | N | N | C | C | C | — | H | H | H | $CH_3$ | 1 | 3.70 | 300.2 | 299.3 |
| A-4 | $CF_3$ | H | H | CO | N | N | N | C | C | C | — | $OCH_3$ | H | H | H | 1 | 4.01 | 316.2 | 315.3 |
| A-5 | $CF_3$ | H | H | CO | N | N | N | C | C | C | — | H | H | $OCH_3$ | H | 1 | 3.52 | 316.2 | 315.3 |
| A-6 | $CF_3$ | H | H | CO | N | N | N | C | C | C | — | H | $Y^2$—CH=CH—CH=CH—$Y^3$ | H | H | 1 | 3.50 | 286.2 | 285.3 |
| A-7 | $CF_3$ | H | H | CO | N | N | N | C | C | C | — | H | H | $Y^4$—CH=CH—CH=CH—$Y^5$ | H | 1 | 4.04 | 336.3 | 335.3 |
| A-8 | $CF_3$ | H | H | CO | N | N | N | C | C | C | — | H | $Y^3$—CH=CH—CH=CH—$Y^4$ | H | H | 1 | 4.14 | 336.3 | 335.3 |
| A-9 | $CF_3$ | H | H | CO | N | N | N | C | C | C | — | H | $CH_3$ | H | H | 1 | 4.10 | 336.3 | 335.3 |
| A-10 | $CF_3$ | H | H | CO | N | N | N | C | C | C | — | $CH_3$ | H | $CH_3$ | H | 1 | 3.51 | 301.2 | 300.3 |
| A-11 | $CF_3$ | H | H | CO | N | N | N | C | C | C | — | H | $OCH_3$ | $CH_3$ | H | 1 | 3.41 | 301.2 | 300.3 |
| A-12 | $CF_3$ | H | H | CO | N | N | N | C | C | C | — | $OCH_3$ | H | $CH_3$ | H | 1 | 3.58 | 317.2 | 316.3 |
| A-13 | $CF_3$ | H | H | CO | N | N | N | C | C | C | — | $OCH_3$ | H | $OCH_3$ | H | 1 | 3.60 | 317.2 | 316.3 |
| A-14 | $CF_3$ | H | H | CO | N | N | N | C | C | N | — | $OCH_3$ | H | H | — | 1 | 3.71 | 317.2 | 316.3 |
| A-15 | $CF_3$ | H | H | CO | N | N | N | C | C | N | — | $CH_3$ | H | $CH_3$ | — | 1 | 3.86 | 315.2 | 314.3 |
| A-16 | $CF_3$ | H | H | CO | N | N | N | C | N | N | — | $CH_3$ | H | H | — | 1 | 3.68 | 301.2 | 300.3 |
| A-17 | $CF_3$ | H | H | CO | N | N | N | C | C | C | — | $CH_3$ | $CH_3$ | H | H | 1 | 3.63 | 315.2 | 314.3 |
| A-18 | Cl | Cl | H | CO | N | N | N | C | C | C | — | H | H | H | H | 2 | 0.92 | 266.0 | 265.7 |
| A-19 | H | H | H | CO | N | N | N | C | C | C | — | H | H | H | H | 2 | 0.86 | 266.0 | 265.7 |
| A-20 | $OC_2H_5$ | H | H | CO | N | N | N | C | C | C | — | H | H | H | H | 2 | 0.91 | 276.1 | 275.3 |
| A-21 | $SCH_3$ | H | H | CO | N | N | N | C | C | C | — | H | H | H | H | 2 | 0.91 | 278.0 | 277.4 |
| A-22 | (E)—CHCHCH$_3$ | H | H | CO | N | N | N | C | C | C | — | H | H | H | H | 2 | 0.98 | 272.1 | 271.4 |
| A-23 | $COCH_3$ | H | H | CO | N | N | N | C | C | C | — | H | H | H | H | 2 | 0.82 | 274.1 | 273.3 |
| A-24 | $CO_2C_2H_5$ | H | H | CO | N | N | N | C | C | C | — | H | H | H | H | 2 | 0.94 | 304.0 | 303.4 |
| A-25 | $CH(CH_3)_2$ | H | $CH_3$ | CO | N | N | N | C | C | C | — | H | H | H | H | 2 | 1.07 | 288.0 | 287.4 |
| A-26 | cyclopropyl | H | H | CO | N | N | N | C | C | C | — | H | H | H | H | 2 | 0.74 | 272.1 | 271.4 |
| A-27 | $(CH_2)_2CCH$ | H | H | CO | N | N | N | C | C | C | — | H | H | H | H | 2 | 0.94 | 284.1 | 283.4 |
| A-28 | $(CH_2)_2SCH_3$ | H | H | CO | N | N | N | C | C | C | — | H | H | H | H | 2 | 0.96 | 306.0 | 305.4 |
| A-29 | $CF_3$ | $CH_3$ | H | CO | N | N | N | C | C | C | — | H | H | $CH_3$ | H | 2 | 1.03 | 314.1 | 313.3 |
| A-30 | $SF_5$ | H | H | CO | N | N | N | C | C | C | — | $CH(CH_3)_2$ | H | $CH_3$ | H | 2 | 1.06 | 358.0 | 357.3 |
| A-31 | $CF_2Cl$ | H | H | CO | N | N | N | C | C | C | — | $CH_3$ | H | $CH_3$ | H | 2 | 1.03 | 316.0 | 315.7 |
| A-32 | thiophen-2-yl | H | H | CO | N | N | N | C | C | C | — | — | H | $CH_3$ | H | 2 | 1.01 | 314.0 | 313.4 |
| A-33 | imidazol-4-yl | H | H | CO | N | N | N | C | C | C | — | $CH_3$ | H | $CH_3$ | H | 2 | 0.74 | 298.1 | 297.3 |
| A-34 | furan-2-yl | H | H | CO | N | N | N | C | C | C | — | H | H | $CH_3$ | H | 2 | 0.97 | 298.0 | 297.3 |
| A-35 | H | $CH_3$ | $CH_3$ | CO | N | N | N | C | C | C | — | H | H | $CH_3$ | H | 2 | 0.81 | 232.1 | 231.3 |
| A-36 | $CH_3$ | $CH_3$ | H | CO | N | N | N | C | C | C | — | H | H | $CH_3$ | H | 2 | 0.92 | 260.1 | 259.4 |
| A-37 | phenyl | H | H | CO | N | N | N | C | C | C | — | H | H | $CH_3$ | H | 2 | 1.03 | 308.1 | 307.4 |
| A-38 | $CF_2CF_4$ | H | H | CO | N | N | N | C | C | C | — | H | H | $OCH_3$ | H | 2 | 0.96 | 348.0 | 347.3 |
| A-39 | $CF_2CF_3$ | H | H | CO | N | N | N | C | C | C | — | H | H | $OCH_3$ | H | 2 | 1.04 | 366.0 | 365.3 |
| A-40 | $CHF_2$ | H | H | CO | N | N | N | C | C | C | — | H | H | $OCH_3$ | H | 2 | 0.87 | 298.0 | 297.3 |
| A-41 | $CF_2Cl$ | H | H | CO | N | N | N | C | C | C | — | H | H | $OCH_3$ | H | 2 | 0.99 | 332.0 | 331.7 |
| A-42 | $CF_2CH_3$ | H | H | CO | N | N | N | C | C | C | — | H | H | $OCH_3$ | H | 2 | 0.92 | 312.0 | 311.3 |
| A-43 | $CF_3$ | H | H | CO | N | N | N | C | C | C | — | $CH_3$ | $CH_3$ | H | H | 2 | 4.14 | 314.2 | 313.3 |
| A-44 | $CF_3$ | H | H | CO | N | N | N | C | C | C | — | $CH_3$ | H | H | $OCH_3$ | 1 | 4.56 | 328.3 | 327.3 |
| A-45 | $CF_3$ | H | H | CO | N | N | N | C | C | C | — | — | H | H | $OCH_3$ | 1 | 3.98 | 330.2 | 329.3 |
| A-46 | $CF_3$ | H | H | CO | N | N | C | C | C | C | — | $CH_3$ | $CH_3$ | H | H | 1 | 3.06 | 316.2 | 315.3 |
| A-47 | $CF_2CH_3$ | H | H | CO | N | N | N | C | C | C | H | — | H | H | H | 1 | 0.79 | 310.0 | 309.4 |

TABLE A-continued

| No. | R1 | R2 | R3 | L | X1 | X2 | X3 | X4 | R4 | R5 | R6 | R7 | n | t | m/z | m/z |
|---|---|---|---|---|---|---|---|---|---|---|---|---|---|---|---|---|
| A-48 | CF₂CH₃ | H | H | CO | N | N | C | C | — | CH(CH₃)₂ | H | H | 1 | 4.44 | 324.3 | 323.4 |
| A-49 | CF₂CH₃ | H | H | CO | N | N | C | C | — | CH₃ | H | OCH₃ | 1 | 3.84 | 326.2 | 325.4 |
| A-50 | CF₂CH₃ | H | H | CO | N | N | N | C | H | — | H | OCH₃ | 1 | 2.96 | 312.2 | 311.3 |
| A-51 | CH(CH₃)₂ | H | H | CO | N | N | C | C | CH(CH₃)₂ | — | H | H | 2 | 4.66 | 302.3 | 301.4 |
| A-52 | CH(CH₃)₂ | H | H | CO | N | N | N | C | — | CH₃ | CH₃ | CH₃ | 1 | 4.21 | 288.3 | 287.4 |
| A-53 | CH(CH₃)₂ | H | H | CO | N | N | N | C | — | CH₃ | CH₃ | OCH₃ | 1 | 4.03 | 304.3 | 303.4 |
| A-54 | CH(CH₃)₂ | H | H | CO | N | C | C | C | H | — | CH₃ | OCH₃ | 1 | 3.11 | 290.2 | 289.4 |
| A-55 | CF₃ | OC₂H₅ | H | CO | N | N | C | C | CH₃ | — | CH₃ | CH₃ | 2 | 0.95 | 314.2 | 313.3 |
| A-56 | CF₃ | H | H | CS | N | N | C | C | H | — | CH₃ | H | 2 | 1.08 | 344.1 | 343.3 |
| A-57 | CF₃ | H | H | CO | N | N | C | C | CH₃ | — | CH₃ | H | 2 | 1.14 | 316.1 | 315.4 |
| A-58 | CF₃ | H | H | CO | N | N | C | C | H | — | CH₃ | H | 2 | 0.91 | 299.1 | 298.3 |
| A-59 | CF₃ | H | H | SO₂ | N | N | C | C | — | CH₃ | CH₃ | H | 1 | 3.49 | 322.1 | 321.3 |
| A-60 | CH(CH₃)₂ | H | H | SO₂ | N | N | C | C | — | CH(CH₃)₂ | CH₃ | H | 2 | 3.50 | 296.2 | 295.4 |
| A-61 | CH(CH₃)₂ | H | H | SO₂ | N | C | C | C | — | CH₃ | CH₃ | H | 1 | 4.13 | 310.2 | 309.4 |
| A-62 | CF₂CF₃ | H | H | SO₂ | N | N | C | C | — | CH₃ | CH₃ | H | 1 | 4.35 | 386.2 | 385.4 |
| A-63 | CF₃ | H | H | CO | N | N | C | C | — | CH₃ | CH₃ | H | 1 | 4.09 | 336.2 | 335.3 |
| A-64 | CF₃ | H | H | CO | N | N | C | C | CH₃ | — | CH₃ | H | 2 | 1.14 | 344.1 | 343.3 |
| A-65 | CF₃ | H | H | CO | N | N | C | C | H | — | CH₃ | H | 2 | 0.90 | 330.1 | 329.3 |
| A-66 | CF₃ | H | H | CO | C | C | C | N | — | H | H | H | 2 | 0.92 | 300.1 | 299.3 |
| A-67 | CF₂Cl | H | H | CO | N | N | C | C | — | CH(CH₃)₂ | H | H | 1 | 4.69 | 344.3 | 343.8 |
| A-68 | CH(CH₃)₂ | H | H | CO | N | N | N | C | H | — | CH₃ | H | 2 | 1.19 | 273.2 | 272.4 |
| A-69 | CF₃ | H | H | CO | N | N | C | C | F | — | CH₃ | H | 1 | 4.10 | 318.1 | 317.3 |
| A-70 | CF₃ | H | H | CO | N | N | C | C | OCH₂CH₃ | — | CH₃ | H | 3 | 1.36 | 344.1 | 343.3 |
| A-71 | CF₂CH₃ | H | H | CO | N | N | C | C | OCH₂CH₃ | — | CH₃ | H | 3 | 1.32 | 340.1 | 339.4 |
| A-72 | CF₂Cl | H | H | CO | N | N | C | C | OCH₂CH₃ | — | CH₃ | H | 3 | 1.62 | 360.1 | 359.8 |
| A-73 | CH(CH₃)₂ | H | H | CO | N | N | C | C | — | CH₃ | CH₃ | CONH₂ | 2 | 0.71 | 332.2 | 331.4 |
| A-74 | CH(CH₃)₂ | H | H | CO | N | N | C | C | — | CH₃ | H | H | 2 | 0.78 | 261.2 | 260.3 |
| A-75 | CF₃ | H | H | CO | N | N | C | C | — | CH₃ | CH₃ | CONH₂ | 2 | 0.70 | 358.1 | 357.3 |
| A-76 | CF₃ | H | H | CO | C | C | C | C | — | CH₃ | H | H | 2 | 0.76 | 287.1 | 286.3 |
| A-77 | CF₃ | H | H | CO | N | N | C | C | H | — | CH₃ | H | 2 | 1.09 | 320.0 | 319.7 |
| A-78 | CF₃ | H | H | CO | N | N | C | C | OCH₃ | — | CH₃ | Cl | 2 | 1.13 | 330.1 | 329.3 |
| A-79 | CF₂CH₃ | H | H | CO | N | N | C | C | OCH₃ | — | CH₃ | H | 2 | 1.10 | 326.1 | 325.4 |
| A-80 | CF₂Cl | H | H | CO | N | N | C | C | OCH₃ | — | CH₃ | H | 2 | 1.17 | 346.1 | 345.8 |
| A-81 | CF₃ | H | H | CO | N | N | C | C | SCH₃ | — | SCH₃ | H | 2 | 0.99 | 332.1 | 331.4 |
| A-82 | CF₃ | H | H | CO | N | N | C | C | N(CH₃)₂ | — | CH₃ | H | 2 | 0.95 | 332.1 | 331.4 |
| A-83 | CF₃ | H | H | CO | N | N | C | C | H | — | CH₃ | NO₂ | 2 | 0.95 | 329.1 | 328.3 |
| A-84 | CF₃ | H | H | CO | N | N | C | C | NO₂ | — | CH₃ | H | 2 | 1.36 | 345.0 | 344.3 |
| A-85 | CF₃ | H | H | CO | N | N | C | C | N-pyrrolidinyl | — | CH₃ | H | 2 | 1.34 | 345.1 | 344.3 |
| A-86 | CF₃ | H | H | CO | N | N | C | C | N-piperidinyl | — | CH₃ | H | 2 | 1.23 | 355.1 | 354.4 |
| A-87 | CF₃ | H | H | CO | N | N | C | C | Y²—CH₂—CH₂—CH₂—CH₂—Y³ | — | CH₃ | H | 2 | 1.26 | 369.1 | 368.4 |
| A-88 | CF₃ | H | H | CO | N | N | C | C | C(CH₃)₃ | SCH₃ | CH₃ | H | 2 | 1.06 | 332.0 | 331.4 |
| A-89 | CF₂CH₃ | H | H | CO | N | N | C | C | H | phenyl | CH₃ | H | 2 | 1.19 | 340.1 | 339.4 |
| A-90 | CF₂Cl | H | H | CO | N | N | C | C | N-morpholinyl | — | CH₃ | H | 2 | 1.28 | 342.1 | 341.4 |
| A-91 | CF₃ | H | H | CO | N | N | C | C | H | — | CH₃ | H | 2 | 1.16 | 362.1 | 361.4 |
| A-92 | CF₃ | H | H | CO | N | N | C | C | H | — | CH₃ | H | 2 | 1.05 | 371.2 | 370.4 |
| A-93 | CF₃ | H | H | CO | N | C | C | C | H | N-morpholinyl | H | H | 1 | 3.35 | 371.2 | 370.4 |
| A-94 | CF₃ | H | H | CO | N | N | C | C | H | H | CH(CH₃)₂ | H | 1 | 4.19 | 328.2 | 327.3 |
| A-95 | CF₃ | H | H | CO | N | N | C | C | H | H | cyclopropyl | H | 1 | 3.96 | 326.2 | 325.3 |
| A-96 | CF₃ | H | H | CO | N | N | C | C | H | CON(CH₃)₂ | H | H | 1 | 3.08 | 357.2 | 356.3 |
| A-97 | CF₃ | H | H | CO | N | N | C | C | SCH₃ | H | H | H | 1 | 4.24 | 332.1 | 331.4 |
| A-98 | CF₃ | H | H | CO | N | N | C | C | SO₂CH₃ | H | H | H | 1 | 3.23 | 364.1 | 363.4 |

TABLE A-continued

| | | | | | | | | | | | | |
|---|---|---|---|---|---|---|---|---|---|---|---|---|
| A-99 | CF₃ | H | CO | N | N | C | C | — | CH₃ | H | CN | CH₃ | 1 | 3.73 | 325.2 | 324.3 |
| A-100 | CH(CH₃)₂ | H | CO | N | C | N | C | CH₃ | — | H | H | H | 4 | 1.34 | 273.2 | 272.4 |
| A-101 | CF₃ | H | CO | N | N | N | C | — | CH₃ | H | Y⁴—O—CH=CH—Y⁵ | 2 | 0.99 | 326.1 | 325.3 |
| A-102 | CF₃ | H | CO | N | N | N | C | — | CH₃ | H | H | CONH₂ | 2 | 0.76 | 329.1 | 328.3 |
| A-103 | CF₃ | H | CO | N | N | N | C | — | OCH₂CH₃ | H | H | H | 2 | 1.05 | 330.1 | 329.3 |
| A-104 | CF₃ | H | CO | N | N | N | C | — | CH₃ | OCH₃ | H | H | 2 | 1.13 | 330.1 | 329.3 |
| A-105 | CF₂CH₃ | H | CO | N | N | N | C | — | CH₃ | H | OCH₃ | H | 2 | 1.02 | 326.2 | 325.4 |
| A-106 | CF₂Cl | H | CO | N | N | N | C | — | CH₃ | H | OCH₃ | H | 1 | 1.08 | 346.1 | 345.8 |
| A-107 | CF₃ | H | CO | N | N | N | C | — | CH₃ | OCH₂CH₃ | H | H | 2 | 4.13 | 344.2 | 343.3 |
| A-108 | CF₂CH₃ | H | CO | N | N | N | C | — | CH₃ | OCH₂CH₃ | H | H | 2 | 4.01 | 340.2 | 339.4 |
| A-109 | CF₂Cl | H | CO | N | N | N | C | — | CH₃ | OCH₂CH₃ | H | H | 1 | 4.24 | 360.2 | 359.8 |
| A-110 | CF₃ | H | CO | N | N | N | C | — | H | H | CO₂C₂H₅ | H | 4 | 1.87 | 358.1 | 357.3 |
| A-111 | CF₃ | H | CO | N | N | N | C | — | CH₃ | H | CN | H | 4 | 1.79 | 311.1 | 310.3 |
| A-112 | CF₃ | H | CO | N | N | N | N | — | Y₂—CH=N—N=Y₃ | H | H | 2 | 0.75 | 327.1 | 326.3 |
| A-113 | CF₃ | H | CO | N | C | C | C | — | H | H | CF₃ | H | 4 | 2.02 | 354.0 | 353.3 |
| A-114 | CF₃ | H | CO | N | N | N | C | — | CH₃ | H | H | H | 4 | 1.71 | 385.1 | 384.4 |
| A-115 | CF₃ | H | CO | N | N | N | C | — | CH₃ | H | H | CON(C₂H₅)₂ | 4 | 1.55 | 357.1 | 356.3 |
| A-116 | CF₃ | H | CO | N | N | N | C | — | CH₃ | H | H | CONHC₂H₅ | 4 | 1.45 | 343.1 | 342.3 |
| A-117 | CF₃ | H | CO | N | N | N | C | — | CH₃ | H | H | CONHCH₃ | 2 | 0.93 | 371.1 | 370.4 |
| A-118 | CF₃ | H | CO | N | N | N | C | — | CH₃ | H | CONH₂ | CONH(CH₂)₂CH₃ | 2 | 0.76 | 329.1 | 328.3 |
| A-119 | CF₃ | H | CO | N | C | C | C | — | CF₃ | H | CF₃ | H | 4 | 2.15 | 388.0 | 387.7 |
| A-120 | CF₃ | H | CO | N | N | N | C | — | H | H | H | Cl | 4 | 2.07 | 354.0 | 353.3 |
| A-121 | CF₃ | F | CO | N | N | N | C | CH₃ | — | H | H | H | 2 | 0.95 | 314.2 | 313.3 |
| A-122 | CF₃ | H | CO | N | N | C | C | — | H | H | H | SO₂NH₂ | 2 | 1.06 | 314.2 | 313.3 |
| A-123 | CF₃ | H | CO | N | N | N | C | — | H | H | CO₂CH₃ | CH₃ | 2 | 0.72 | 365.1 | 364.3 |
| A-124 | CF₃ | H | CO | N | N | N | C | — | N(CH₃)₂ | H | CH₂CH₃ | H | 2 | 0.97 | 344.1 | 343.3 |
| A-125 | CF₃ | H | CO | N | N | N | C | — | CH₃ | H | H | CONH₂ | 2 | 1.13 | 329.1 | 328.3 |
| A-126 | CF₃ | H | CO | N | N | N | C | — | CH₃ | H | CH₃ | H | 2 | 0.85 | 357.2 | 356.3 |
| A-127 | CF₃ | H | CO | N | N | N | C | H | — | H | Cl | CH₃ | 3 | 1.43 | 373.0 | 372.8 |
| A-128 | CF₃ | H | CO | N | N | O | C | — | H | H | N-piperidinyl | phenyl | 2 | 1.09 | 369.2 | 368.4 |
| A-129 | CF₃ | H | CO | N | N | N | C | — | CH₃ | H | H | CO₂CH₃ | 2 | 1.14 | 362.1 | 361.4 |
| A-130 | CF₃ | H | CO | N | N | O | C | H | — | H | N-pyrrolidinyl | CH₃ | 3 | 1.09 | 358.1 | 357.3 |
| A-131 | CF₃ | H | CO | N | N | N | C | — | CH₃ | H | H | H | 2 | 1.01 | 355.2 | 354.4 |
| A-132 | H | H | CO | N | N | N | C | — | CH₃ | H | H | CH₃ | 2 | 0.90 | 250.1 | 249.3 |
| A-133 | CF₃ | H | CO | N | N | N | C | — | CH₃ | CH₃ | H | NH₂ | 2 | 0.90 | 315.1 | 214.3 |
| A-134 | CF₃ | H | CO | N | N | N | C | — | CN | CH₃ | CH₃ | CH₃ | 3 | 1.31 | 353.0 | 352.4 |
| A-135 | CF₃ | H | CO | N | N | N | C | — | NHCOC(CH₃)₃ | H | H | H | 3 | 1.39 | 385.0 | 384.4 |
| A-136 | CF₃ | H | CO | N | N | N | C | — | H | H | NHCOCH₃ | COCH₃ | 3 | 0.92 | 343.0 | 342.3 |
| A-137 | CF₃ | H | CO | N | N | N | C | CH₃ | — | H | H | H | 3 | 0.97 | 328.0 | 327.3 |
| A-138 | CF₂Cl | H | CO | N | N | N | C | — | H | H | H | CH₃ | 2 | 0.99 | 330.1 | 329.8 |
| A-139 | CF₃ | H | CO | N | N | N | C | — | H | H | SO₂NH₂ | H | 2 | 0.79 | 365.1 | 364.3 |
| A-140 | CF₃ | H | CO | N | N | N | C | — | H | H | CONHC₂H₅ | H | 2 | 0.84 | 357.2 | 356.3 |
| A-141 | CF₃ | H | CO | N | C | N | C | H | — | H | H | SO₂CH₃ | 2 | 0.82 | 364.1 | 363.4 |

TABLE A-continued ($Y^3$ = C, $R^2$ = H, $R^3$ = H, X = CO, B = N)

| No | $R^1$ | D | $Y^1$ | $Y^2$ | $Y^4$ | $Y^5$ | $R^{12a}$ | $R^{12b}$ | $R^{13}$ | $R^{12c}$ | $R^{12d}$ | synth. methods |
|---|---|---|---|---|---|---|---|---|---|---|---|---|
| A-142 | $CHF_2$ | N | N | C | C | C | — | H | H | H | $CH_3$ | 15A-B, 1A-D, 18D |
| A-143 | $CF_2Cl$ | N | N | C | C | C | — | H | H | H | $CH_3$ | 15A-B, 1A-D, 18D |
| A-144 | $CF_2Br$ | N | N | C | C | C | — | H | H | H | $CH_3$ | 15A-B, 1A-D, 18D |
| A-145 | $CF_2CH_3$ | N | N | C | C | C | — | H | H | H | $CH_3$ | 15A-B, 1A-D, 18D |
| A-146 | $CF_2CHF_2$ | N | N | C | C | C | — | H | H | H | $CH_3$ | 15A-B, 1A-D, 18D |
| A-147 | $CF_2CF_3$ | N | N | C | C | C | — | H | H | H | $CH_3$ | 15A-B, 1A-D, 18D |
| A-148 | $CHF_2$ | N | N | C | C | C | — | H | H | $CH_3$ | H | 15A-B, 1A-D, 18D |
| A-149 | $CF_2Br$ | N | N | C | C | C | — | H | H | $CH_3$ | H | 15A-B, 1A-D, 18D |
| A-150 | $CF_2CH_3$ | N | N | C | C | C | — | H | H | $CH_3$ | H | 15A-B, 1A-D, 18D |
| A-151 | $CF_2CHF_2$ | N | N | C | C | C | — | H | H | $CH_3$ | H | 15A-B, 1A-D, 18D |
| A-152 | $CF_2CF_3$ | N | N | C | C | C | — | H | H | $CH_3$ | H | 15A-B, 1A-D, 18D |
| A-153 | $CHF_2$ | N | N | C | C | C | — | H | H | $CH_3$ | H | 15A-B, 1A-D, 18D |
| A-154 | $CF_2Cl$ | N | N | C | C | C | — | H | H | $CH_3$ | H | 15A-B, 1A-D, 18D |
| A-155 | $CF_2Br$ | N | N | C | C | C | — | H | H | $CH_3$ | H | 15A-B, 1A-D, 18D |
| A-156 | $CF_2CH_3$ | N | N | C | C | C | — | H | H | $C_2H_5$ | H | 15A-B, 1A-D, 18D |
| A-157 | $CF_2CHF_2$ | N | N | C | C | C | — | H | H | $C_2H_5$ | H | 15A-B, 1A-D, 18D |
| A-158 | $CF_2CF_3$ | N | N | C | C | C | — | H | H | $C_2H_5$ | H | 15A-B, 1A-D, 18D |
| A-159 | $CF_3$ | N | N | C | C | C | — | H | H | $C_2H_5$ | H | 15A-B, 18D |
| A-160 | $CHF_2$ | N | N | C | C | C | — | H | H | $C_2H_5$ | H | 15A-B, 1A-D, 18D |
| A-161 | $CF_2Cl$ | N | N | C | C | C | — | H | H | $(CH_2)_2CH_3$ | H | 15A-B, 1A-D, 18D |
| A-162 | $CF_2Br$ | N | N | C | C | C | — | H | H | $(CH_2)_2CH_3$ | H | 15A-B, 1A-D, 18D |
| A-163 | $CF_2CH_3$ | N | N | C | C | C | — | H | H | $(CH_2)_2CH_3$ | H | 15A-B, 1A-D, 18D |
| A-164 | $CF_2CHF_2$ | N | N | C | C | C | — | H | H | $(CH_2)_2CH_3$ | H | 15A-B, 1A-D, 18D |
| A-165 | $CF_2CF_3$ | N | N | C | C | C | — | H | H | $(CH_2)_2CH_3$ | H | 15A-B, 1A-D, 18D |
| A-166 | $CHF_2$ | N | N | C | C | C | — | H | H | $(CH_2)_2CH_3$ | H | 15A-B, 1A-D, 18D |
| A-167 | $CF_2Cl$ | N | N | C | C | C | — | H | H | $CH(CH_3)_2$ | H | 15A-B, 1A-D, 18D |
| A-168 | $CF_2Br$ | N | N | C | C | C | — | H | H | $CH(CH_3)_2$ | H | 15A-B, 1A-D, 18D |
| A-169 | $CF_2CH_3$ | N | N | C | C | C | — | H | H | $CH(CH_3)_2$ | H | 15A-B, 1A-D, 18D |
| A-170 | $CF_2CHF_2$ | N | N | C | C | C | — | H | H | $CH(CH_3)_2$ | H | 15A-B, 1A-D, 18D |
| A-171 | $CF_2CF_3$ | N | N | C | C | C | — | H | H | $CH(CH_3)_2$ | H | 15A-B, 1A-D, 18D |
| A-172 | $CHF_2$ | N | N | C | C | C | — | H | H | cyclopropyl | H | 15A-B, 1A-D, 18D |
| A-173 | $CF_2Cl$ | N | N | C | C | C | — | H | H | cyclopropyl | H | 15A-B, 1A-D, 18D |
| A-174 | $CF_2Br$ | N | N | C | C | C | — | H | H | cyclopropyl | H | 15A-B, 1A-D, 18D |
| A-175 | $CF_2CH_3$ | N | N | C | C | C | — | H | H | cyclopropyl | H | 15A-B, 1A-D, 18D |
| A-176 | $CF_2CHF_2$ | N | N | C | C | C | — | H | H | cyclopropyl | H | 15A-B, 1A-D, 18D |
| A-177 | $CF_2CF_3$ | N | N | C | C | C | — | H | H | cyclopropyl | H | 15A-B, 1A-D, 18D |
| A-178 | $CF_3$ | N | N | C | C | C | — | H | H | $OCH_3$ | H | 18A-C, 1A-D, 18D |
| A-179 | $CHF_2$ | N | N | C | C | C | — | H | H | $OC_2H_5$ | H | 18A-D |
| A-180 | $CF_2Cl$ | N | N | C | C | C | — | H | H | $OC_2H_5$ | H | 18A-C, 1A-D, 18D |
| A-181 | $CF_2Br$ | N | N | C | C | C | — | H | H | $OC_2H_5$ | H | 18A-C, 1A-D, 18D |
| A-182 | $CF_2CH_3$ | N | N | C | C | C | — | H | H | $OC_2H_5$ | H | 18A-C, 1A-D, 18D |
| A-183 | $CF_2CHF_2$ | N | N | C | C | C | — | H | H | $OC_2H_5$ | H | 18A-C, 1A-D, 18D |
| A-184 | $CF_2CF_3$ | N | N | C | C | C | — | H | H | $OC_2H_5$ | H | 18A-C, 1A-D, 18D |
| A-185 | $CF_3$ | N | N | C | C | C | — | $CH_3$ | $CH_3$ | H | H | 18A-C, 1A-D, 18D |
| A-186 | $CF_3$ | N | N | C | C | C | — | H | H | H | H | 15A-B, 18D |

TABLE A-continued

| | | | | | | | | | |
|---|---|---|---|---|---|---|---|---|---|
| A-187 | CHF₂ | N | C | C | — | CH₃ | CH₃ | H | 15A-B, 1A-D, 18D |
| A-188 | CF₂Cl | N | C | C | — | CH₃ | CH₃ | H | 15A-B, 1A-D, 18D |
| A-189 | CF₂Br | N | C | C | — | CH₃ | CH₃ | H | 15A-B, 1A-D, 18D |
| A-190 | CF₂CHF₂ | N | C | C | — | CH₃ | CH₃ | H | 15A-B, 1A-D, 18D |
| A-191 | CF₂CF₃ | N | C | C | — | CH₃ | CH₃ | H | 15A-B, 1A-D, 18D |
| A-192 | CHF₂ | N | C | C | — | CH₃ | H | OCH₃ | 20A-F, 1A-D, 18D |
| A-193 | CF₂Cl | N | C | C | — | CH₃ | H | OCH₃ | 20A-F, 1A-D, 18D |
| A-194 | CF₂Br | N | C | C | — | CH₃ | H | OCH₃ | 20A-F, 1A-D, 18D |
| A-195 | CF₂CHF₂ | N | C | C | — | CH₃ | H | OCH₃ | 20A-F, 1A-D, 18D |
| A-196 | CF₂CF₃ | N | C | C | — | CH₃ | H | OC₂H₅ | 20A-F, 1A-D, 18D |
| A-197 | CHF₂ | N | C | C | — | CH₃ | H | OC₂H₅ | 20A-F, 1A-D, 18D |
| A-198 | CF₂Br | N | C | C | — | CH₃ | H | OC₂H₅ | 20A-F, 1A-D, 18D |
| A-199 | CF₂CHF₂ | N | C | C | — | CH₃ | H | OC₂H₅ | 20A-F, 1A-D, 18D |
| A-200 | CF₃ | N | C | C | — | C₂H₅ | H | OCH₃ | 18A-D |
| A-201 | CHF₂ | N | C | C | — | C₂H₅ | H | OCH₃ | 18A-C, 1A-D, 18D |
| A-202 | CF₂Cl | N | C | C | — | C₂H₅ | H | OCH₃ | 18A-C, 1A-D, 18D |
| A-203 | CF₂Br | N | C | C | — | C₂H₅ | H | OCH₃ | 18A-C, 1A-D, 18D |
| A-204 | CF₂CH₃ | N | C | C | — | C₂H₅ | H | OCH₃ | 18A-C, 1A-D, 18D |
| A-205 | CF₂CHF₂ | N | C | C | — | C₂H₅ | H | OCH₃ | 18A-C, 1A-D, 18D |
| A-206 | CF₂CF₃ | N | C | C | — | C₂H₅ | H | OCH₃ | 18A-C, 1A-D, 18D |
| A-207 | CF₃ | N | C | C | — | C₂H₅ | H | H | 15A-B, 18D |
| A-209 | CHF₂ | N | C | C | — | CH₃ | H | H | 15A-B, 1A-D, 18D |
| A-209 | CF₂Cl | N | C | C | — | CH₃ | H | H | 15A-B, 1A-D, 18D |
| A-210 | CF₂Br | N | C | C | — | CH₃ | H | H | 15A-B, 1A-D, 18D |
| A-211 | CF₂CH₃ | N | C | C | — | CH₃ | H | H | 15A-B, 1A-D, 18D |
| A-212 | CF₂CHF₂ | N | C | C | — | CH₃ | H | H | 15A-B, 1A-D, 18D |
| A-213 | CF₂CF₃ | N | C | C | — | CH₃ | H | H | 15A-B, 1A-D, 18D |
| A-214 | CF₃ | N | C | C | — | CH₃ | H | H | 15A-B, 18D |
| A-215 | CHF₂ | N | C | C | — | CH₃ | H | H | CH₃ | 15A-B, 1A-D, 18D |
| A-216 | CF₂Cl | N | C | C | — | CH₃ | H | H | CH₃ | 15A-B, 1A-D, 18D |
| A-217 | CF₂Br | N | C | C | — | CH₃ | H | H | CH₃ | 15A-B, 1A-D, 18D |
| A-218 | CF₂CH₃ | N | C | C | — | CH₃ | H | H | CH₃ | 15A-B, 1A-D, 18D |
| A-219 | CF₂CHF₂ | N | C | C | — | CH₃ | H | H | CH₃ | 15A-B, 1A-D, 18D |
| A-220 | CF₃ | N | C | C | — | CH₃ | H | H | CH₃ | 15A-B, 18D |
| A-221 | CHF₂ | N | C | C | — | CH₃ | H | CH₃ | H | 15A-B, 1A-D, 18D |
| A-222 | CF₂Cl | N | C | C | — | CH₃ | H | CH₃ | H | 15A-B, 1A-D, 18D |
| A-223 | CF₂Br | N | C | C | — | CH₃ | H | CH₃ | H | 15A-B, 1A-D, 18D |
| A-224 | CF₂CH₃ | N | C | C | — | CH₃ | H | CH₃ | H | 15A-B, 1A-D, 18D |
| A-225 | CF₂CHF₂ | N | C | C | — | CH₃ | H | CH₃ | H | 15A-B, 1A-D, 18D |
| A-226 | CF₂CF₃ | N | C | C | — | CH₃ | H | CH₃ | H | 15A-B, 1A-D, 18D |
| A-227 | CF₃ | N | C | C | — | CH₃ | H | CH₃ | H | 15A-B, 18D |
| A-228 | CHF₂ | N | C | C | — | H | H | O(CH₂)₂CH₃ | H | 18A-D |
| A-229 | CF₂Cl | N | C | C | — | H | H | O(CH₂)₂CH₃ | H | 18A-C, 1A-D, 18D |
| A-230 | CF₂Br | N | C | C | — | H | H | O(CH₂)₂CH₃ | H | 18A-C, 1A-D, 18D |
| A-231 | CF₂CH₃ | N | C | C | — | H | H | O(CH₂)₂CH₃ | H | 18A-C, 1A-D, 18D |
| A-232 | CF₂CHF₂ | N | C | C | — | H | H | O(CH₂)₂CH₃ | H | 18A-C, 1A-D, 18D |
| A-233 | CF₂CF₃ | N | C | C | — | H | H | O(CH₂)₂CH₃ | H | 18A-C, 1A-D, 18D |
| A-234 | CF₂CF₃ | N | C | C | — | H | H | O(CH₂)₂CH₃ | H | 18A-C, 1A-D, 18D |
| A-235 | CF₃ | N | C | C | — | H | H | OCH(CH₃)₂ | H | 18A-D |

TABLE A-continued

| ID | | | | | | | | | | |
|---|---|---|---|---|---|---|---|---|---|---|
| A-236 | CHF₂ | N | N | C | — | H | H | OCH(CH₃)₂ | H | 18A-C, 1A-D, 18D |
| A-237 | CF₂Cl | N | N | C | — | H | H | OCH(CH₃)₂ | H | 18A-C, 1A-D, 18D |
| A-238 | CF₂Br | N | N | C | — | H | H | OCH(CH₃)₂ | H | 18A-C, 1A-D, 18D |
| A-239 | CF₂CH₃ | N | N | C | — | H | H | OCH(CH₃)₂ | H | 18A-C, 1A-D, 18D |
| A-240 | CF₂CHF₂ | N | N | C | — | H | H | OCH(CH₃)₂ | H | 18A-C, 1A-D, 18D |
| A-241 | CF₂CF₃ | N | N | C | — | H | H | OCH(CH₃)₂ | H | 18A-C, 1A-D, 18D |
| A-242 | CF₃ | N | N | C | — | H | H | SCH₃ | H | 18A-D |
| A-243 | CHF₂ | N | N | C | — | H | H | SCH₃ | H | 18A-C, 1A-D, 18D |
| A-244 | CF₂Cl | N | N | C | — | H | H | SCH₃ | H | 18A-C, 1A-D, 18D |
| A-245 | CF₂Br | N | N | C | — | H | H | SCH₃ | H | 18A-C, 1A-D, 18D |
| A-246 | CF₂CH₃ | N | N | C | — | H | H | SCH₃ | H | 18A-C, 1A-D, 18D |
| A-247 | CF₂CHF₂ | N | N | C | — | H | H | SCH₃ | H | 18A-C, 1A-D, 18D |
| A-248 | CF₂CF₃ | N | N | C | — | H | H | SCH₃ | H | 18A-C, 1A-D, 18D |
| A-249 | CF₃ | N | N | C | — | H | H | SC₂H₅ | H | 18A-D |
| A-250 | CHF₂ | N | N | C | — | H | H | SC₂H₅ | H | 18A-C, 1A-D, 18D |
| A-251 | CF₂Cl | N | N | C | — | H | H | SC₂H₅ | H | 18A-C, 1A-D, 18D |
| A-252 | CF₂Br | N | N | C | — | H | H | SC₂H₅ | H | 18A-C, 1A-D, 18D |
| A-253 | CF₂CH₃ | N | N | C | — | H | H | SC₂H₅ | H | 18A-C, 1A-D, 18D |
| A-254 | CF₂CHF₂ | N | N | C | — | H | H | SC₂H₅ | H | 18A-C, 1A-D, 18D |
| A-255 | CF₂CF₃ | N | N | C | — | H | H | SC₂H₅ | H | 18A-C, 1A-D, 18D |
| A-256 | CF₃ | N | N | C | — | CH₃ | H | SCH₃ | H | 20A-F, 18D |
| A-257 | CHF₂ | N | N | C | — | CH₃ | H | SCH₃ | H | 20A-F, 1A-D, 18D |
| A-258 | CF₂Cl | N | N | C | — | CH₃ | H | SCH₃ | H | 20A-F, 1A-D, 18D |
| A-259 | CF₂Br | N | N | C | — | CH₃ | H | SCH₃ | H | 20A-F, 1A-D, 18D |
| A-260 | CF₂CH₃ | N | N | C | — | CH₃ | H | SCH₃ | H | 20A-F, 1A-D, 18D |
| A-261 | CF₂CHF₂ | N | N | C | — | CH₃ | H | SCH₃ | H | 20A-F, 1A-D, 18D |
| A-262 | CF₂CF₃ | N | N | C | — | CH₃ | H | SCH₃ | H | 20A-F, 1A-D, 18D |
| A-263 | CF₃ | N | N | C | — | CH₃ | H | SC₂H₅ | H | 20A-F, 18D |
| A-264 | CHF₂ | N | N | C | — | CH₃ | H | SC₂H₅ | H | 20A-F, 1A-D, 18D |
| A-265 | CF₂Cl | N | N | C | — | CH₃ | H | SC₂H₅ | H | 20A-F, 1A-D, 18D |
| A-266 | CF₂Br | N | N | C | — | CH₃ | H | SC₂H₅ | H | 20A-F, 1A-D, 18D |
| A-267 | CF₂CH₃ | N | N | C | — | CH₃ | H | SC₂H₅ | H | 20A-F, 1A-D, 18D |
| A-268 | CF₂CHF₂ | N | N | C | — | CH₃ | H | SC₂H₅ | H | 20A-F, 1A-D, 18D |
| A-269 | CF₂CF₃ | N | N | C | — | CH₃ | H | SC₂H₅ | H | 20A-F, 1A-D, 18D |
| A-270 | CF₃ | N | C | C | CH₃ | — | H | H | H | 15A-B, 18D |
| A-271 | CHF₂ | N | C | C | CH₃ | — | H | H | H | 15A-B, 1A-D, 18D |
| A-272 | CF₂Cl | N | C | C | CH₃ | — | H | H | H | 15A-B, 1A-D, 18D |
| A-273 | CF₂Br | N | C | C | CH₃ | — | H | H | H | 15A-B, 1A-D, 18D |
| A-274 | CF₂CH₃ | N | C | C | CH₃ | — | H | H | H | 15A-B, 1A-D, 18D |
| A-275 | CF₂CHF₂ | N | C | C | CH₃ | — | H | H | H | 15A-B, 1A-D, 18D |
| A-276 | CF₂CF₃ | N | C | C | CH₃ | — | H | H | H | 15A-B, 1A-D, 18D |
| A-277 | CF₃ | N | C | C | CH₃ | — | H | H | CH₃ | 15A-B, 18D |
| A-278 | CHF₂ | N | C | C | CH₃ | — | H | H | CH₃ | 15A-B, 1A-D, 18D |
| A-279 | CF₂Cl | N | C | C | CH₃ | — | H | H | CH₃ | 15A-B, 1A-D, 18D |
| A-280 | CF₂Br | N | C | C | CH₃ | — | H | H | CH₃ | 15A-B, 1A-D, 18D |
| A-281 | CF₂CH₃ | N | C | C | CH₃ | — | H | H | CH₃ | 15A-B, 1A-D, 18D |
| A-282 | CF₂CHF₂ | N | C | C | CH₃ | — | H | H | CH₃ | 15A-B, 1A-D, 18D |
| A-283 | CF₂CF₃ | N | C | C | CH₃ | — | H | H | CH₃ | 15A-B, 1A-D, 18D |

TABLE A-continued

| No. | | | | | | | | | | | |
|---|---|---|---|---|---|---|---|---|---|---|---|
| A-284 | CHF₂ | N | C | C | N | — | CH₃ | H | CH₃ | H | 15A-B, 1A-D, 18D |
| A-285 | CF₂Cl | N | C | C | N | — | CH₃ | H | CH₃ | H | 15A-B, 1A-D, 18D |
| A-286 | CF₂Br | N | C | C | N | — | CH₃ | H | CH₃ | H | 15A-B, 1A-D, 18D |
| A-287 | CF₂CH₃ | N | C | C | N | — | CH₃ | H | CH₃ | H | 15A-B, 1A-D, 18D |
| A-288 | CF₂CHF₂ | N | C | C | N | — | CH₃ | H | CH₃ | H | 15A-B, 1A-D, 18D |
| A-289 | CF₂CF₃ | N | C | C | N | — | CH₃ | H | CH₃ | H | 15A-B, 1A-D, 18D |
| A-290 | CF₃ | N | C | C | N | — | H | H | CH₃ | H | 15A-B, 18D |
| A-291 | CHF₂ | N | C | C | N | — | H | H | CH₃ | H | 15A-B, 1A-D, 18D |
| A-292 | CF₂Cl | N | C | C | N | — | H | H | CH₃ | H | 15A-B, 1A-D, 18D |
| A-293 | CF₂Br | N | C | C | N | — | H | H | CH₃ | H | 15A-B, 1A-D, 18D |
| A-294 | CF₂CH₃ | N | C | C | N | — | H | H | CH₃ | H | 15A-B, 1A-D, 18D |
| A-295 | CF₂CHF₂ | N | C | C | N | — | H | H | CH₃ | H | 15A-B, 1A-D, 18D |
| A-296 | CF₂CF₃ | N | C | C | N | — | H | H | CH₃ | H | 15A-B, 1A-D, 18D |
| A-297 | CF₃ | N | C | C | N | — | CH₃ | H | H | H | 15A-B, 18D |
| A-298 | CHF₂ | N | C | C | N | — | CH₃ | H | H | H | 15A-B, 1A-D, 18D |
| A-299 | CF₂Cl | N | C | C | N | — | CH₃ | H | H | H | 15A-B, 1A-D, 18D |
| A-300 | CF₂Br | N | C | C | N | — | CH₃ | H | H | H | 15A-B, 1A-D, 18D |
| A-301 | CF₂CH₃ | N | C | C | N | — | CH₃ | H | H | H | 15A-B, 1A-D, 18D |
| A-302 | CF₂CHF₂ | N | C | C | N | — | CH₃ | H | H | H | 15A-B, 1A-D, 18D |
| A-303 | CF₂CF₃ | N | C | C | N | — | CH₃ | H | H | H | 15A-B, 1A-D, 18D |
| A-304 | CHF₂ | N | C | C | N | — | H | H | H | OCH₃ | 18C, 15A-B, 1A-D, 18D |
| A-305 | CF₂Cl | N | C | C | N | — | H | H | H | OCH₃ | 18C, 15A-B, 1A-D, 18D |
| A-306 | CF₂Br | N | C | C | N | — | H | H | H | OCH₃ | 18C, 15A-B, 1A-D, 18D |
| A-307 | CF₂CH₃ | N | C | C | N | — | H | H | H | OCH₃ | 18C, 15A-B, 1A-D, 18D |
| A-308 | CF₂CHF₂ | N | C | C | N | — | H | H | H | OCH₃ | 18C, 15A-B, 1A-D, 18D |
| A-309 | CF₂CF₃ | N | C | C | N | — | H | H | H | OCH₃ | 18C, 15A-B, 1A-D, 18D |
| A-310 | CHF₂ | N | C | C | N | — | H | H | H | OC₂H₅ | 18C, 15A-B, 1A-D, 18D |
| A-311 | CF₂Cl | N | C | C | N | — | H | H | H | OC₂H₅ | 18C, 15A-B, 1A-D, 18D |
| A-312 | CF₂Br | N | C | C | N | — | H | H | H | OC₂H₅ | 18C, 15A-B, 1A-D, 18D |
| A-313 | CF₂CH₃ | N | C | C | N | — | H | H | H | OC₂H₅ | 18C, 15A-B, 1A-D, 18D |
| A-314 | CF₂CHF₂ | N | C | C | N | — | H | H | H | OC₂H₅ | 18C, 15A-B, 1A-D, 18D |
| A-315 | CF₂CF₃ | N | C | C | N | — | H | H | H | OC₂H₅ | 18C, 15A-B, 1A-D, 18D |
| A-316 | CF₃ | N | C | C | N | — | H | H | H | SCH₃ | 18C, 15A-B, 18D |
| A-317 | CHF₂ | N | C | C | N | — | H | H | H | SCH₃ | 18C, 15A-B, 1A-D, 18D |
| A-318 | CF₂Cl | N | C | C | N | — | H | H | H | SCH₃ | 18C, 15A-B, 1A-D, 18D |
| A-319 | CF₂Br | N | C | C | N | — | H | H | H | SCH₃ | 18C, 15A-B, 1A-D, 18D |
| A-320 | CF₂CH₃ | N | C | C | N | — | H | H | H | SCH₃ | 18C, 15A-B, 1A-D, 18D |
| A-321 | CF₂CHF₂ | N | C | C | N | — | H | H | H | SCH₃ | 18C, 15A-B, 1A-D, 18D |
| A-322 | CF₂CF₃ | N | C | C | N | — | H | H | H | SCH₃ | 18C, 15A-B, 1A-D, 18D |
| A-323 | CF₃ | N | C | C | N | — | H | H | H | SC₂H₅ | 18C, 15A-B, 18D |
| A-324 | CHF₂ | N | C | C | N | — | H | H | H | SC₂H₅ | 18C, 15A-B, 1A-D, 18D |
| A-325 | CF₂Cl | N | C | C | N | — | H | H | H | SC₂H₅ | 18C, 15A-B, 1A-D, 18D |
| A-326 | CF₂Br | N | C | C | N | — | H | H | H | SC₂H₅ | 18C, 15A-B, 1A-D, 18D |
| A-327 | CF₂CH₃ | N | C | C | N | — | H | H | H | SC₂H₅ | 18C, 15A-B, 1A-D, 18D |
| A-328 | CF₂CHF₂ | N | C | C | N | — | H | H | H | SC₂H₅ | 18C, 15A-B, 1A-D, 18D |
| A-329 | CF₂CF₃ | N | C | C | N | — | H | H | OCH₃ | H | 15A-B, 18D |

TABLE A-continued

| | | | | | | | | | |
|---|---|---|---|---|---|---|---|---|---|
| A-330 | CHF₂ | N | C | C | — | H | OCH₃ | H | 15A-B, 1A-D, 18D |
| A-331 | CF₂Cl | N | C | C | — | H | OCH₃ | H | 15A-B, 1A-D, 18D |
| A-332 | CF₂Br | N | C | C | — | H | OCH₃ | H | 15A-B, 1A-D, 18D |
| A-333 | CF₂CH₃ | N | C | C | — | H | OCH₃ | H | 15A-B, 1A-D, 18D |
| A-334 | CF₂CHF₂ | N | C | C | — | H | OCH₃ | H | 15A-B, 1A-D, 18D |
| A-335 | CF₂CF₃ | N | C | C | — | H | OCH₃ | H | 15A-B, 1A-D, 18D |
| A-336 | CF₃ | N | C | C | — | H | OCH₃ | H | 15A-B, 18D |
| A-337 | CHF₂ | N | C | C | — | H | OC₂H₅ | H | 15A-B, 1A-D, 18D |
| A-338 | CF₂Cl | N | C | C | — | H | OC₂H₅ | H | 15A-B, 1A-D, 18D |
| A-339 | CF₂Br | N | C | C | — | H | OC₂H₅ | H | 15A-B, 1A-D, 18D |
| A-340 | CF₂CH₃ | N | C | C | — | H | OC₂H₅ | H | 15A-B, 1A-D, 18D |
| A-341 | CF₂CHF₂ | N | C | C | — | H | OC₂H₅ | H | 15A-B, 1A-D, 18D |
| A-342 | CF₂CF₃ | N | C | C | — | H | OC₂H₅ | H | 15A-B, 1A-D, 18D |
| A-343 | CF₃ | N | C | C | — | H | O(CH₂)₂CH₃ | H | 15A-B, 18D |
| A-344 | CHF₂ | N | C | C | — | H | O(CH₂)₂CH₃ | H | 15A-B, 1A-D, 18D |
| A-345 | CF₂Cl | N | C | C | — | H | O(CH₂)₂CH₃ | H | 15A-B, 1A-D, 18D |
| A-346 | CF₂Br | N | C | C | — | H | O(CH₂)₂CH₃ | H | 15A-B, 1A-D, 18D |
| A-347 | CF₂CH₃ | N | C | C | — | H | O(CH₂)₂CH₃ | H | 15A-B, 1A-D, 18D |
| A-348 | CF₂CHF₂ | N | C | C | — | H | O(CH₂)₂CH₃ | H | 15A-B, 1A-D, 18D |
| A-349 | CF₂CF₃ | N | C | C | — | H | O(CH₂)₂CH₃ | H | 15A-B, 1A-D, 18D |
| A-350 | CF₃ | N | C | C | — | H | OCH(CH₃)₂ | H | 15A-B, 18D |
| A-351 | CHF₂ | N | C | C | — | H | OCH(CH₃)₂ | H | 15A-B, 1A-D, 18D |
| A-352 | CF₂Cl | N | C | C | — | H | OCH(CH₃)₂ | H | 15A-B, 1A-D, 18D |
| A-353 | CF₂Br | N | C | C | — | H | OCH(CH₃)₂ | H | 15A-B, 1A-D, 18D |
| A-354 | CF₂CH₃ | N | C | C | — | H | OCH(CH₃)₂ | H | 15A-B, 1A-D, 18D |
| A-355 | CF₂CHF₂ | N | C | C | — | H | OCH(CH₃)₂ | H | 15A-B, 1A-D, 18D |
| A-356 | CF₂CF₃ | N | C | C | — | H | OCH(CH₃)₂ | H | 15A-B, 1A-D, 18D |
| A-357 | CHF₂ | N | C | C | — | H | SCH₃ | H | 15A-B, 1A-D, 18D |
| A-358 | CF₂Cl | N | C | C | — | H | SCH₃ | H | 15A-B, 1A-D, 18D |
| A-359 | CF₂Br | N | C | C | — | H | SCH₃ | H | 15A-B, 1A-D, 18D |
| A-360 | CF₂CH₃ | N | C | C | — | H | SCH₃ | H | 15A-B, 1A-D, 18D |
| A-361 | CF₂CHF₂ | N | C | C | — | H | SCH₃ | H | 15A-B, 1A-D, 18D |
| A-362 | CF₂CF₃ | N | C | C | — | H | SCH₃ | H | 15A-B, 1A-D, 18D |
| A-363 | CF₃ | N | C | C | — | H | SC₂H₅ | H | 15A-B, 18D |
| A-364 | CHF₂ | N | C | C | — | H | SC₂H₅ | H | 15A-B, 1A-D, 18D |
| A-365 | CF₂Cl | N | C | C | — | H | SC₂H₅ | H | 15A-B, 1A-D, 18D |
| A-366 | CF₂Br | N | C | C | — | H | SC₂H₅ | H | 15A-B, 1A-D, 18D |
| A-367 | CF₂CH₃ | N | C | C | — | H | SC₂H₅ | H | 15A-B, 1A-D, 18D |
| A-368 | CF₂CHF₂ | N | C | C | — | H | SC₂H₅ | H | 15A-B, 1A-D, 18D |
| A-369 | CF₂CF₃ | N | C | C | — | H | SC₂H₅ | H | 15A-B, 1A-D, 18D |
| A-370 | CH₂OCH₃ | N | N | C | C | H | H | CH₃ | H | 18D |

Further examples of specific compounds of the present invention include each of the compounds of table A above wherein X=SO$_2$ instead of CO and each of the compounds of table A wherein X=CS instead of CO if not already contained in Table A.

Table B below provides for each of the synthesized compounds of the formula (B) the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis. From compound B-40 until to the end of the table the methods by which the compounds are synthesized are identified by referring to the synthesis steps described in the synthesis examples of paragraph B above ("Synthesis Examples").

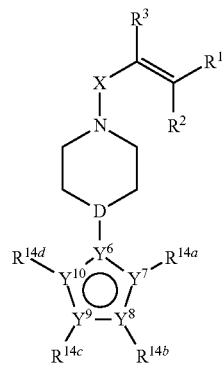

Formula (B)

TABLE B (X = CO, R$^2$ = H, R$^3$ = H)

| No | R$^1$ | D | Y$^6$ | Y$^7$ | Y$^8$ | Y$^9$ | Y$^{10}$ | R$^{14a}$ | R$^{14b}$ | R$^{14c}$ | R$^{14d}$ | HPLC | Rt | m/z | MW |
|---|---|---|---|---|---|---|---|---|---|---|---|---|---|---|---|
| B-1 | CH(CH$_3$)$_2$ | C | C | N | N | N | C | — | — | Y$^9$=CH—CH=CH—CH=Y$^{10}$ | | 5 | 4.09 | 299.1 | 298.4 |
| B-2 | CH$_2$CH$_3$ | C | C | N | N | N | C | — | — | Y$^9$=CH—CH=CH—CH=Y$^{10}$ | | 5 | 3.82 | 285.0 | 284.4 |
| B-3 | (CH$_2$)$_3$CH$_3$ | C | C | N | N | N | C | — | — | Y$^9$=CH—CH=CH—CH=Y$^{10}$ | | 5 | 4.12 | 299.1 | 298.4 |
| B-4 | CF$_3$ | N | C | N | N | C | O | — | — | CH$_3$ | — | 1 | 2.76 | 291.1 | 290.2 |
| B-5 | CF$_3$ | C | C | S | C | C | N | — | H | H | — | 1 | 3.37 | 291.1 | 290.3 |
| B-6 | CF$_3$ | N | C | N | O | C | N | — | — | H | — | 1 | 3.09 | 277.1 | 276.2 |
| B-7 | CF$_3$ | N | C | N | O | C | N | — | — | CH$_3$ | — | 1 | 3.20 | 291.1 | 290.2 |
| B-8 | CF$_2$CH$_3$ | N | C | N | O | C | N | — | — | H | — | 1 | 2.98 | 273.1 | 272.3 |
| B-9 | CF$_3$ | N | C | C | S | C | C | H | — | H | H | 1 | 3.80 | 291.1 | 290.3 |
| B-10 | CF$_3$ | N | C | C | S | C | C | H | — | CH$_3$ | H | 1 | 4.06 | 305.2 | 304.3 |
| B-11 | CF$_3$ | N | C | S | C | N | C | — | H | — | CH$_3$ | 1 | 3.40 | 306.2 | 305.3 |
| B-12 | CF$_2$CH$_3$ | N | C | N | O | C | N | — | — | CH$_3$ | — | 1 | 3.09 | 287.1 | 286.3 |
| B-13 | CF$_2$CH$_3$ | N | C | C | S | C | C | H | — | H | H | 1 | 3.68 | 287.2 | 286.3 |
| B-14 | CF$_2$CH$_3$ | N | C | S | C | N | C | — | H | — | CH$_3$ | 1 | 3.42 | 302.2 | 301.4 |
| B-15 | CF$_3$ | N | C | N | C | C | N | CH$_3$ | H | CH$_3$ | — | 2 | 0.84 | 303.2 | 302.3 |
| B-16 | CF$_3$ | N | C | N | C | C | N | C$_2$H5 | H | H | — | 2 | 0.86 | 303.1 | 302.3 |
| B-17 | CF$_3$ | N | C | N | C | C | N | CH$_3$ | CH$_3$ | H | — | 2 | 0.84 | 303.1 | 302.3 |
| B-18 | CF$_3$ | N | C | N | C | C | N | CH$_3$ | H | H | — | 2 | 0.79 | 289.1 | 288.3 |
| B-19 | CF$_3$ | N | C | S | C | N | N | — | CF$_3$ | — | — | 1 | 3.80 | 361.1 | 360.3 |
| B-20 | CF$_3$ | N | C | S | C | C | N | — | Cl | CO$_2$C$_2$H5 | — | 2 | 1.08 | 398.0 | 397.8 |
| B-21 | CF$_3$ | N | C | S | C | C | N | — | CN | H | — | 3 | 1.01 | 317.1 | 316.3 |
| B-22 | CF$_3$ | N | C | N | N | C | N | — | CH$_3$ | N-morpholinyl | — | 1 | 3.04 | 375.2 | 374.4 |
| B-23 | CF$_3$ | N | C | N | N | C | N | — | CH$_3$ | N(CH$_3$)$_2$ | — | 1 | 3.10 | 333.2 | 332.3 |
| B-24 | CF$_3$ | N | C | S | N | C | N | — | — | N-morpholinyl | — | 1 | 3.47 | 378.2 | 377.4 |
| B-25 | CF$_3$ | N | C | S | C | C | N | — | C$_2$H5 | CO$_2$CH$_3$ | — | 1 | 3.89 | 378.2 | 377.4 |
| B-26 | CF$_3$ | C | N | C | N | C | C | H | — | H | H | 2 | 0.77 | 274.1 | 273.3 |
| B-27 | CF$_3$ | C | C | N | C | N | C | — | H | — | H | 2 | 0.74 | 274.1 | 273.3 |
| B-28 | CF$_3$ | N | C | S | C | C | C | — | SO$_2$NH$_2$ | H | NO$_2$ | 4 | 1.73 | 415.0 | 414.4 |
| B-29 | CF$_3$ | N | C | S | N | C | N | — | — | CH$_3$ | — | 4 | 1.62 | 307.0 | 306.3 |
| B-30 | CF$_3$ | C | C | N | N | C | O | — | — | phenyl | — | 4 | 1.85 | 352.1 | 351.3 |
| B-31 | CF$_3$ | C | C | O | N | C | N | — | — | CH(CH$_3$)$_2$ | — | 4 | 1.87 | 318.1 | 317.3 |
| B-32 | CF$_3$ | N | C | S | C | C | N | — | NHCH$_3$ | CO$_2$C$_2$H$_5$ | — | 2 | 0.66 | 393.1 | 392.4 |
| B-33 | CF$_3$ | N | C | S | C | C | N | — | H | phenyl | — | 2 | 1.17 | 368.1 | 367.4 |
| B-34 | CF$_3$ | N | C | S | C | C | N | — | SO$_2$NH$_2$ | H | — | 3 | 0.77 | 371.0 | 370.4 |
| B-35 | CF$_3$ | N | C | S | C | C | N | — | H | CONH$_2$ | — | 2 | 0.79 | 335.1 | 334.3 |
| B-36 | CF$_3$ | N | C | N | N | C | N | CH$_3$ | — | CH$_3$ | — | 2 | 0.75 | 304.2 | 303.3 |
| B-37 | CF$_3$ | N | C | N | N | C | N | — | CH$_3$ | N-piperidinyl | — | 2 | 1.00 | 373.0 | 372.4 |
| B-38 | CF$_3$ | N | C | N | N | C | N | — | H | SC$_2$H$_5$ | — | 2 | 0.78 | 336.1 | 335.4 |
| B-39 | CF$_3$ | N | C | S | C | C | C | — | SO$_2$C$_2$H5 | H | H | 1 | 3.57 | 383.1 | 382.4 |

| No | R$^1$ | D | Y$^6$ | Y$^7$ | Y$^8$ | Y$^9$ | Y$^{10}$ | R$^{14a}$ | R$^{14b}$ | R$^{14c}$ | R$^{14d}$ | synth. methods |
|---|---|---|---|---|---|---|---|---|---|---|---|---|
| B-40 | CF$_3$ | C | N | C | N | C | C | CH$_3$ | — | H | H | 18D |
| B-41 | CHF$_2$ | C | N | C | N | C | C | CH$_3$ | — | H | H | 1A-D, 18D |
| B-42 | CF$_2$Cl | C | N | C | N | C | C | CH$_3$ | — | H | H | 1A-D, 18D |
| B-43 | CF$_2$Br | C | N | C | N | C | C | CH$_3$ | — | H | H | 1A-D, 18D |
| B-44 | CF$_2$CH$_3$ | C | N | C | N | C | C | CH$_3$ | — | H | H | 1A-D, 18D |
| B-45 | CF$_2$CHF$_2$ | C | N | C | N | C | C | CH$_3$ | — | H | H | 1A-D, 18D |
| B-46 | CF$_2$CF$_3$ | C | N | C | N | C | C | CH$_3$ | — | H | H | 1A-D, 18D |
| B-47 | CF$_3$ | C | N | C | N | C | C | C$_2$H$_5$ | — | H | H | 18D |
| B-48 | CHF$_2$ | C | N | C | N | C | C | C$_2$H$_5$ | — | H | H | 1A-D, 18D |
| B-49 | CF$_2$Cl | C | N | C | N | C | C | C$_2$H$_5$ | — | H | H | 1A-D, 18D |
| B-50 | CF$_2$Br | C | N | C | N | C | C | C$_2$H$_5$ | — | H | H | 1A-D, 18D |
| B-51 | CF$_2$CH$_3$ | C | N | C | N | C | C | C$_2$H$_5$ | — | H | H | 1A-D, 18D |

TABLE B-continued (X = CO, R² = H, R³ = H)

| | | | | | | | | | | | |
|---|---|---|---|---|---|---|---|---|---|---|---|
| B-52 | CF₂CHF₂ | C | N | C | N | C | C | C₂H₅ | — | H | H | 1A-D, 18D |
| B-53 | CF₂CF₃ | C | N | C | N | C | C | C₂H₅ | — | H | H | 1A-D, 18D |
| B-54 | CF₃ | C | N | C | N | C | C | (CH₂)₂CH₃ | — | H | H | 18D |
| B-55 | CHF₂ | C | N | C | N | C | C | (CH₂)₂CH₃ | — | H | H | 1A-D, 18D |
| B-56 | CF₂Cl | C | N | C | N | C | C | (CH₂)₂CH₃ | — | H | H | 1A-D, 18D |
| B-57 | CF₂Br | C | N | C | N | C | C | (CH₂)₂CH₃ | — | H | H | 1A-D, 18D |
| B-58 | CF₂CH₃ | C | N | C | N | C | C | (CH₂)₂CH₃ | — | H | H | 1A-D, 18D |
| B-59 | CF₂CHF₂ | C | N | C | N | C | C | (CH₂)₂CH₃ | — | H | H | 1A-D, 18D |
| B-60 | CF₂CF₃ | C | N | C | N | C | C | (CH₂)₂CH₃ | — | H | H | 1A-D, 18D |
| B-61 | CF₃ | C | N | C | N | C | C | CH(CH₃)₂ | — | H | H | 18D |
| B-62 | CHF₂ | C | N | C | N | C | C | CH(CH₃)₂ | — | H | H | 1A-D, 18D |
| B-63 | CF₂Cl | C | N | C | N | C | C | CH(CH₃)₂ | — | H | H | 1A-D, 18D |
| B-64 | CF₂Br | C | N | C | N | C | C | CH(CH₃)₂ | — | H | H | 1A-D, 18D |
| B-65 | CF₂CH₃ | C | N | C | N | C | C | CH(CH₃)₂ | — | H | H | 1A-D, 18D |
| B-66 | CF₂CHF₂ | C | N | C | N | C | C | CH(CH₃)₂ | — | H | H | 1A-D, 18D |
| B-67 | CF₂CF₃ | C | N | C | N | C | C | CH(CH₃)₂ | — | H | H | 1A-D, 18D |
| B-68 | CF₃ | C | C | N | C | C | N | (CH₂)₂CH₃ | H | H | — | 18D |
| B-69 | CHF₂ | C | C | N | C | C | N | (CH₂)₂CH₃ | H | H | — | 1A-D, 18D |
| B-70 | CF₂Cl | C | C | N | C | C | N | (CH₂)₂CH₃ | H | H | — | 1A-D, 18D |
| B-71 | CF₂Br | C | C | N | C | C | N | (CH₂)₂CH₃ | H | H | — | 1A-D, 18D |
| B-72 | CF₂CH₃ | C | C | N | C | C | N | (CH₂)₂CH₃ | H | H | — | 1A-D, 18D |
| B-73 | CF₂CHF₂ | C | C | N | C | C | N | (CH₂)₂CH₃ | H | H | — | 1A-D, 18D |
| B-74 | CF₂CF₃ | C | C | N | C | C | N | (CH₂)₂CH₃ | H | H | — | 1A-D, 18D |
| B-75 | CF₃ | C | C | N | C | C | N | CH(CH₃)₂ | H | H | — | 18D |
| B-76 | CHF₂ | C | C | N | C | C | N | CH(CH₃)₂ | H | H | — | 1A-D, 18D |
| B-77 | CF₂Cl | C | C | N | C | C | N | CH(CH₃)₂ | H | H | — | 1A-D, 18D |
| B-78 | CF₂Br | C | C | N | C | C | N | CH(CH₃)₂ | H | H | — | 1A-D, 18D |
| B-79 | CF₂CH₃ | C | C | N | C | C | N | CH(CH₃)₂ | H | H | — | 1A-D, 18D |
| B-80 | CF₂CHF₂ | C | C | N | C | C | N | CH(CH₃)₂ | H | H | — | 1A-D, 18D |
| B-81 | CF₂CF₃ | C | C | N | C | C | N | CH(CH₃)₂ | H | H | — | 1A-D, 18D |
| B-82 | CF₃ | N | C | N | C | C | N | (CH₂)₂CH₃ | H | H | — | 1A-D, 18D |
| B-83 | CHF₂ | N | C | N | C | C | N | (CH₂)₂CH₃ | H | H | — | 14A, 1A-D, 18D |
| B-84 | CF₂Cl | N | C | N | C | C | N | (CH₂)₂CH₃ | H | H | — | 14A, 1A-D, 18D |
| B-85 | CF₂Br | N | C | N | C | C | N | (CH₂)₂CH₃ | H | H | — | 14A, 1A-D, 18D |
| B-86 | CF₂CH₃ | N | C | N | C | C | N | (CH₂)₂CH₃ | H | H | — | 14A, 1A-D, 18D |
| B-87 | CF₂CHF₂ | N | C | N | C | C | N | (CH₂)₂CH₃ | H | H | — | 14A, 1A-D, 18D |
| B-88 | CF₂CF₃ | N | C | N | C | C | N | (CH₂)₂CH₃ | H | H | — | 14A, 1A-D, 18D |
| B-89 | CF₃ | N | C | N | C | C | N | CH(CH₃)₂ | H | H | — | 1A-D, 18D |
| B-90 | CHF₂ | N | C | N | C | C | N | CH(CH₃)₂ | H | H | — | 14A, 1A-D, 18D |
| B-91 | CF₂Cl | N | C | N | C | C | N | CH(CH₃)₂ | H | H | — | 14A, 1A-D, 18D |
| B-92 | CF₂Br | N | C | N | C | C | N | CH(CH₃)₂ | H | H | — | 14A, 1A-D, 18D |
| B-93 | CF₂CH₃ | N | C | N | C | C | N | CH(CH₃)₂ | H | H | — | 14A, 1A-D, 18D |
| B-94 | CF₂CHF₂ | N | C | N | C | C | N | CH(CH₃)₂ | H | H | — | 14A, 1A-D, 18D |
| B-95 | CF₂CF₃ | N | C | N | C | C | N | CH(CH₃)₂ | H | H | — | 14A, 1A-D, 18D |
| B-96 | CF₃ | N | C | N | N | C | C | CH₃ | — | H | H | 18D |
| B-97 | CHF₂ | N | C | N | N | C | C | CH₃ | — | H | H | 1A-D, 18D |
| B-98 | CF₂Cl | N | C | N | N | C | C | CH₃ | — | H | H | 1A-D, 18D |
| B-99 | CF₂Br | N | C | N | N | C | C | CH₃ | — | H | H | 1A-D, 18D |
| B-100 | CF₂CH₃ | N | C | N | N | C | C | CH₃ | — | H | H | 1A-D, 18D |
| B-101 | CF₂CHF₂ | N | C | N | N | C | C | CH₃ | — | H | H | 1A-D, 18D |
| B-102 | CF₂CF₃ | N | C | N | N | C | C | CH₃ | — | H | H | 1A-D, 18D |
| B-103 | CF₃ | N | C | N | N | C | C | C₂H₅ | — | H | H | 18D |
| B-104 | CHF₂ | N | C | N | N | C | C | C₂H₅ | — | H | H | 1A-D, 18D |
| B-105 | CF₂Cl | N | C | N | N | C | C | C₂H₅ | — | H | H | 1A-D, 18D |
| B-106 | CF₂Br | N | C | N | N | C | C | C₂H₅ | — | H | H | 1A-D, 18D |
| B-107 | CF₂CH₃ | N | C | N | N | C | C | C₂H₅ | — | H | H | 1A-D, 18D |
| B-108 | CF₂CHF₂ | N | C | N | N | C | C | C₂H₅ | — | H | H | 1A-D, 18D |
| B-109 | CF₂CF₃ | N | C | N | N | C | C | C₂H₅ | — | H | H | 1A-D, 18D |
| B-110 | CF₃ | N | C | N | N | C | C | (CH₂)₂CH₃ | — | H | H | 18D |
| B-111 | CHF₂ | N | C | N | N | C | C | (CH₂)₂CH₃ | — | H | H | 1A-D, 18D |
| B-112 | CF₂Cl | N | C | N | N | C | C | (CH₂)₂CH₃ | — | H | H | 1A-D, 18D |
| B-113 | CF₂Br | N | C | N | N | C | C | (CH₂)₂CH₃ | — | H | H | 1A-D, 18D |
| B-114 | CF₂CH₃ | N | C | N | N | C | C | (CH₂)₂CH₃ | — | H | H | 1A-D, 18D |
| B-115 | CF₂CHF₂ | N | C | N | N | C | C | (CH₂)₂CH₃ | — | H | H | 1A-D, 18D |
| B-116 | CF₂CF₃ | N | C | N | N | C | C | (CH₂)₂CH₃ | — | H | H | 1A-D, 18D |
| B-117 | CF₃ | N | C | N | N | C | C | CH(CH₃)₂ | — | H | H | 1A-D, 18D |
| B-118 | CHF₂ | N | C | N | N | C | C | CH(CH₃)₂ | — | H | H | 14A, 1A-D, 18D |
| B-119 | CF₂Cl | N | C | N | N | C | C | CH(CH₃)₂ | — | H | H | 14A, 1A-D, 18D |
| B-120 | CF₂Br | N | C | N | N | C | C | CH(CH₃)₂ | — | H | H | 14A, 1A-D, 18D |
| B-121 | CF₂CH₃ | N | C | N | N | C | C | CH(CH₃)₂ | — | H | H | 14A, 1A-D, 18D |
| B-122 | CF₂CHF₂ | N | C | N | N | C | C | CH(CH₃)₂ | — | H | H | 14A, 1A-D, 18D |
| B-123 | CF₂CF₃ | N | C | N | N | C | C | CH(CH₃)₂ | — | H | H | 14A, 1A-D, 18D |
| B-124 | CF₃ | N | C | N | N | C | C | CH₃ | — | CH₃ | H | 18D |
| B-125 | CHF₂ | N | C | N | N | C | C | CH₃ | — | CH₃ | H | 1A-D, 18D |
| B-126 | CF₂Cl | N | C | N | N | C | C | CH₃ | — | CH₃ | H | 1A-D, 18D |
| B-127 | CF₂Br | N | C | N | N | C | C | CH₃ | — | CH₃ | H | 1A-D, 18D |
| B-128 | CF₂CH₃ | N | C | N | N | C | C | CH₃ | — | CH₃ | H | 1A-D, 18D |
| B-129 | CF₂CHF₂ | N | C | N | N | C | C | CH₃ | — | CH₃ | H | 1A-D, 18D |

TABLE B-continued ($X = CO$, $R^2 = H$, $R^3 = H$)

| No | | | | | | | | | | | |
|---|---|---|---|---|---|---|---|---|---|---|---|
| B-130 | $CF_2CF_3$ | N | C | N | N | C | C | $CH_3$ | — | $CH_3$ | H | 1A-D, 18D |
| B-131 | $CF_3$ | N | C | N | N | C | N | $CH_3$ | H | $CH_3$ | H | 18D |
| B-132 | $CHF_2$ | N | C | N | C | C | N | $CH_3$ | H | $CH_3$ | H | 1A-D, 18D |
| B-133 | $CF_2Cl$ | N | C | N | C | C | N | $CH_3$ | H | $CH_3$ | H | 1A-D, 18D |
| B-134 | $CF_2Br$ | N | C | N | C | C | N | $CH_3$ | H | $CH_3$ | H | 1A-D, 18D |
| B-135 | $CF_2CH_3$ | N | C | N | C | C | N | $CH_3$ | H | $CH_3$ | H | 1A-D, 18D |
| B-136 | $CF_2CHF_2$ | N | C | N | C | C | N | $CH_3$ | H | $CH_3$ | H | 1A-D, 18D |
| B-137 | $CF_2CF_3$ | N | C | N | C | C | N | $CH_3$ | H | $CH_3$ | H | 1A-D, 18D |
| B-138 | $CF_3$ | C | N | N | C | C | C | — | $CH_3$ | H | $CH_3$ | 18D |
| B-139 | $CHF_2$ | C | N | N | C | C | C | — | $CH_3$ | H | $CH_3$ | 1A-D, 18D |
| B-140 | $CF_2Cl$ | C | N | N | C | C | C | — | $CH_3$ | H | $CH_3$ | 1A-D, 18D |
| B-141 | $CF_2Br$ | C | N | N | C | C | C | — | $CH_3$ | H | $CH_3$ | 1A-D, 18D |
| B-142 | $CF_2CH_3$ | C | N | N | C | C | C | — | $CH_3$ | H | $CH_3$ | 1A-D, 18D |
| B-143 | $CF_2CHF_2$ | C | N | N | C | C | C | — | $CH_3$ | H | $CH_3$ | 1A-D, 18D |
| B-144 | $CF_2CF_3$ | C | N | N | C | C | C | — | $CH_3$ | H | $CH_3$ | 1A-D, 18D |
| B-145 | $CF_3$ | C | C | N | C | N | C | $CH_3$ | H | — | H | 18D |
| B-146 | $CHF_2$ | C | C | N | C | N | C | $CH_3$ | H | — | H | 1A-D, 18D |
| B-147 | $CF_2Cl$ | C | C | N | C | N | C | $CH_3$ | H | — | H | 1A-D, 18D |
| B-148 | $CF_2Br$ | C | C | N | C | N | C | $CH_3$ | H | — | H | 1A-D, 18D |
| B-149 | $CF_2CH_3$ | C | C | N | C | N | C | $CH_3$ | H | — | H | 1A-D, 18D |
| B-150 | $CF_2CHF_2$ | C | C | N | C | N | C | $CH_3$ | H | — | H | 1A-D, 18D |
| B-151 | $CF_2CF_3$ | C | C | N | C | N | C | $CH_3$ | H | — | H | 1A-D, 18D |
| B-152 | $CF_3$ | C | C | N | C | N | C | $C_2H_5$ | H | — | H | 18D |
| B-153 | $CHF_2$ | C | C | N | C | N | C | $C_2H_5$ | H | — | H | 1A-D, 18D |
| B-154 | $CF_2Cl$ | C | C | N | C | N | C | $C_2H_5$ | H | — | H | 1A-D, 18D |
| B-155 | $CF_2Br$ | C | C | N | C | N | C | $C_2H_5$ | H | — | H | 1A-D, 18D |
| B-156 | $CF_2CH_3$ | C | C | N | C | N | C | $C_2H_5$ | H | — | H | 1A-D, 18D |
| B-157 | $CF_2CHF_2$ | C | C | N | C | N | C | $C_2H_5$ | H | — | H | 1A-D, 18D |
| B-158 | $CF_2CF_3$ | C | C | N | C | N | C | $C_2H_5$ | H | — | H | 1A-D, 18D |
| B-159 | $CF_3$ | C | C | N | C | N | C | $(CH_2)_2CH_3$ | H | — | H | 18D |
| B-160 | $CHF_2$ | C | C | N | C | N | C | $(CH_2)_2CH_3$ | H | — | H | 1A-D, 18D |
| B-161 | $CF_2Cl$ | C | C | N | C | N | C | $(CH_2)_2CH_3$ | H | — | H | 1A-D, 18D |
| B-162 | $CF_2Br$ | C | C | N | C | N | C | $(CH_2)_2CH_3$ | H | — | H | 1A-D, 18D |
| B-163 | $CF_2CH_3$ | C | C | N | C | N | C | $(CH_2)_2CH_3$ | H | — | H | 1A-D, 18D |
| B-164 | $CF_2CHF_2$ | C | C | N | C | N | C | $(CH_2)_2CH_3$ | H | — | H | 1A-D, 18D |
| B-165 | $CF_2CF_3$ | C | C | N | C | N | C | $(CH_2)_2CH_3$ | H | — | H | 1A-D, 18D |
| B-166 | $CF_3$ | C | C | N | C | N | C | $CH(CH_3)_2$ | H | — | H | 18D |
| B-167 | $CHF_2$ | C | C | N | C | N | C | $CH(CH_3)_2$ | H | — | H | 1A-D, 18D |
| B-168 | $CF_2Cl$ | C | C | N | C | N | C | $CH(CH_3)_2$ | H | — | H | 1A-D, 18D |
| B-169 | $CF_2Br$ | C | C | N | C | N | C | $CH(CH_3)_2$ | H | — | H | 1A-D, 18D |
| B-170 | $CF_2CH_3$ | C | C | N | C | N | C | $CH(CH_3)_2$ | H | — | H | 1A-D, 18D |
| B-171 | $CF_2CHF_2$ | C | C | N | C | N | C | $CH(CH_3)_2$ | H | — | H | 1A-D, 18D |
| B-172 | $CF_2CF_3$ | C | C | N | C | N | C | $CH(CH_3)_2$ | H | — | H | 1A-D, 18D |

Further examples of specific compounds of the present invention include each of the compounds of table B above wherein $X=SO_2$ instead of CO and each of the compounds of table B wherein $X=CS$ instead of CO.

Table C below provides for each of the synthesized compounds of the formula (C) the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis.

If a compound contains one or more chiral centers, the absolute configuration of the synthesized compound is indicated in the column R/S, wherein "RS" means a racemate,

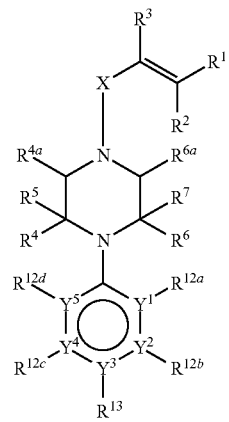

Formula (C)

TABLE C ($X = CO$, $R^2 = H$, $R^3 = H$, $Y^3 = H$, $Y^4 = H$, $Y^5 = H$)

| No | $R^1$ | $R^4$ | $R^5$ | $R^{4a}$ | $R^6$ | $R^7$ | $R^{6a}$ | R/S | $Y^1$ | $Y^2$ | $R^{12a}$ | $R^{12b}$ | $R^{13}$ | $R^{12c}$ | $R^{12d}$ | HPLC | Rt | m/z | MW |
|---|---|---|---|---|---|---|---|---|---|---|---|---|---|---|---|---|---|---|---|
| C-1 | $CF_3$ | H | H | $CH_2$ | H | H | | S, S | N | C | — | H | H | $CH_3$ | H | 2 | 0.95 | 312.1 | 311.3 |
| C-2 | $CF_3$ | H | H | $CH_2$ | H | H | | S, S | C | N | $CH_3$ | — | H | H | H | 2 | 0.85 | 312.1 | 311.3 |

TABLE C-continued (X = CO, $R^2$ = H, $R^3$ = H, $Y^3$ = H, $Y^4$ = H, $Y^5$ = H)

| No | $R^1$ | $R^4$ | $R^5$ | $R^{4a}$ | $R^6$ | $R^7$ | $R^{6a}$ | R/S | $Y^1$ | $Y^2$ | $R^{12a}$ | $R^{12b}$ | $R^{13}$ | $R^{12c}$ | $R^{12d}$ | HPLC | Rt | m/z | MW |
|---|---|---|---|---|---|---|---|---|---|---|---|---|---|---|---|---|---|---|---|
| C-3 | CH(CH$_3$)$_2$ | H | H | CH$_2$ | | H | H | S,S | N | C | — | H | H | CH$_3$ | H | 2 | 0.96 | 286.1 | 285.4 |
| C-4 | CH(CH$_3$)$_2$ | H | H | CH$_2$ | | H | H | S,S | C | N | CH$_3$ | — | H | H | H | 2 | 0.86 | 286.1 | 285.4 |
| C-5 | CF$_3$ | H | H | CH$_3$ | H | H | H | RS | N | C | — | H | H | CH$_3$ | H | 2 | 1.05 | 314.1 | 313.3 |
| C-6 | CF$_3$ | H | H | phenyl | H | H | H | RS | N | C | — | H | H | CH$_3$ | H | 2 | 1.16 | 376.1 | 375.4 |
| C-7 | CF$_3$ | H | H | benzyl | H | H | H | RS | N | C | — | H | H | CH$_3$ | H | 2 | 1.19 | 390.2 | 389.4 |
| C-8 | CF$_3$ | H | H | CH$_3$ | H | H | H | RS | C | N | CH$_3$ | — | H | H | H | 2 | 0.95 | 314.2 | 313.3 |
| C-9 | CF$_3$ | H | H | phenyl | H | H | H | RS | C | N | CH$_3$ | — | H | H | H | 2 | 1.06 | 376.2 | 375.4 |
| C-10 | CF$_3$ | H | H | benzyl | H | H | H | RS | C | N | CH$_3$ | — | H | H | H | 2 | 1.08 | 390.2 | 389.4 |
| C-11 | CF$_3$ | H | H | CH$_2$CH$_3$ | H | H | H | RS | C | N | CH$_3$ | — | H | H | H | 2 | 1.00 | 328.2 | 327.3 |
| C-12 | CF$_3$ | CH$_3$ | H | CH$_3$ | H | H | H | RS | C | N | H | — | H | CH$_3$ | H | 2 | 0.99 | 328.1 | 327.3 |
| C-13 | CF$_3$ | CH$_3$ | H | H | H | H | H | RS | C | N | H | — | H | CH$_3$ | H | 2 | 0.93 | 314.1 | 313.3 |
| C-14 | CF$_3$ | H | H | CH$_3$ | H | H | CH$_3$ | RS | C | N | H | — | H | CH$_3$ | H | 2 | 1.01 | 328.1 | 327.3 |
| C-15 | CF$_3$ | CH$_3$ | CH$_3$ | H | H | H | H | — | C | N | H | — | H | CH$_3$ | H | 2 | 0.97 | 328.1 | 327.3 |
| C-16 | CF$_3$ | CH$_2$CH$_3$ | H | H | H | H | H | RS | C | N | H | — | H | CH$_3$ | H | 2 | 0.99 | 328.1 | 327.3 |
| C-17 | CF$_3$ | CH$_3$ | H | H | CH$_3$ | H | H | RS | C | N | H | — | H | CH$_3$ | H | 1 | 3.61 | 328.2 | 327.3 |
| C-18 | CF$_3$ | H | H | C$_2$H5 | H | H | H | RS | N | C | — | H | H | CH$_3$ | H | 2 | 1.10 | 328.1 | 327.3 |

Further examples of specific compounds of the present invention include each of the compounds of table C above wherein X=SO$_2$ instead of CO and each of the compounds of table C wherein X=CS instead of CO.

Table D below provides for each of the synthesized compounds of the formula (D) the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis. From compound D-48 until to the end of the table the methods by which the compounds are synthesized are identified by referring to the synthesis steps described in the synthesis examples of paragraph B above ("Synthesis Examples").

If a compound contains a chiral center, the absolute configuration of the synthesized compound is indicated in the column R/S, wherein "RS" means a racemate.

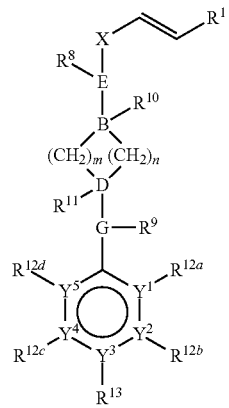

Formula (D)

TABLE D (X = CO, $Y^3$, $Y^4$, $Y^5$ = C)

| No | $R^1$ | E | $R^8$ | B | $R^{10}$ | D | $R^{11}$ | G | $R^9$ | m | n | R/S | $Y^1$ | $Y^2$ | $R^{12a}$ | $R^{12b}$ | $R^{13}$ | $R^{12c}$ | $R^{12d}$ | HPLC | Rt | m/z | MW |
|---|---|---|---|---|---|---|---|---|---|---|---|---|---|---|---|---|---|---|---|---|---|---|---|
| D-1 | CF$_3$ | N | H | C | H | N | — | — | — | 2 | 1 | S | C | N | H | — | H | CH$_3$ | H | 1 | 3.41 | 300.2 | 299.3 |
| D-2 | CF$_3$ | — | — | N | — | C | H | N | H | 3 | 1 | S | C | N | H | — | H | CH$_3$ | H | 1 | 3.34 | 314.2 | 313.3 |
| D-3 | CF$_3$ | N | H | C | H | N | — | — | — | 2 | 1 | R | C | N | H | — | H | CH$_3$ | H | 1 | 3.41 | 300.2 | 299.3 |
| D-4 | CF$_3$ | N | H | C | H | N | — | — | — | 3 | 1 | S | C | N | H | — | H | CH$_3$ | H | 1 | 3.48 | 314.2 | 313.3 |
| D-5 | CF$_3$ | N | H | C | H | N | — | — | — | 3 | 1 | R | C | N | H | — | H | CH$_3$ | H | 1 | 3.48 | 314.2 | 313.3 |

TABLE D-continued (X = CO, Y³, Y⁴, Y⁵ = C)

| ID | | | | | | | | | | | | | | | | | | | | | | | |
|---|---|---|---|---|---|---|---|---|---|---|---|---|---|---|---|---|---|---|---|---|---|---|---|
| D-6 | $CF_3$ | — | — | N | — | N | — | — | — | 3 | 2 | — | C | N | H | — | H | $CH_3$ | H | 1 | 3.31 | 314.2 | 313.3 |
| D-7 | $CF_3$ | — | — | N | — | C | H | N | H | 1 | 2 | R | C | N | H | — | H | $CH_3$ | H | 1 | 3.20 | 300.2 | 299.3 |
| D-8 | $CF_3$ | — | — | N | — | C | H | N | H | 3 | 1 | R | C | N | H | — | H | $CH_3$ | H | 1 | 3.34 | 314.2 | 313.3 |
| D-9 | $CF_3$ | N | H | C | H | N | — | — | — | 2 | 1 | S | N | C | — | H | H | $CH_3$ | H | 1 | 3.57 | 300.2 | 299.3 |
| D-10 | $CF_3$ | — | — | N | — | C | H | N | H | 3 | 1 | S | N | C | — | H | H | $CH_3$ | H | 1 | 3.69 | 314.2 | 313.3 |
| D-11 | $CF_3$ | N | H | C | H | N | — | — | — | 2 | 1 | R | N | C | — | H | H | $CH_3$ | H | 1 | 3.56 | 300.2 | 299.3 |
| D-12 | $CF_3$ | N | H | C | H | N | — | — | — | 3 | 1 | S | N | C | — | H | H | $CH_3$ | H | 1 | 3.84 | 314.2 | 313.3 |
| D-13 | $CF_3$ | N | H | C | H | N | — | — | — | 3 | 1 | R | N | C | — | H | H | $CH_3$ | H | 1 | 3.85 | 314.3 | 313.3 |
| D-14 | $CF_3$ | — | — | N | — | N | — | — | — | 3 | 2 | — | N | C | — | H | H | $CH_3$ | H | 1 | 3.74 | 314.2 | 313.3 |
| D-15 | $CF_2CH_3$ | N | H | C | H | N | — | — | — | 2 | 1 | S | C | N | H | — | H | $CH_3$ | H | 1 | 3.28 | 296.2 | 295.3 |
| D-16 | $CF_2CH_3$ | N | H | C | H | N | — | — | — | 2 | 1 | R | C | N | H | — | H | $CH_3$ | H | 1 | 3.28 | 296.2 | 295.3 |
| D-17 | $CF_2CH_3$ | — | — | N | — | C | H | N | H | 3 | 1 | S | C | N | H | — | H | $CH_3$ | H | 1 | 3.24 | 310.2 | 309.4 |
| D-18 | $CF_2CH_3$ | — | — | N | — | C | H | N | H | 3 | 1 | R | C | N | H | — | H | $CH_3$ | H | 1 | 3.24 | 310.2 | 309.4 |
| D-19 | $CF_2CH_3$ | N | H | C | H | N | — | — | — | 3 | 1 | S | C | N | H | — | H | $CH_3$ | H | 1 | 3.35 | 310.2 | 309.4 |
| D-20 | $CF_2CH_3$ | N | H | C | H | N | — | — | — | 3 | 1 | R | C | N | H | — | H | $CH_3$ | H | 1 | 3.35 | 310.2 | 309.4 |
| D-21 | $CF_2CH_3$ | — | — | N | — | N | — | — | — | 3 | 2 | — | C | N | H | — | H | $CH_3$ | H | 1 | 3.22 | 310.2 | 309.4 |
| D-22 | $CF_2CH_3$ | N | H | C | H | N | — | — | — | 2 | 1 | S | N | C | — | H | H | $CH_3$ | H | 1 | 3.44 | 296.2 | 295.3 |
| D-23 | $CF_2CH_3$ | N | H | C | H | N | — | — | — | 2 | 1 | R | N | C | — | H | H | $CH_3$ | H | 1 | 3.44 | 296.2 | 295.3 |
| D-24 | $CF_2CH_3$ | — | — | N | — | C | H | N | H | 3 | 1 | S | N | C | — | H | H | $CH_3$ | H | 1 | 3.55 | 310.2 | 309.4 |
| D-25 | $CH(CH_3)_2$ | N | H | C | H | N | — | — | — | 2 | 1 | S | C | N | H | — | H | $CH_3$ | H | 1 | 3.38 | 274.2 | 273.4 |
| D-26 | $CH(CH_3)_2$ | N | H | C | H | N | — | — | — | 2 | 1 | R | C | N | H | — | H | $CH_3$ | H | 1 | 3.38 | 274.2 | 273.4 |
| D-27 | $CH(CH_3)_2$ | — | — | N | — | C | H | N | H | 3 | 1 | S | C | N | H | — | H | $CH_3$ | H | 1 | 3.39 | 288.3 | 287.4 |
| D-28 | $CH(CH_3)_2$ | — | — | N | — | C | H | N | H | 3 | 1 | R | C | N | H | — | H | $CH_3$ | H | 1 | 3.39 | 288.3 | 287.4 |
| D-29 | $CH(CH_3)_2$ | N | H | C | H | N | — | — | — | 3 | 1 | R | C | N | H | — | H | $CH_3$ | H | 1 | 3.46 | 288.3 | 287.4 |
| D-30 | $CH(CH_3)_2$ | N | H | C | H | N | — | — | — | 3 | 1 | S | C | N | H | — | H | $CH_3$ | H | 1 | 3.46 | 288.3 | 287.4 |
| D-31 | $CH(CH_3)_2$ | — | — | N | — | N | — | — | — | 3 | 2 | — | C | N | H | — | H | $CH_3$ | H | 1 | 3.37 | 288.3 | 287.4 |
| D-32 | $CH(CH_3)_2$ | — | — | N | — | C | H | N | H | 1 | 2 | R | C | N | H | — | H | $CH_3$ | H | 1 | 3.24 | 274.2 | 273.4 |
| D-33 | $CH(CH_3)_2$ | N | H | C | H | N | — | — | — | 2 | 1 | S | N | C | — | H | H | $CH_3$ | H | 1 | 3.53 | 274.2 | 273.4 |
| D-34 | $CH(CH_3)_2$ | N | H | C | H | N | — | — | — | 2 | 1 | R | N | C | — | H | H | $CH_3$ | H | 1 | 3.53 | 274.2 | 273.4 |
| D-35 | $CH(CH_3)_2$ | — | — | N | — | C | H | N | H | 3 | 1 | S | N | C | — | H | H | $CH_3$ | H | 1 | 3.71 | 288.3 | 287.4 |
| D-36 | $CF_3$ | — | — | N | — | C | H | N | H | 1 | 2 | S | C | N | H | — | H | $CH_3$ | H | 2 | 0.86 | 300.1 | 299.3 |
| D-37 | $CF_3$ | N | H | C | H | N | — | — | — | 1 | 1 | — | N | C | — | H | H | $CH_3$ | H | 2 | 0.91 | 286.1 | 285.3 |
| D-38 | $CF_3$ | — | — | N | — | C | H | N | H | 1 | 2 | S | C | N | H | — | H | $CH_3$ | H | 2 | 0.93 | 300.1 | 299.3 |
| D-39 | $CF_3$ | — | — | N | — | C | H | N | H | 1 | 2 | R | C | N | H | — | H | $CH_3$ | H | 2 | 0.93 | 300.1 | 299.3 |
| D-40 | $CF_3$ | — | — | N | — | C | H | N | H | 3 | 1 | R | C | N | H | — | H | $CH_3$ | H | 2 | 0.99 | 314.0 | 313.3 |
| D-41 | $CF_3$ | N | H | C | H | N | — | — | — | 1 | 1 | — | C | N | H | — | H | $CH_3$ | H | 4 | 1.32 | 286.1 | 285.3 |
| D-42 | $CF_3$ | — | — | N | — | C | H | N | H | 1 | 1 | — | C | N | H | — | H | $CH_3$ | H | 1 | 3.12 | 286.1 | 285.3 |
| D-43 | $CF_3$ | — | — | N | — | C | H | N | H | 1 | 1 | — | N | C | — | H | H | $CH_3$ | H | 1 | 3.39 | 286.1 | 285.3 |
| D-44 | $CH(CH_3)_2$ | N | H | C | H | N | — | — | — | 3 | 1 | S | N | C | — | H | H | $CH_3$ | H | 2 | 1.04 | 288.2 | 287.4 |

TABLE D-continued (X = CO, Y³, Y⁴, Y⁵ = C)

| No | R¹ | | | | | | | | m | n | R/S | Y¹ | Y² | R¹²ᵃ | R¹²ᵇ | R¹³ | R¹²ᶜ | R¹²ᵈ | | | |
|---|---|---|---|---|---|---|---|---|---|---|---|---|---|---|---|---|---|---|---|---|---|
| D-45 | CH(CH₃)₂ | — | — | N | — | N | — | — | — | 3 | 2 | — | N | C | — | H | H | CH₃ | H | 2 | 1.03 | 288.2 | 287.4 |
| D-46 | CF₂CH₃ | — | — | N | — | C | H | N | H | 1 | 2 | S | N | C | — | H | H | CH₃ | H | 2 | 0.92 | 296.1 | 295.3 |
| D-47 | CF₂CH₃ | — | — | N | — | C | H | N | H | 1 | 2 | R | N | C | — | H | H | CH₃ | H | 2 | 0.92 | 296.1 | 295.3 |

| No | R¹ | E | R⁸ | B | R¹⁰ | D | R¹¹ | G | R⁹ | m | n | R/S | Y¹ | Y² | R¹²ᵃ | R¹²ᵇ | R¹³ | R¹²ᶜ | R¹²ᵈ | Synth. method |
|---|---|---|---|---|---|---|---|---|---|---|---|---|---|---|---|---|---|---|---|---|
| D-48 | CF₂Cl | N | H | C | H | N | — | — | — | 2 | 1 | S | C | N | H | — | H | CH₃ | H | 5A-B, 1A-D, 18D |
| D-49 | CF₂Br | N | H | C | H | N | — | — | — | 2 | 1 | S | C | N | H | — | H | CH₃ | H | 5A-B, 1A-D, 18D |
| D-50 | CHF₂ | N | H | C | H | N | — | — | — | 2 | 1 | S | C | N | H | — | H | CH₃ | H | 5A-B, 1A-D, 18D |
| D-51 | CF₂HCF₃ | N | H | C | H | N | — | — | — | 2 | 1 | S | C | N | H | — | H | CH₃ | H | 5A-B, 1A-D, 18D |
| D-52 | CF₂CF₃ | N | H | C | H | N | — | — | — | 2 | 1 | S | C | N | H | — | H | CH₃ | H | 5A-B, 1A-D, 18D |
| D-53 | CF₃ | N | H | C | H | N | — | — | — | 2 | 1 | S | C | N | H | — | H | C₂H₅ | H | 5A-B, 1A-D, 18D |
| D-54 | CF₂Cl | N | H | C | H | N | — | — | — | 2 | 1 | S | C | N | H | — | H | C₂H₅ | H | 5A-B, 1A-D, 18D |
| D-55 | CF₂Br | N | H | C | H | N | — | — | — | 2 | 1 | S | C | N | H | — | H | C₂H₅ | H | 5A-B, 1A-D, 18D |
| D-56 | CHF₂ | N | H | C | H | N | — | — | — | 2 | 1 | S | C | N | H | — | H | C₂H₅ | H | 5A-B, 1A-D, 18D |
| D-57 | CF₂CH₃ | N | H | C | H | N | — | — | — | 2 | 1 | S | C | N | H | — | H | C₂H₅ | H | 5A-B, 1A-D, 18D |
| D-58 | CF₂HCF₃ | N | H | C | H | N | — | — | — | 2 | 1 | S | C | N | H | — | H | C₂H₅ | H | 5A-B, 1A-D, 18D |
| D-59 | CF₂CF₃ | N | H | C | H | N | — | — | — | 2 | 1 | S | C | N | H | — | H | C₂H₅ | H | 5A-B, 1A-D, 18D |
| D-60 | CF₃ | N | H | C | H | N | — | — | — | 2 | 1 | S | C | N | CH₃ | — | H | CH₃ | H | 5A-B, 1A-D, 18D |
| D-61 | CF₂Cl | N | H | C | H | N | — | — | — | 2 | 1 | S | C | N | CH₃ | — | H | CH₃ | H | 5A-B, 1A-D, 18D |
| D-62 | CF₂Br | N | H | C | H | N | — | — | — | 2 | 1 | S | C | N | CH₃ | — | H | CH₃ | H | 5A-B, 1A-D, 18D |
| D-63 | CHF₂ | N | H | C | H | N | — | — | — | 2 | 1 | S | C | N | CH₃ | — | H | CH₃ | H | 5A-B, 1A-D, 18D |
| D-64 | CF₂CH₃ | N | H | C | H | N | — | — | — | 2 | 1 | S | C | N | CH₃ | — | H | CH₃ | H | 5A-B, 1A-D, 18D |
| D-65 | CF₂HCF₃ | N | H | C | H | N | — | — | — | 2 | 1 | S | C | N | CH₃ | — | H | CH₃ | H | 5A-B, 1A-D, 18D |
| D-66 | CF₂CF₃ | N | H | C | H | N | — | — | — | 2 | 1 | S | C | N | CH₃ | — | H | CH₃ | H | 5A-B, 1A-D, 18D |
| D-67 | CF₃ | N | H | C | H | N | — | — | — | 2 | 1 | S | C | N | H | — | H | H | CH₃ | 5A-B, 1A-D, 18D |
| D-68 | CF₂Cl | N | H | C | H | N | — | — | — | 2 | 1 | S | C | N | H | — | H | H | CH₃ | 5A-B, 1A-D, 18D |
| D-69 | CF₂Br | N | H | C | H | N | — | — | — | 2 | 1 | S | C | N | H | — | H | H | CH₃ | 5A-B, 1A-D, 18D |
| D-70 | CHF₂ | N | H | C | H | N | — | — | — | 2 | 1 | S | C | N | H | — | H | H | CH₃ | 5A-B, 1A-D, 18D |
| D-71 | CF₂CH₃ | N | H | C | H | N | — | — | — | 2 | 1 | S | C | N | H | — | H | H | CH₃ | 5A-B, 1A-D, 18D |
| D-72 | CF₂HCF₃ | N | H | C | H | N | — | — | — | 2 | 1 | S | C | N | H | — | H | H | CH₃ | 5A-B, 1A-D, 18D |
| D-73 | CF₂CF₃ | N | H | C | H | N | — | — | — | 2 | 1 | S | C | N | H | — | H | H | CH₃ | 5A-B, 1A-D, 18D |
| D-74 | CF₂Cl | — | — | N | — | C | H | N | H | 1 | 2 | S | C | N | H | — | H | CH₃ | H | 8A-B, 1A-D, 18D |
| D-75 | CF₂Br | — | — | N | — | C | H | N | H | 1 | 2 | S | C | N | H | — | H | CH₃ | H | 8A-B, 1A-D, 18D |
| D-76 | CHF₂ | — | — | N | — | C | H | N | H | 1 | 2 | S | C | N | H | — | H | CH₃ | H | 8A-B, 1A-D, 18D |
| D-77 | CF₂HCF₃ | — | — | N | — | C | H | N | H | 1 | 2 | S | C | N | H | — | H | CH₃ | H | 8A-B, 1A-D, 18D |
| D-78 | CF₂CF₃ | — | — | N | — | C | H | N | H | 1 | 2 | S | C | N | H | — | H | CH₃ | H | 8A-B, 1A-D, 18D |
| D-79 | CF₃ | — | — | N | — | C | H | N | H | 1 | 2 | S | C | N | H | — | H | C₂H₅ | H | 8A-B, 1A-D, 18D |
| D-80 | CF₂Cl | — | — | N | — | C | H | N | H | 1 | 2 | S | C | N | H | — | H | C₂H₅ | H | 8A-B, 1A-D, 18D |
| D-81 | CF₂Br | — | — | N | — | C | H | N | H | 1 | 2 | S | C | N | H | — | H | C₂H₅ | H | 8A-B, 1A-D, 18D |
| D-82 | CHF₂ | — | — | N | — | C | H | N | H | 1 | 2 | S | C | N | H | — | H | C₂H₅ | H | 8A-B, 1A-D, 18D |
| D-83 | CF₂CH₃ | — | — | N | — | C | H | N | H | 1 | 2 | S | C | N | H | — | H | C₂H₅ | H | 8A-B, 1A-D, 18D |
| D-84 | CF₂HCF₃ | — | — | N | — | C | H | N | H | 1 | 2 | S | C | N | H | — | H | C₂H₅ | H | 8A-B, 1A-D, 18D |
| D-85 | CF₂CF₃ | — | — | N | — | C | H | N | H | 1 | 2 | S | C | N | H | — | H | C₂H₅ | H | 8A-B, 1A-D, 18D |
| D-86 | CF₃ | — | — | N | — | C | H | N | H | 1 | 2 | S | C | N | CH₃ | — | H | CH₃ | H | 8A-B, 1A-D, 18D |
| D-87 | CF₂Cl | — | — | N | — | C | H | N | H | 1 | 2 | S | C | N | CH₃ | — | H | CH₃ | H | 8A-B, 1A-D, 18D |
| D-88 | CF₂Br | — | — | N | — | C | H | N | H | 1 | 2 | S | C | N | CH₃ | — | H | CH₃ | H | 8A-B, 1A-D, 18D |
| D-89 | CHF₂ | — | — | N | — | C | H | N | H | 1 | 2 | S | C | N | CH₃ | — | H | CH₃ | H | 8A-B, 1A-D, 18D |
| D-90 | CF₂CH₃ | — | — | N | — | C | H | N | H | 1 | 2 | S | C | N | CH₃ | — | H | CH₃ | H | 8A-B, 1A-D, 18D |
| D-91 | CF₂HCF₃ | — | — | N | — | C | H | N | H | 1 | 2 | S | C | N | CH₃ | — | H | CH₃ | H | 8A-B, 1A-D, 18D |
| D-92 | CF₂CF₃ | — | — | N | — | C | H | N | H | 1 | 2 | S | C | N | CH₃ | — | H | CH₃ | H | 8A-B, 1A-D, 18D |
| D-93 | CF₃ | — | — | N | — | C | H | N | H | 1 | 2 | S | C | N | H | — | H | H | CH₃ | 8A-B, 1A-D, 18D |
| D-94 | CF₂Cl | — | — | N | — | C | H | N | H | 1 | 2 | S | C | N | H | — | H | H | CH₃ | 8A-B, 1A-D, 18D |
| D-95 | CF₂Br | — | — | N | — | C | H | N | H | 1 | 2 | S | C | N | H | — | H | H | CH₃ | 8A-B, 1A-D, 18D |
| D-96 | CHF₂ | — | — | N | — | C | H | N | H | 1 | 2 | S | C | N | H | — | H | H | CH₃ | 8A-B, 1A-D, 18D |
| D-97 | CF₂CH₃ | — | — | N | — | C | H | N | H | 1 | 2 | S | C | N | H | — | H | H | CH₃ | 8A-B, 1A-D, 18D |
| D-98 | CF₂HCF₃ | — | — | N | — | C | H | N | H | 1 | 2 | S | C | N | H | — | H | H | CH₃ | 8A-B, 1A-D, 18D |
| D-99 | CF₂CF₃ | — | — | N | — | C | H | N | H | 1 | 2 | S | C | N | H | — | H | H | CH₃ | 8A-B, 1A-D, 18D |
| D-100 | CF₂Cl | N | H | C | H | N | — | — | — | 2 | 1 | S | N | C | — | H | H | CH₃ | H | 7A-B, 1A-D, 18D |
| D-101 | CF₂Br | N | H | C | H | N | — | — | — | 2 | 1 | S | N | C | — | H | H | CH₃ | H | 7A-B, 1A-D, 18D |
| D-102 | CHF₂ | N | H | C | H | N | — | — | — | 2 | 1 | S | N | C | — | H | H | CH₃ | H | 7A-B, 1A-D, 18D |
| D-103 | CF₂HCF₃ | N | H | C | H | N | — | — | — | 2 | 1 | S | N | C | — | H | H | CH₃ | H | 7A-B, 1A-D, 18D |
| D-104 | CF₂CF₃ | N | H | C | H | N | — | — | — | 2 | 1 | S | N | C | — | H | H | CH₃ | H | 7A-B, 1A-D, 18D |
| D-105 | CF₃ | N | H | C | H | N | — | — | — | 2 | 1 | S | N | C | — | H | H | C₂H₅ | H | 7A-B, 1A-D, 18D |
| D-106 | CF₂Cl | N | H | C | H | N | — | — | — | 2 | 1 | S | N | C | — | H | H | C₂H₅ | H | 7A-B, 1A-D, 18D |
| D-107 | CF₂Br | N | H | C | H | N | — | — | — | 2 | 1 | S | N | C | — | H | H | C₂H₅ | H | 7A-B, 1A-D, 18D |
| D-108 | CHF₂ | N | H | C | H | N | — | — | — | 2 | 1 | S | N | C | — | H | H | C₂H₅ | H | 7A-B, 1A-D, 18D |
| D-109 | CF₂CH₃ | N | H | C | H | N | — | — | — | 2 | 1 | S | N | C | — | H | H | C₂H₅ | H | 7A-B, 1A-D, 18D |
| D-110 | CF₂HCF₃ | N | H | C | H | N | — | — | — | 2 | 1 | S | N | C | — | H | H | C₂H₅ | H | 7A-B, 1A-D, 18D |
| D-111 | CF₂CF₃ | N | H | C | H | N | — | — | — | 2 | 1 | S | N | C | — | H | H | C₂H₅ | H | 7A-B, 1A-D, 18D |
| D-112 | CF₃ | N | H | C | H | N | — | — | — | 2 | 1 | S | N | C | — | CH₃ | H | H | H | 7A-B, 1A-D, 18D |
| D-113 | CF₂Cl | N | H | C | H | N | — | — | — | 2 | 1 | S | N | C | — | CH₃ | H | H | H | 7A-B, 1A-D, 18D |
| D-114 | CF₂Br | N | H | C | H | N | — | — | — | 2 | 1 | S | N | C | — | CH₃ | H | H | H | 7A-B, 1A-D, 18D |
| D-115 | CHF₂ | N | H | C | H | N | — | — | — | 2 | 1 | S | N | C | — | CH₃ | H | H | H | 7A-B, 1A-D, 18D |

TABLE D-continued (X = CO, Y³, Y⁴, Y⁵ = C)

| | | | | | | | | | | | | | | | | | | | | |
|---|---|---|---|---|---|---|---|---|---|---|---|---|---|---|---|---|---|---|---|---|
| D-116 | CF$_2$CH$_3$ | N | H | C | H | N | — | — | — | 2 | 1 | S | N | C | — | CH$_3$ | H | H | H | 7A-B, 1A-D, 18D |
| D-117 | CF$_2$HCF$_3$ | N | H | C | H | N | — | — | — | 2 | 1 | S | N | C | — | CH$_3$ | H | H | H | 7A-B, 1A-D, 18D |
| D-118 | CF$_2$CF$_3$ | N | H | C | H | N | — | — | — | 2 | 1 | S | N | C | — | CH$_3$ | H | H | H | 7A-B, 1A-D, 18D |
| D-119 | CF$_3$ | N | H | C | H | N | — | — | — | 2 | 1 | S | N | C | — | CH$_3$ | H | CH$_3$ | H | 7A-B, 1A-D, 18D |
| D-120 | CF$_2$Cl | N | H | C | H | N | — | — | — | 2 | 1 | S | N | C | — | CH$_3$ | H | CH$_3$ | H | 7A-B, 1A-D, 18D |
| D-121 | CF$_2$Br | N | H | C | H | N | — | — | — | 2 | 1 | S | N | C | — | CH$_3$ | H | CH$_3$ | H | 7A-B, 1A-D, 18D |
| D-122 | CHF$_2$ | N | H | C | H | N | — | — | — | 2 | 1 | S | N | C | — | CH$_3$ | H | CH$_3$ | H | 7A-B, 1A-D, 18D |
| D-123 | CF$_2$CH$_3$ | N | H | C | H | N | — | — | — | 2 | 1 | S | N | C | — | CH$_3$ | H | CH$_3$ | H | 7A-B, 1A-D, 18D |
| D-124 | CF$_2$HCF$_3$ | N | H | C | H | N | — | — | — | 2 | 1 | S | N | C | — | CH$_3$ | H | CH$_3$ | H | 7A-B, 1A-D, 18D |
| D-125 | CF$_2$CF$_3$ | N | H | C | H | N | — | — | — | 2 | 1 | S | N | C | — | CH$_3$ | H | CH$_3$ | H | 7A-B, 1A-D, 18D |
| D-126 | CF$_3$ | N | H | C | H | N | — | — | — | 2 | 1 | S | N | C | — | CH$_3$ | H | OCH$_3$ | H | 7A-B, 1A-D, 18D |
| D-127 | CF$_2$Cl | N | H | C | H | N | — | — | — | 2 | 1 | S | N | C | — | CH$_3$ | H | OCH$_3$ | H | 7A-B, 1A-D, 18D |
| D-128 | CF$_2$Br | N | H | C | H | N | — | — | — | 2 | 1 | S | N | C | — | CH$_3$ | H | OCH$_3$ | H | 7A-B, 1A-D, 18D |
| D-129 | CHF$_2$ | N | H | C | H | N | — | — | — | 2 | 1 | S | N | C | — | CH$_3$ | H | OCH$_3$ | H | 7A-B, 1A-D, 18D |
| D-130 | CF$_2$CH$_3$ | N | H | C | H | N | — | — | — | 2 | 1 | S | N | C | — | CH$_3$ | H | OCH$_3$ | H | 7A-B, 1A-D, 18D |
| D-131 | CF$_2$HCF$_3$ | N | H | C | H | N | — | — | — | 2 | 1 | S | N | C | — | CH$_3$ | H | OCH$_3$ | H | 7A-B, 1A-D, 18D |
| D-132 | CF$_2$CF$_3$ | N | H | C | H | N | — | — | — | 2 | 1 | S | N | C | — | CH$_3$ | H | OCH$_3$ | H | 7A-B, 1A-D, 18D |
| D-133 | CF$_3$ | N | H | C | H | N | — | — | — | 2 | 1 | S | N | C | — | CH$_3$ | H | OC$_2$H$_5$ | H | 7A-B, 1A-D, 18D |
| D-134 | CF$_2$Cl | N | H | C | H | N | — | — | — | 2 | 1 | S | N | C | — | CH$_3$ | H | OC$_2$H$_5$ | H | 7A-B, 1A-D, 18D |
| D-135 | CF$_2$Br | N | H | C | H | N | — | — | — | 2 | 1 | S | N | C | — | CH$_3$ | H | OC$_2$H$_5$ | H | 7A-B, 1A-D, 18D |
| D-136 | CHF$_2$ | N | H | C | H | N | — | — | — | 2 | 1 | S | N | C | — | CH$_3$ | H | OC$_2$H$_5$ | H | 7A-B, 1A-D, 18D |
| D-137 | CF$_2$CH$_3$ | N | H | C | H | N | — | — | — | 2 | 1 | S | N | C | — | CH$_3$ | H | OC$_2$H$_5$ | H | 7A-B, 1A-D, 18D |
| D-138 | CF$_2$HCF$_3$ | N | H | C | H | N | — | — | — | 2 | 1 | S | N | C | — | CH$_3$ | H | OC$_2$H$_5$ | H | 7A-B, 1A-D, 18D |
| D-139 | CF$_2$CF$_3$ | N | H | C | H | N | — | — | — | 2 | 1 | S | N | C | — | CH$_3$ | H | OC$_2$H$_5$ | H | 7A-B, 1A-D, 18D |
| D-140 | CF$_2$Cl | N | H | C | H | N | — | — | — | 3 | 1 | S | N | C | — | H | H | CH$_3$ | H | 7A-B, 1A-D, 18D |
| D-141 | CF$_2$Br | N | H | C | H | N | — | — | — | 3 | 1 | S | N | C | — | H | H | CH$_3$ | H | 7A-B, 1A-D, 18D |
| D-142 | CHF$_2$ | N | H | C | H | N | — | — | — | 3 | 1 | S | N | C | — | H | H | CH$_3$ | H | 7A-B, 1A-D, 18D |
| D-143 | CF$_2$HCF$_3$ | N | H | C | H | N | — | — | — | 3 | 1 | S | N | C | — | H | H | CH$_3$ | H | 7A-B, 1A-D, 18D |
| D-144 | CF$_2$CF$_3$ | N | H | C | H | N | — | — | — | 3 | 1 | S | N | C | — | H | H | CH$_3$ | H | 7A-B, 1A-D, 18D |
| D-145 | CF$_3$ | N | H | C | H | N | — | — | — | 3 | 1 | S | N | C | — | H | H | C$_2$H$_5$ | H | 7A-B, 1A-D, 18D |
| D-146 | CF$_2$Cl | N | H | C | H | N | — | — | — | 3 | 1 | S | N | C | — | H | H | C$_2$H$_5$ | H | 7A-B, 1A-D, 18D |
| D-147 | CF$_2$Br | N | H | C | H | N | — | — | — | 3 | 1 | S | N | C | — | H | H | C$_2$H$_5$ | H | 7A-B, 1A-D, 18D |
| D-148 | CHF$_2$ | N | H | C | H | N | — | — | — | 3 | 1 | S | N | C | — | H | H | C$_2$H$_5$ | H | 7A-B, 1A-D, 18D |
| D-149 | CF$_2$CH$_3$ | N | H | C | H | N | — | — | — | 3 | 1 | S | N | C | — | H | H | C$_2$H$_5$ | H | 7A-B, 1A-D, 18D |
| D-150 | CF$_2$HCF$_3$ | N | H | C | H | N | — | — | — | 3 | 1 | S | N | C | — | H | H | C$_2$H$_5$ | H | 7A-B, 1A-D, 18D |
| D-151 | CF$_2$CF$_3$ | N | H | C | H | N | — | — | — | 3 | 1 | S | N | C | — | H | H | C$_2$H$_5$ | H | 7A-B, 1A-D, 18D |
| D-152 | CF$_3$ | N | H | C | H | N | — | — | — | 3 | 1 | S | N | C | — | CH$_3$ | H | H | H | 7A-B, 1A-D, 18D |
| D-153 | CF$_2$Cl | N | H | C | H | N | — | — | — | 3 | 1 | S | N | C | — | CH$_3$ | H | H | H | 7A-B, 1A-D, 18D |
| D-154 | CF$_2$Br | N | H | C | H | N | — | — | — | 3 | 1 | S | N | C | — | CH$_3$ | H | H | H | 7A-B, 1A-D, 18D |
| D-155 | CHF$_2$ | N | H | C | H | N | — | — | — | 3 | 1 | S | N | C | — | CH$_3$ | H | H | H | 7A-B, 1A-D, 18D |
| D-156 | CF$_2$CH$_3$ | N | H | C | H | N | — | — | — | 3 | 1 | S | N | C | — | CH$_3$ | H | H | H | 7A-B, 1A-D, 18D |
| D-157 | CF$_2$HCF$_3$ | N | H | C | H | N | — | — | — | 3 | 1 | S | N | C | — | CH$_3$ | H | H | H | 7A-B, 1A-D, 18D |
| D-158 | CF$_2$CF$_3$ | N | H | C | H | N | — | — | — | 3 | 1 | S | N | C | — | CH$_3$ | H | H | H | 7A-B, 1A-D, 18D |
| D-159 | CF$_3$ | N | H | C | H | N | — | — | — | 3 | 1 | S | N | C | — | CH$_3$ | H | CH$_3$ | H | 7A-B, 1A-D, 18D |
| D-160 | CF$_2$Cl | N | H | C | H | N | — | — | — | 3 | 1 | S | N | C | — | CH$_3$ | H | CH$_3$ | H | 7A-B, 1A-D, 18D |
| D-161 | CF$_2$Br | N | H | C | H | N | — | — | — | 3 | 1 | S | N | C | — | CH$_3$ | H | CH$_3$ | H | 7A-B, 1A-D, 18D |
| D-162 | CHF$_2$ | N | H | C | H | N | — | — | — | 3 | 1 | S | N | C | — | CH$_3$ | H | CH$_3$ | H | 7A-B, 1A-D, 18D |
| D-163 | CF$_2$CH$_3$ | N | H | C | H | N | — | — | — | 3 | 1 | S | N | C | — | CH$_3$ | H | CH$_3$ | H | 7A-B, 1A-D, 18D |
| D-164 | CF$_2$HCF$_3$ | N | H | C | H | N | — | — | — | 3 | 1 | S | N | C | — | CH$_3$ | H | CH$_3$ | H | 7A-B, 1A-D, 18D |
| D-165 | CF$_2$CF$_3$ | N | H | C | H | N | — | — | — | 3 | 1 | S | N | C | — | CH$_3$ | H | CH$_3$ | H | 7A-B, 1A-D, 18D |
| D-166 | CF$_3$ | N | H | C | H | N | — | — | — | 3 | 1 | S | N | C | — | CH$_3$ | H | OCH$_3$ | H | 7A-B, 1A-D, 18D |
| D-167 | CF$_2$Cl | N | H | C | H | N | — | — | — | 3 | 1 | S | N | C | — | CH$_3$ | H | OCH$_3$ | H | 7A-B, 1A-D, 18D |
| D-168 | CF$_2$Br | N | H | C | H | N | — | — | — | 3 | 1 | S | N | C | — | CH$_3$ | H | OCH$_3$ | H | 7A-B, 1A-D, 18D |
| D-169 | CHF$_2$ | N | H | C | H | N | — | — | — | 3 | 1 | S | N | C | — | CH$_3$ | H | OCH$_3$ | H | 7A-B, 1A-D, 18D |
| D-170 | CF$_2$CH$_3$ | N | H | C | H | N | — | — | — | 3 | 1 | S | N | C | — | CH$_3$ | H | OCH$_3$ | H | 7A-B, 1A-D, 18D |
| D-171 | CF$_2$HCF$_3$ | N | H | C | H | N | — | — | — | 3 | 1 | S | N | C | — | CH$_3$ | H | OCH$_3$ | H | 7A-B, 1A-D, 18D |
| D-172 | CF$_2$CF$_3$ | N | H | C | H | N | — | — | — | 3 | 1 | S | N | C | — | CH$_3$ | H | OCH$_3$ | H | 7A-B, 1A-D, 18D |
| D-173 | CF$_3$ | N | H | C | H | N | — | — | — | 3 | 1 | S | N | C | — | CH$_3$ | H | OC$_2$H$_5$ | H | 7A-B, 1A-D, 18D |
| D-174 | CF$_2$Cl | N | H | C | H | N | — | — | — | 3 | 1 | S | N | C | — | CH$_3$ | H | OC$_2$H$_5$ | H | 7A-B, 1A-D, 18D |
| D-175 | CF$_2$Br | N | H | C | H | N | — | — | — | 3 | 1 | S | N | C | — | CH$_3$ | H | OC$_2$H$_5$ | H | 7A-B, 1A-D, 18D |
| D-176 | CHF$_2$ | N | H | C | H | N | — | — | — | 3 | 1 | S | N | C | — | CH$_3$ | H | OC$_2$H$_5$ | H | 7A-B, 1A-D, 18D |
| D-177 | CF$_2$CH$_3$ | N | H | C | H | N | — | — | — | 3 | 1 | S | N | C | — | CH$_3$ | H | OC$_2$H$_5$ | H | 7A-B, 1A-D, 18D |
| D-178 | CF$_2$HCF$_3$ | N | H | C | H | N | — | — | — | 3 | 1 | S | N | C | — | CH$_3$ | H | OC$_2$H$_5$ | H | 7A-B, 1A-D, 18D |
| D-179 | CF$_2$CF$_3$ | N | H | C | H | N | — | — | — | 3 | 1 | S | N | C | — | CH$_3$ | H | OC$_2$H$_5$ | H | 7A-B, 1A-D, 18D |
| D-180 | CF$_2$Cl | — | — | N | — | C | H | N | H | 1 | 2 | S | N | C | — | H | H | CH$_3$ | H | 6A-B, 1A-D, 18D |
| D-181 | CF$_2$Br | — | — | N | — | C | H | N | H | 1 | 2 | S | N | C | — | H | H | CH$_3$ | H | 6A-B, 1A-D, 18D |
| D-182 | CHF$_2$ | — | — | N | — | C | H | N | H | 1 | 2 | S | N | C | — | H | H | CH$_3$ | H | 6A-B, 1A-D, 18D |
| D-183 | CF$_2$HCF$_3$ | — | — | N | — | C | H | N | H | 1 | 2 | S | N | C | — | H | H | CH$_3$ | H | 6A-B, 1A-D, 18D |
| D-184 | CF$_2$CF$_3$ | — | — | N | — | C | H | N | H | 1 | 2 | S | N | C | — | H | H | CH$_3$ | H | 6A-B, 1A-D, 18D |
| D-185 | CF$_3$ | — | — | N | — | C | H | N | H | 1 | 2 | S | N | C | — | H | H | C$_2$H$_5$ | H | 6A-B, 1A-D, 18D |
| D-186 | CF$_2$Cl | — | — | N | — | C | H | N | H | 1 | 2 | S | N | C | — | H | H | C$_2$H$_5$ | H | 6A-B, 1A-D, 18D |
| D-187 | CF$_2$Br | — | — | N | — | C | H | N | H | 1 | 2 | S | N | C | — | H | H | C$_2$H$_5$ | H | 6A-B, 1A-D, 18D |
| D-188 | CHF$_2$ | — | — | N | — | C | H | N | H | 1 | 2 | S | N | C | — | H | H | C$_2$H$_5$ | H | 6A-B, 1A-D, 18D |
| D-189 | CF$_2$CH$_3$ | — | — | N | — | C | H | N | H | 1 | 2 | S | N | C | — | H | H | C$_2$H$_5$ | H | 6A-B, 1A-D, 18D |
| D-190 | CF$_2$HCF$_3$ | — | — | N | — | C | H | N | H | 1 | 2 | S | N | C | — | H | H | C$_2$H$_5$ | H | 6A-B, 1A-D, 18D |
| D-191 | CF$_2$CF$_3$ | — | — | N | — | C | H | N | H | 1 | 2 | S | N | C | — | H | H | C$_2$H$_5$ | H | 6A-B, 1A-D, 18D |
| D-192 | CF$_3$ | — | — | N | — | C | H | N | H | 1 | 2 | S | N | C | — | CH$_3$ | H | H | H | 6A-B, 1A-D, 18D |
| D-193 | CF$_2$Cl | — | — | N | — | C | H | N | H | 1 | 2 | S | N | C | — | CH$_3$ | H | H | H | 6A-B, 1A-D, 18D |

TABLE D-continued $(X = CO, Y^3, Y^4, Y^5 = C)$

| | | | | | | | | | | | | | | | | | | | | |
|---|---|---|---|---|---|---|---|---|---|---|---|---|---|---|---|---|---|---|---|---|
| D-194 | CF$_2$Br | — | — | N | — | C | H | N | H | 1 | 2 | S | N | C | — | CH$_3$ | H | H | H | 6A-B, 1A-D, 18D |
| D-195 | CHF$_2$ | — | — | N | — | C | H | N | H | 1 | 2 | S | N | C | — | CH$_3$ | H | H | H | 6A-B, 1A-D, 18D |
| D-196 | CF$_2$CH$_3$ | — | — | N | — | C | H | N | H | 1 | 2 | S | N | C | — | CH$_3$ | H | H | H | 6A-B, 1A-D, 18D |
| D-197 | CF$_2$HCF$_3$ | — | — | N | — | C | H | N | H | 1 | 2 | S | N | C | — | CH$_3$ | H | H | H | 6A-B, 1A-D, 18D |
| D-198 | CF$_2$CF$_3$ | — | — | N | — | C | H | N | H | 1 | 2 | S | N | C | — | CH$_3$ | H | H | H | 6A-B, 1A-D, 18D |
| D-199 | CF$_3$ | — | — | N | — | C | H | N | H | 1 | 2 | S | N | C | — | CH$_3$ | H | CH$_3$ | H | 6A-B, 1A-D, 18D |
| D-200 | CF$_2$Cl | — | — | N | — | C | H | N | H | 1 | 2 | S | N | C | — | CH$_3$ | H | CH$_3$ | H | 6A-B, 1A-D, 18D |
| D-201 | CF$_2$Br | — | — | N | — | C | H | N | H | 1 | 2 | S | N | C | — | CH$_3$ | H | CH$_3$ | H | 6A-B, 1A-D, 18D |
| D-202 | CHF$_2$ | — | — | N | — | C | H | N | H | 1 | 2 | S | N | C | — | CH$_3$ | H | CH$_3$ | H | 6A-B, 1A-D, 18D |
| D-203 | CF$_2$CH$_3$ | — | — | N | — | C | H | N | H | 1 | 2 | S | N | C | — | CH$_3$ | H | CH$_3$ | H | 6A-B, 1A-D, 18D |
| D-204 | CF$_2$HCF$_3$ | — | — | N | — | C | H | N | H | 1 | 2 | S | N | C | — | CH$_3$ | H | CH$_3$ | H | 6A-B, 1A-D, 18D |
| D-205 | CF$_2$CF$_3$ | — | — | N | — | C | H | N | H | 1 | 2 | S | N | C | — | CH$_3$ | H | CH$_3$ | H | 6A-B, 1A-D, 18D |
| D-206 | CF$_3$ | — | — | N | — | C | H | N | H | 1 | 2 | S | N | C | — | CH$_3$ | H | OCH$_3$ | H | 6A-B, 1A-D, 18D |
| D-207 | CF$_2$Cl | — | — | N | — | C | H | N | H | 1 | 2 | S | N | C | — | CH$_3$ | H | OCH$_3$ | H | 6A-B, 1A-D, 18D |
| D-208 | CF$_2$Br | — | — | N | — | C | H | N | H | 1 | 2 | S | N | C | — | CH$_3$ | H | OCH$_3$ | H | 6A-B, 1A-D, 18D |
| D-209 | CHF$_2$ | — | — | N | — | C | H | N | H | 1 | 2 | S | N | C | — | CH$_3$ | H | OCH$_3$ | H | 6A-B, 1A-D, 18D |
| D-210 | CF$_2$CH$_3$ | — | — | N | — | C | H | N | H | 1 | 2 | S | N | C | — | CH$_3$ | H | OCH$_3$ | H | 6A-B, 1A-D, 18D |
| D-211 | CF$_2$HCF$_3$ | — | — | N | — | C | H | N | H | 1 | 2 | S | N | C | — | CH$_3$ | H | OCH$_3$ | H | 6A-B, 1A-D, 18D |
| D-212 | CF$_2$CF$_3$ | — | — | N | — | C | H | N | H | 1 | 2 | S | N | C | — | CH$_3$ | H | OCH$_3$ | H | 6A-B, 1A-D, 18D |
| D-213 | CF$_3$ | — | — | N | — | C | H | N | H | 1 | 2 | S | N | C | — | CH$_3$ | H | OC$_2$H$_5$ | H | 6A-B, 1A-D, 18D |
| D-214 | CF$_2$Cl | — | — | N | — | C | H | N | H | 1 | 2 | S | N | C | — | CH$_3$ | H | OC$_2$H$_5$ | H | 6A-B, 1A-D, 18D |
| D-215 | CF$_2$Br | — | — | N | — | C | H | N | H | 1 | 2 | S | N | C | — | CH$_3$ | H | OC$_2$H$_5$ | H | 6A-B, 1A-D, 18D |
| D-216 | CHF$_2$ | — | — | N | — | C | H | N | H | 1 | 2 | S | N | C | — | CH$_3$ | H | OC$_2$H$_5$ | H | 6A-B, 1A-D, 18D |
| D-217 | CF$_2$CH$_3$ | — | — | N | — | C | H | N | H | 1 | 2 | S | N | C | — | CH$_3$ | H | OC$_2$H$_5$ | H | 6A-B, 1A-D, 18D |
| D-218 | CF$_2$HCF$_3$ | — | — | N | — | C | H | N | H | 1 | 2 | S | N | C | — | CH$_3$ | H | OC$_2$H$_5$ | H | 6A-B, 1A-D, 18D |
| D-219 | CF$_2$CF$_3$ | — | — | N | — | C | H | N | H | 1 | 2 | S | N | C | — | CH$_3$ | H | OC$_2$H$_5$ | H | 6A-B, 1A-D, 18D |
| D-220 | CF$_2$Cl | — | — | N | — | C | H | N | H | 1 | 3 | S | N | C | — | H | H | CH$_3$ | H | 6A-B, 1A-D, 18D |
| D-221 | CF$_2$Br | — | — | N | — | C | H | N | H | 1 | 3 | S | N | C | — | H | H | CH$_3$ | H | 6A-B, 1A-D, 18D |
| D-222 | CHF$_2$ | — | — | N | — | C | H | N | H | 1 | 3 | S | N | C | — | H | H | CH$_3$ | H | 6A-B, 1A-D, 18D |
| D-223 | CF$_2$HCF$_3$ | — | — | N | — | C | H | N | H | 1 | 3 | S | N | C | — | H | H | CH$_3$ | H | 6A-B, 1A-D, 18D |
| D-224 | CF$_2$CF$_3$ | — | — | N | — | C | H | N | H | 1 | 3 | S | N | C | — | H | H | CH$_3$ | H | 6A-B, 1A-D, 18D |
| D-225 | CF$_3$ | — | — | N | — | C | H | N | H | 1 | 3 | S | N | C | — | H | H | C$_2$H$_5$ | H | 6A-B, 1A-D, 18D |
| D-226 | CF$_2$Cl | — | — | N | — | C | H | N | H | 1 | 3 | S | N | C | — | H | H | C$_2$H$_5$ | H | 6A-B, 1A-D, 18D |
| D-227 | CF$_2$Br | — | — | N | — | C | H | N | H | 1 | 3 | S | N | C | — | H | H | C$_2$H$_5$ | H | 6A-B, 1A-D, 18D |
| D-228 | CHF$_2$ | — | — | N | — | C | H | N | H | 1 | 3 | S | N | C | — | H | H | C$_2$H$_5$ | H | 6A-B, 1A-D, 18D |
| D-229 | CF$_2$CH$_3$ | — | — | N | — | C | H | N | H | 1 | 3 | S | N | C | — | H | H | C$_2$H$_5$ | H | 6A-B, 1A-D, 18D |
| D-230 | CF$_2$HCF$_3$ | — | — | N | — | C | H | N | H | 1 | 3 | S | N | C | — | H | H | C$_2$H$_5$ | H | 6A-B, 1A-D, 18D |
| D-231 | CF$_2$CF$_3$ | — | — | N | — | C | H | N | H | 1 | 3 | S | N | C | — | H | H | C$_2$H$_5$ | H | 6A-B, 1A-D, 18D |
| D-232 | CF$_3$ | — | — | N | — | C | H | N | H | 1 | 3 | S | N | C | — | CH$_3$ | H | H | H | 6A-B, 1A-D, 18D |
| D-233 | CF$_2$Cl | — | — | N | — | C | H | N | H | 1 | 3 | S | N | C | — | CH$_3$ | H | H | H | 6A-B, 1A-D, 18D |
| D-234 | CF$_2$Br | — | — | N | — | C | H | N | H | 1 | 3 | S | N | C | — | CH$_3$ | H | H | H | 6A-B, 1A-D, 18D |
| D-235 | CHF$_2$ | — | — | N | — | C | H | N | H | 1 | 3 | S | N | C | — | CH$_3$ | H | H | H | 6A-B, 1A-D, 18D |
| D-236 | CF$_2$CH$_3$ | — | — | N | — | C | H | N | H | 1 | 3 | S | N | C | — | CH$_3$ | H | H | H | 6A-B, 1A-D, 18D |
| D-237 | CF$_2$HCF$_3$ | — | — | N | — | C | H | N | H | 1 | 3 | S | N | C | — | CH$_3$ | H | H | H | 6A-B, 1A-D, 18D |
| D-238 | CF$_2$CF$_3$ | — | — | N | — | C | H | N | H | 1 | 3 | S | N | C | — | CH$_3$ | H | H | H | 6A-B, 1A-D, 18D |
| D-239 | CF$_3$ | — | — | N | — | C | H | N | H | 1 | 3 | S | N | C | — | CH$_3$ | H | CH$_3$ | H | 6A-B, 1A-D, 18D |
| D-240 | CF$_2$Cl | — | — | N | — | C | H | N | H | 1 | 3 | S | N | C | — | CH$_3$ | H | CH$_3$ | H | 6A-B, 1A-D, 18D |
| D-241 | CF$_2$Br | — | — | N | — | C | H | N | H | 1 | 3 | S | N | C | — | CH$_3$ | H | CH$_3$ | H | 6A-B, 1A-D, 18D |
| D-242 | CHF$_2$ | — | — | N | — | C | H | N | H | 1 | 3 | S | N | C | — | CH$_3$ | H | CH$_3$ | H | 6A-B, 1A-D, 18D |
| D-243 | CF$_2$CH$_3$ | — | — | N | — | C | H | N | H | 1 | 3 | S | N | C | — | CH$_3$ | H | CH$_3$ | H | 6A-B, 1A-D, 18D |
| D-244 | CF$_2$HCF$_3$ | — | — | N | — | C | H | N | H | 1 | 3 | S | N | C | — | CH$_3$ | H | CH$_3$ | H | 6A-B, 1A-D, 18D |
| D-245 | CF$_2$CF$_3$ | — | — | N | — | C | H | N | H | 1 | 3 | S | N | C | — | CH$_3$ | H | CH$_3$ | H | 6A-B, 1A-D, 18D |
| D-246 | CF$_3$ | — | — | N | — | C | H | N | H | 1 | 3 | S | N | C | — | CH$_3$ | H | OCH$_3$ | H | 6A-B, 1A-D, 18D |
| D-247 | CF$_2$Cl | — | — | N | — | C | H | N | H | 1 | 3 | S | N | C | — | CH$_3$ | H | OCH$_3$ | H | 6A-B, 1A-D, 18D |
| D-248 | CF$_2$Br | — | — | N | — | C | H | N | H | 1 | 3 | S | N | C | — | CH$_3$ | H | OCH$_3$ | H | 6A-B, 1A-D, 18D |
| D-249 | CHF$_2$ | — | — | N | — | C | H | N | H | 1 | 3 | S | N | C | — | CH$_3$ | H | OCH$_3$ | H | 6A-B, 1A-D, 18D |
| D-250 | CF$_2$CH$_3$ | — | — | N | — | C | H | N | H | 1 | 3 | S | N | C | — | CH$_3$ | H | OCH$_3$ | H | 6A-B, 1A-D, 18D |
| D-251 | CF$_2$HCF$_3$ | — | — | N | — | C | H | N | H | 1 | 3 | S | N | C | — | CH$_3$ | H | OCH$_3$ | H | 6A-B, 1A-D, 18D |
| D-252 | CF$_2$CF$_3$ | — | — | N | — | C | H | N | H | 1 | 3 | S | N | C | — | CH$_3$ | H | OCH$_3$ | H | 6A-B, 1A-D, 18D |
| D-253 | CF$_3$ | — | — | N | — | C | H | N | H | 1 | 3 | S | N | C | — | CH$_3$ | H | OC$_2$H$_5$ | H | 6A-B, 1A-D, 18D |
| D-254 | CF$_2$Cl | — | — | N | — | C | H | N | H | 1 | 3 | S | N | C | — | CH$_3$ | H | OC$_2$H$_5$ | H | 6A-B, 1A-D, 18D |
| D-255 | CF$_2$Br | — | — | N | — | C | H | N | H | 1 | 3 | S | N | C | — | CH$_3$ | H | OC$_2$H$_5$ | H | 6A-B, 1A-D, 18D |
| D-256 | CHF$_2$ | — | — | N | — | C | H | N | H | 1 | 3 | S | N | C | — | CH$_3$ | H | OC$_2$H$_5$ | H | 6A-B, 1A-D, 18D |
| D-257 | CF$_2$CH$_3$ | — | — | N | — | C | H | N | H | 1 | 3 | S | N | C | — | CH$_3$ | H | OC$_2$H$_5$ | H | 6A-B, 1A-D, 18D |
| D-258 | CF$_2$HCF$_3$ | — | — | N | — | C | H | N | H | 1 | 3 | S | N | C | — | CH$_3$ | H | OC$_2$H$_5$ | H | 6A-B, 1A-D, 18D |
| D-259 | CF$_2$CF$_3$ | — | — | N | — | C | H | N | H | 1 | 3 | S | N | C | — | CH$_3$ | H | OC$_2$H$_5$ | H | 6A-B, 1A-D, 18D |
| D-260 | CF$_3$ | N | CH$_3$ | C | H | N | — | — | — | 1 | 2 | S | N | C | — | H | H | CH$_3$ | H | 7A-B, 1A-D, 18D |
| D-261 | CF$_2$Cl | N | CH$_3$ | C | H | N | — | — | — | 1 | 2 | S | N | C | — | H | H | CH$_3$ | H | 7A-B, 1A-D, 18D |
| D-262 | CF$_2$Br | N | CH$_3$ | C | H | N | — | — | — | 1 | 2 | S | N | C | — | H | H | CH$_3$ | H | 7A-B, 1A-D, 18D |
| D-263 | CHF$_2$ | N | CH$_3$ | C | H | N | — | — | — | 1 | 2 | S | N | C | — | H | H | CH$_3$ | H | 7A-B, 1A-D, 18D |
| D-264 | CF$_2$CH$_3$ | N | CH$_3$ | C | H | N | — | — | — | 1 | 2 | S | N | C | — | H | H | CH$_3$ | H | 7A-B, 1A-D, 18D |
| D-265 | CF$_2$HCF$_3$ | N | CH$_3$ | C | H | N | — | — | — | 1 | 2 | S | N | C | — | H | H | CH$_3$ | H | 7A-B, 1A-D, 18D |
| D-266 | CF$_2$CF$_3$ | N | CH$_3$ | C | H | N | — | — | — | 1 | 2 | S | N | C | — | H | H | CH$_3$ | H | 7A-B, 1A-D, 18D |
| D-267 | CF$_3$ | — | — | N | — | C | H | N | CH$_3$ | 1 | 2 | S | N | C | — | H | H | CH$_3$ | H | 6A-B, 1A-D, 18D |
| D-268 | CF$_2$Cl | — | — | N | — | C | H | N | CH$_3$ | 1 | 2 | S | N | C | — | H | H | CH$_3$ | H | 6A-B, 1A-D, 18D |
| D-269 | CF$_2$Br | — | — | N | — | C | H | N | CH$_3$ | 1 | 2 | S | N | C | — | H | H | CH$_3$ | H | 6A-B, 1A-D, 18D |
| D-270 | CHF$_2$ | — | — | N | — | C | H | N | CH$_3$ | 1 | 2 | S | N | C | — | H | H | CH$_3$ | H | 6A-B, 1A-D, 18D |
| D-271 | CF$_2$CH$_3$ | — | — | N | — | C | H | N | CH$_3$ | 1 | 2 | S | N | C | — | H | H | CH$_3$ | H | 6A-B, 1A-D, 18D |

TABLE D-continued (X = CO, Y³, Y⁴, Y⁵ = C)

| | | | | | | | | | | | | | | | | | | | | |
|---|---|---|---|---|---|---|---|---|---|---|---|---|---|---|---|---|---|---|---|---|
| D-272 | CF$_2$HCF$_3$ | — | — | N | — | C | H | N | CH$_3$ | 1 | 2 | S | N | C | — | H | H | CH$_3$ | H | 6A-B, 1A-D, 18D |
| D-273 | CF$_2$CF$_3$ | — | — | N | — | C | H | N | CH$_3$ | 1 | 2 | S | N | C | — | H | H | CH$_3$ | H | 6A-B, 1A-D, 18D |
| D-274 | CF$_3$ | N | H | C | CH$_3$ | N | — | — | — | 1 | 2 | RS | N | C | — | H | H | CH$_3$ | H | 7A-B, 1A-D, 18D |
| D-275 | CF$_2$Cl | N | H | C | CH$_3$ | N | — | — | — | 1 | 2 | RS | N | C | — | H | H | CH$_3$ | H | 7A-B, 1A-D, 18D |
| D-276 | CF$_2$Br | N | H | C | CH$_3$ | N | — | — | — | 1 | 2 | RS | N | C | — | H | H | CH$_3$ | H | 7A-B, 1A-D, 18D |
| D-277 | CHF$_2$ | N | H | C | CH$_3$ | N | — | — | — | 1 | 2 | RS | N | C | — | H | H | CH$_3$ | H | 7A-B, 1A-D, 18D |
| D-278 | CF$_2$CH$_3$ | N | H | C | CH$_3$ | N | — | — | — | 1 | 2 | RS | N | C | — | H | H | CH$_3$ | H | 7A-B, 1A-D, 18D |
| D-279 | CF$_2$HCF$_3$ | N | H | C | CH$_3$ | N | — | — | — | 1 | 2 | RS | N | C | — | H | H | CH$_3$ | H | 7A-B, 1A-D, 18D |
| D-280 | CF$_2$CF$_3$ | N | H | C | CH$_3$ | N | — | — | — | 1 | 2 | RS | N | C | — | H | H | CH$_3$ | H | 7A-B, 1A-D, 18D |
| D-281 | CF$_3$ | — | — | N | — | C | CH$_3$ | N | H | 1 | 2 | RS | N | C | — | H | H | CH$_3$ | H | 6A-B, 1A-D, 18D |
| D-282 | CF$_2$Cl | — | — | N | — | C | CH$_3$ | N | H | 1 | 2 | RS | N | C | — | H | H | CH$_3$ | H | 6A-B, 1A-D, 18D |
| D-283 | CF$_2$Br | — | — | N | — | C | CH$_3$ | N | H | 1 | 2 | RS | N | C | — | H | H | CH$_3$ | H | 6A-B, 1A-D, 18D |
| D-284 | CHF$_2$ | — | — | N | — | C | CH$_3$ | N | H | 1 | 2 | RS | N | C | — | H | H | CH$_3$ | H | 6A-B, 1A-D, 18D |
| D-285 | CF2CH3 | — | — | N | — | C | CH3 | N | H | 1 | 2 | RS | N | C | — | H | H | CH$_3$ | H | 6A-B, 1A-D, 18D |
| D-286 | CF2HCF3 | — | — | N | — | C | CH3 | N | H | 1 | 2 | RS | N | C | — | H | H | CH$_3$ | H | 6A-B, 1A-D, 18D |
| D-287 | CF2CF3 | — | — | N | — | C | CH3 | N | H | 1 | 2 | RS | N | C | — | H | H | CH$_3$ | H | 6A-B, 1A-D, 18D |

Further examples of specific compounds of the present invention include each of the compounds D-48 to D-273 with R-configuration.

Further examples of specific compounds of the present invention include each of the compounds of table D above (including R and S enantiomers) wherein X=SO$_2$ instead of CO and each of the compounds of table D wherein X=CS instead of CO.

Further examples of specific compounds of the present invention include each of the compounds in table A, C and D and their analogues wherein X=SO$_2$ and X=CS and wherein one of Y$^1$, Y$^2$, Y$^3$, Y$^4$ or Y$^5$ is N in form of its pyridine N-oxide such as the N-oxides shown in table E below:

| No | Structure | HPLC | Rt | m/z | MW |
|---|---|---|---|---|---|
| E-1 | 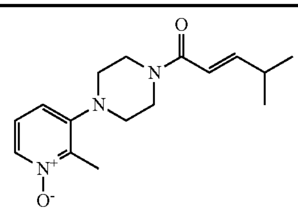 | 2 | 0.78 | 290.2 | 289.4 |
| E-2 | 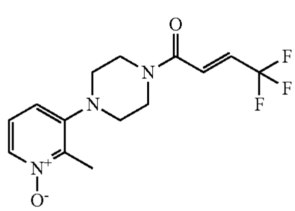 [SMILES: Cc1c(N2CCN(C(=O)/C=C/C(F)(F)F)CC2)ccc[n+]1[O-]] | 2 | 0.75 | 316.0 | 315.3 |
| E-3 | 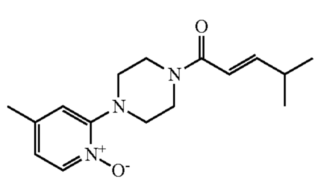 [SMILES: Cc1cc[n+]([O-])c(N2CCN(C(=O)/C=C/C(C)C)CC2)c1] | 4 | 1.51 | 290.2 | 289.4 |
| E-4 | 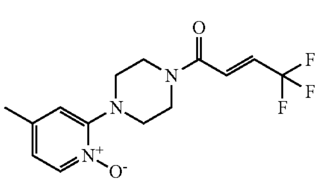 [SMILES: Cc1cc[n+]([O-])c(N2CCN(C(=O)/C=C/C(F)(F)F)CC2)c1] | 4 | 1.48 | 316.1 | 315.3 |

E. Biological Examples

Activity Against *Ascaridia galli* and *Oesophagostomum dentatum*

Anthelmintic effects of compounds of this invention were tested in vitro using gut-welling larval stages of two parasitic nematode species: *Ascaridia galli* (intestinal roundworm of chicken), larval stage 3 ("L3"); and *Oesophagostomum dentatum* (nodular worm of swine), larval stages 3 and 4 (respectively "L3" and "L4"). When conducting these experiments, DMSO-solutions of various concentrations of compounds of this invention were prepared and incubated in 96-well microtiter plates. The parasites were then distributed at 20 larvae per well. The anthelmintic effects were classified by microscopic examination. The microscopic examination included assessing mortality, damage, motility, progression of development, and neutral red uptake by the larvae in comparison to a DMSO-control. The anthelmintic effects were defined by the minimum effective concentration ("MEC"), which is the concentration by which at least one of the larvae shows mortality, damage, change in motility, change in progression of development, or no neutral red uptake. The following compounds showed activity against one or both of the nematodes with an MEC of 50 µM or less: A-1-A-18, A-21, A-25-A-27, A-29-A-31, A-34, A-35, A-38-A-50, A-55-A-59, A-61-A-131, B-4-B-35, C-1-C-18, D-1-D-18, D-21-D-25, D-33, D-36-D-47, E-2, E-4.

DEFINITIONS

The term "alkyl" (alone or in combination with another term(s)) means an acyclic (i.e. straight-chain or branched-chain) or cyclic saturated hydrocarbyl substituent (i.e., a substituent containing only carbon and hydrogen) which unless otherwise specified typically contains from 1 to 6 carbon atoms (indicated as "C1-C6 alkyl" or "$C_1$-$C_6$ alkyl"), and even more typically from 1 to about 4 carbon atoms. Examples of such substituents include methyl, ethyl, n-propyl, isopropyl, n-butyl, iso-butyl, sec-butyl, tert-butyl, pentyl, iso-pentyl, hexyl, and octyl. For instance the term "$C_1$-$C_6$-alkyl" includes but is not limited to methyl, ethyl, n-propyl, isopropyl, cyclopropyl, methylcyclopropyl, n-butyl, iso-butyl, sec-butyl, tert-butyl, cyclobutyl, methylcyclobutyl, n-pentyl, iso-pentyl, neo-pentyl, cyclopentyl, methylcyclopentyl, n-hexyl, iso-hexyl and cyclohexyl.

Typically preferred alkyl substituents are acyclic alkyl substituents such as acyclic $C_1$-$C_6$alkyl which includes but is not limited to methyl, ethyl, n-propyl, isopropyl, n-butyl, isobutyl, sec-butyl, tert-butyl, n-pentyl, iso-pentyl, neo-pentyl, n-hexyl and iso-hexyl, more preferred are methyl and ethyl, even more preferred is typically methyl. For $R^1$ cyclic alkyl substituents such as cyclic $C_1$-$C_6$alkyl are also preferred, however acyclic alkyl substituents such as acyclic $C_1$-$C_6$alkyl are even more preferred.

The term "alkenyl" (alone or in combination with another term(s)) means a straight- or branched-chain hydrocarbyl substituent containing one or more double bonds and unless otherwise specified typically contains from 2 to 6 carbon atoms, even more typically from 2 to 4 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; and 2-hexenyl.

The term "alkynyl" (alone or in combination with another term(s)) means a straight- or branched-chain hydrocarbyl substituent containing one or more triple bonds and unless otherwise specified typically from 2 to 6 atoms, even more typically from 2 to 4 carbon atoms. Examples of such substituents include ethynyl, 2-propynyl, 3-propynyl, 1-butynyl, 2-butynyl, 3-butynyl, and 2-hexynyl.

The term "halogen" (alone or in combination with another term(s)) means a fluorine radical ("fluoro", which may be depicted as F), chlorine radical ("chloro", which may be depicted as Cl), bromine radical ("bromo", which may be depicted as Br), or iodine radical ("iodo", which may be depicted as I). Typically, fluoro or chloro is preferred.

The term "alkylsulfoxyl" means an alkyl as defined above bound to an (S=O) group such that if this "alkylsulfoxyl" is bound to, for example, another alkyl group, a sulfoxide is formed.

When a chemical formula is used to describe a monovalent substituent, the dash on the left side of the formula indicates the portion of the substituent that has the free valence. To illustrate, benzene substituted with —C(O)—OH has the following structure:

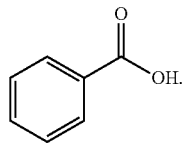

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure.

The term "pharmaceutically acceptable" is used adjectivally to mean that the modified noun is appropriate for use in a pharmaceutical product. When it is used, for example, to describe a salt, solvate, N-oxide, active compound or excipient, it characterizes the salt, solvate, N-oxide, active compound or excipient as being compatible with the other ingredients of the composition, and not deleterious to the intended recipient animal, e.g. to the extent that the benefit(s) outweigh(s) the deleterious effect(s).

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:

1. A compound having the structure of formula (V), and N-oxides, and salts thereof,

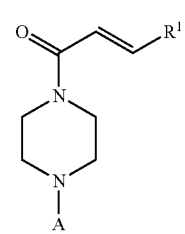

Formula (V)

wherein $R^1$ is hydrogen, halogen, alkyl, alkoxy, alkenyl, alkynyl, alkylthio, alkoxyalkyl, alkylthioalkyl, alkylcarbonyl, alkylsulfonyl, $SF_5$, alkoxycarbonyl, wherein each of the carbon-containing radicals optionally is substituted by one or more halogen atoms, and A is a 5 membered heteroaromate according to formula III,

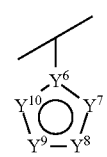

Formula III wherein in formula III:

$Y^6$ is N or C, $Y^7$, $Y^8$, $Y^9$ and $Y^{10}$ is $CR^{14}$, $NR^{15}$, O, S $R^{14}$ is hydrogen, alkyl, alkoxy, alkylthio, halogen, nitrilo, nitro, alkoxycarbonyl, aminocarbonyl, methylsulfonyl, aminosulfonyl, alkylsulfonyl, alkylamino, dialkylamino, N-pyrrolidinyl, N-piperidinyl, N-morpholinyl, phenyl, wherein each of the carbon-containing radicals optionally is substituted by one or more halogen atoms, $R^{15}$ is missing, at least one of $Y^7$, $Y^8$, $Y^9$ and $Y^{10}$ is N, O or S, $Y^7$ and $Y^8$ may form a ring system or $Y^8$ and $Y^9$ may form a ring system or $Y^9$ and $Y^{10}$ may form a ring system.

2. A method of treating a helminth infection of an animal by administering to that animal a compound of the formula (I) or a pharmaceutically acceptable N-oxide, or salt thereof,

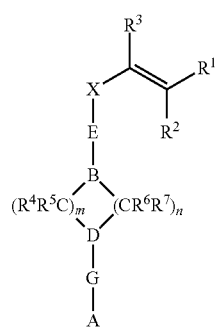

Formula I wherein $R^1$ is hydrogen, halogen, alkyl, alkoxy, alkoxyalkyl, alkenyl, alkynyl, alkylthio, alkylthioalkyl, alkylcarbonyl, SF$_5$, alkoxycarbonyl, wherein each of the carbon-containing radicals optionally is substituted by one or more halogen atoms, R$^2$ is hydrogen, halogen, alkyl, alkoxy, alkenyl, alkynyl, alkylthio, alkoxyalkyl, alkylthioalkyl, alkylcarbonyl, alkylsulfonyl, SF$_5$, alkoxycarbonyl, phenyl, thiophenyl, furanyl, imidazolyl wherein each of the carbon-containing radicals optionally is substituted by one or more halogen atoms, R$^3$ is hydrogen, halogen or alkyl, wherein each of the carbon atoms of the alkyl is optionally substituted by one or more halogen atoms, R$^4$ is hydrogen or alkyl,
R$^5$ is hydrogen or alkyl,
R$^6$ is hydrogen, alkyl, phenyl or benzyl,
R$^7$ is hydrogen or alkyl, or R$^6$ or R$^7$ are joined together with R$^4$ or R$^5$ to form a C1-C3 alkylene group which is optionally substituted by one or more alkyl radicals,
m, n is 1-3,
X is CO, CS or SO$_2$,
E is a bond or NR$^8$ wherein R$^8$ is hydrogen or alkyl,
G is a bond or NR$^9$ wherein R$^9$ is hydrogen or alkyl,
B is N or CR$^{10}$ wherein R$^{10}$ is hydrogen or alkyl,
D is N or CR$^{11}$ wherein R$^{11}$ is hydrogen or alkyl, and
A is a 5 membered heteroaromate according to formula III,

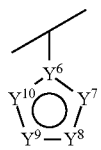

Formula III wherein in formula III:
Y$^6$ is N or C,
Y$^7$, Y$^8$, Y$^9$ and Y$^{10}$ is CR$^{14}$, NR$^{15}$, O or S, wherein at least one and at maximum three of Y$^7$,
Y$^8$, Y$^9$ and Y$^{10}$ is NR$^{15}$, O or S,
R$^{14}$ is hydrogen, alkyl, alkoxy, alkylthio, halogen, nitrilo, nitro, alkoxycarbonyl, aminocarbonyl, alkylsulfonyl, aminosulfonyl, alkylamino, dialkylamino, N-pyrrolidinyl, N-piperidinyl, N-morpholinyl, phenyl, wherein each of the carbon-containing radicals optionally is substituted by one or more halogen atoms,
R$^{15}$ is missing,
Y$^7$ and Y$^8$ may form a ring system or Y$^8$ and Y$^9$ may form a ring system or Y$^9$ and Y$^{10}$ may form a ring system.

3. A method according to claim 2, wherein R$^2$ is hydrogen, halogen, alkyl or alkoxy and R$^8$, R$^9$, R$^{10}$ and R$^{11}$ are hydrogen.

4. A method according to claim 2, wherein
R$^1$ is hydrogen, halogen, alkyl, haloalkyl, alkoxy, alkylthio, alkenyl, alkylcarbonyl, alkoxycarbonyl, alkinyl, alkylthioalkyl, SF$_5$,
R$^2$ is hydrogen, halogen or alkyl,
R$^3$ is hydrogen, halogen or alkyl,
R$^4$, R$^5$, R$^6$ and R$^7$ is hydrogen,
R$^{10}$ is hydrogen,
R$^{11}$ is hydrogen, and
in formula III:
Y$^7$ and Y$^8$ is CR$^{14}$, NR$^{15}$, O or S, and Y$^9$ and Y$^{10}$ are CR$^{14}$ or NR$^{15}$,
R$^{14}$ is hydrogen, alkyl, haloalkyl, halogen, nitrilo, amino, nitro, alkylsulfonyl, alkylsulfoxyl, alkoxycarbonyl or aminocarbonyl.

5. A method according to claim 4, wherein
R$^1$ is hydrogen, chloro, propenyl, methylcarbonyl, ethoxycarbonyl, butynyl, SF$_5$, C1-C4 alkyl, C1-C2 alkoxy, C1-C2 alkylthio, C1-C2 alkylthio-C1-C2 alkyl, each carbon containing radical optionally is substituted by one or more fluorine atoms,
R$^2$ is hydrogen, chloro or C1-C2 alkyl,
R$^3$ is hydrogen or C1-C2 alkyl,
R$^8$ is hydrogen
R$^9$ is hydrogen, and
In formula III:
R$^{14}$ is hydrogen, C1-C2 alkyl, C1-C2 alkoxy or C1-C2 alkylthio
R$^{15}$ is missing.

6. A method according to claim 5, wherein
R$^1$ is hydrogen, C1-C4 alkyl optionally substituted by one or more fluorine atoms,
R$^2$ is hydrogen,
R$^3$ is hydrogen,
X is CO,
at least one of B and D is N,
m, n are 1 or 2, and
in formula III:
R$^{14}$ is hydrogen or methyl,
R$^{15}$ is missing.

7. A method according to claim 6, wherein if B is N and D is C then E is a bond and G is N, or wherein if B is C and D is N then E is N and G is a bond.

8. A method according to claim 6, wherein
R$^1$ is C1-C2 alkyl optionally substituted by one or more fluorine atoms,
B is N,
D is N,
E, G are bonds,
m, n are 2
A is a monocyclic ring system.

9. A method according to claim 8, wherein A is a thiazole, oxadiazole, thiophene, imidazole, or a benzimidazole.

10. A method according to claim 9, wherein A is a pyridine, thiazole, oxadiazole, imidazole or a thiophene.

11. A method according to claim 2, wherein the compound has the structure of formula (IV),

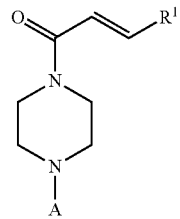

Formula (IV)

wherein
R$^1$ is hydrogen, halogen, alkyl, alkoxy, alkenyl, alkynyl, alkylthio, alkylthioalkyl, alkylcarbonyl, SF$_5$, alkoxycarbonyl, wherein each of the carbon-containing radicals optionally is substituted by one or more halogen atoms, and
in formula III:
Y$^6$ is N or C,
Y$^7$, Y$^8$, Y$^9$ and Y$^{10}$ is CR$^{14}$, NR$^{15}$, O, S
R$^{14}$ is hydrogen, alkyl, alkoxy, alkylthio, halogen, nitrilo, nitro, alkoxycarbonyl, aminocarbonyl, aminosulfonyl, alkylsulfonyl, alkylamino, dialkylamino, N-pyrrolidinyl, N-piperidinyl, N-morpholinyl, phenyl, wherein each of the carbon-containing radicals optionally is substituted by one or more halogen atoms, $R^{15}$ is missing, at least one of $Y^7$, $Y^8$, $Y^9$ and $Y^{10}$ is N, O or S, $Y^7$ and $Y^8$ may form a ring system or $Y^8$ and $Y^9$ may form a ring system or $Y^9$ and $Y^{10}$ may form a ring system.

12. A method according to claim 11, wherein $R^1$ is hydrogen, halogen, alkyl, haloalkyl, alkoxy, alkylthio, alkenyl, alkylcarbonyl, alkoxycarbonyl, alkinyl, alkylthioalkyl, $SF_5$, wherein each of the carbon-containing radicals optionally is substituted by one or more halogen atoms.

13. A method according to claim 12, wherein $R^1$ is hydrogen, chloro, propenyl, methylcarbonyl, ethoxycarbonyl, butynyl, $SF_5$, C1-C4 alkyl, C1-C2 alkoxy, C1-C2 alkylthio, C1-C2 alkylthio-C1-C2 alkyl, each carbon containing radical optionally is substituted by one or more fluorine atoms.

14. A method according to claim 13, wherein $R^1$ is C1-C4 alkyl optionally substituted by one or more fluorine atoms.

15. A method according to claim 11, wherein
in formula III:
$Y^7$ and $Y^8$ is $CR^{14}$, $NR^{15}$, O or S, and $Y^9$ and $Y^{10}$ are $CR^{14}$ or $NR^{15}$,
$R^{14}$ is hydrogen, alkyl, haloalkyl, halogen, nitrilo, amino, nitro, alkylsulfonyl, alkoxycarbonyl, aminocarbonyl.

16. A method according to claim 15, wherein
in formula III:
$R^{14}$ is hydrogen, C1-C2 alkyl, C1-C2 alkoxy or C1-C2 alkylthio
$R^{15}$ is missing.

17. A method according to claim 16, wherein
in formula III:
$R^{14}$ is hydrogen or methyl,
$R^{15}$ is missing.

18. A method according to claim 11, wherein A is a thiazole, oxadiazole, imidazole, thiophene, or a benzimidazole.

19. A method according to claim 18, wherein A is a pyridine, thiazole, imidazole, oxadiazole or a thiophene.

20. A method according to claim 2 wherein A is a monocyclic or bicyclic ring system.

21. A method according to claim 11, wherein A is a monocyclic or bicyclic ring system.

* * * * *